(12) United States Patent
Chen et al.

(10) Patent No.: US 7,491,804 B2
(45) Date of Patent: Feb. 17, 2009

(54) DNA DEPENDENT PROTEIN KINASE CATALYTIC SUBUNIT PHOSPHORYLATION SITES AND ANTIBODIES THERETO

(75) Inventors: David J. Chen, Moraga, CA (US); Ping-Chi Benjamin Chen, Walnut Creek, CA (US); Doug W. Chan, Houston, TX (US)

(73) Assignee: The Regents of the University of California, Oakland, CA (US)

( * ) Notice: Subject to any disclaimer, the term of this patent is extended or adjusted under 35 U.S.C. 154(b) by 380 days.

(21) Appl. No.: 10/511,561

(22) PCT Filed: Apr. 21, 2003

(86) PCT No.: PCT/US03/12380

§ 371 (c)(1),
(2), (4) Date: Oct. 15, 2004

(87) PCT Pub. No.: WO03/089474

PCT Pub. Date: Oct. 30, 2003

(65) Prior Publication Data

US 2005/0176935 A1      Aug. 11, 2005

Related U.S. Application Data

(60) Provisional application No. 60/375,094, filed on Apr. 22, 2002.

(51) Int. Cl.
*C07K 16/40*      (2006.01)
(52) U.S. Cl. .............. 530/388.23; 530/327; 530/388.15
(58) Field of Classification Search ........................ None
See application file for complete search history.

(56) References Cited

U.S. PATENT DOCUMENTS 4,474,982 A * 10/1984 Howells ..................... 560/223

OTHER PUBLICATIONS

Jafri et al. Journal of Immunological Methods, 2001, vol. 251, p. 53-61.*
Labvision, DNA-PKcs Ab-1 datasheet, 2002.*
Chan et al. Genes and Development, vol. 16, p. 2333-2338, 2002.*
Yoshihiko, et al. "Modification of the ionizing radiation response in living cells by an scFv against the DNA-dependent protein kinase", *Nucl. Acids Res.*, vol. 31, No. 20 (2003), pp. 5848-5857.
Autophosphoylation of the DNA-dependent protein kinase catalytic subunit is required for rejoining of DNA double-strand breaks, Chan, et al. (2002).
Cell Cycle Dependence of DNA-dependent Protein Kinase Phosphorylation in Response to DNA Double Strand Breaks, Chen, et al. (2005).
Autophosphorylation of the Catalytic Subunit of the DNA-Dependent Protein Kinase Is Required for efficient End Processing during DNA Double-Strand Break Repair, Ding, et al. (2003).
Geometry of a complex formed by double strand break repair proteins at a single DNA end: recruitment of DNA-PKcs induces inward translocation of Ku protein, Yoo, et al. (1999).
A DNA-Activated Protein Kinase from HeLa ell Nuclei, Carter, et all (1990).
A method to detect particle-specific antibodies against Ku and the DNA-dependent protein kinase catalytic subunit in autoimmune sera, Jafri, et al. (2001).

* cited by examiner

*Primary Examiner*—Eileen B O'Hara
*Assistant Examiner*—Yunsoo Kim
(74) *Attorney, Agent, or Firm*—Fulbright & Jaworski L.L.P.

(57) ABSTRACT

The identification and use of two major DNA-PKcs autophosphorylation sites. Threonine (T) 2609 and Serine (S) 2056, including antibodies specific for phosphorylated T2609 and 52056. Peptides and polynucleotides encoding same, that feature these two sites of phosphorylation. The antibodies do not bind to the unphosphorylated DNA-PKcs protein or peptide, thus providing diagnostic tools to monitor the effectiveness of treatments which target the DNA repair pathway of cancer cells, and the ability to intervene or inhibit in phosphorylation of T2609 or 52056, either through application of a drug or an antibody, to increase the radiosensitivity of cancer cells.

3 Claims, 7 Drawing Sheets

IR, 10 Gy 30min 25-4 monoclonal Ab pS2056Ab

A

B

Time (min): 0  10  30  1h  2h  4h  6h  8h pS2056pA

SEQUENCE LISTING

<160> NUMBER OF SEQ ID NOS: 28

<210> SEQ ID NO 1
<211> LENGTH: 14
<212> TYPE: PRT
<213> ORGANISM: Artificial Sequence
<220> FEATURE:
<221> NAME/KEY: PEPTIDE
<222> LOCATION: (1)..(14)
<223> OTHER INFORMATION: HUMAN GENETIC ORIGIN
<220> FEATURE:
<221> NAME/KEY: MOD_RES
<222> LOCATION: (7)..(7)
<223> OTHER INFORMATION: PHOSPHORYLATION at T2609

<400> SEQUENCE: 1

```
Thr Pro Met Phe Val Glu Thr Gln Ala Ser Gln Gly Thr Cys
1               5                   10
```

<210> SEQ ID NO 2
<211> LENGTH: 14
<212> TYPE: PRT
<213> ORGANISM: Artificial Sequence
<220> FEATURE:
<221> NAME/KEY: PEPTIDE
<222> LOCATION: (1)..(14)
<223> OTHER INFORMATION: HUMAN GENETIC ORIGIN
<220> FEATURE:
<221> NAME/KEY: MOD_RES
<222> LOCATION: (7)..(7)
<223> OTHER INFORMATION: PHOSPHORYLATION at S2056

<400> SEQUENCE: 2

```
Gln Ser Tyr Ser Tyr Ser Ser Gln Asp Pro Arg Pro Ala Cys
1               5                   10
```

<210> SEQ ID NO 3
<211> LENGTH: 4128
<212> TYPE: PRT
<213> ORGANISM: Homo sapiens

<400> SEQUENCE: 3

```
Met Ala Gly Ser Gly Ala Gly Val Arg Cys Ser Leu Leu Arg Leu Gln
1               5                   10                  15

Glu Thr Leu Ser Ala Ala Asp Arg Cys Gly Ala Ala Leu Ala Gly His
                20                  25                  30

Gln Leu Ile Arg Gly Leu Gly Gln Glu Cys Val Leu Ser Ser Ser Pro
            35                  40                  45

Ala Val Leu Ala Leu Gln Thr Ser Leu Val Phe Ser Arg Asp Phe Gly
        50                  55                  60

Leu Leu Val Phe Val Arg Lys Ser Leu Asn Ser Ile Glu Phe Arg Glu
65                  70                  75                  80

Cys Arg Glu Glu Ile Leu Lys Phe Leu Cys Ile Phe Leu Glu Lys Met
                85                  90                  95

Gly Gln Lys Ile Ala Pro Tyr Ser Val Glu Ile Lys Asn Thr Cys Thr
            100                 105                 110

Ser Val Tyr Thr Lys Asp Arg Ala Ala Lys Cys Lys Ile Pro Ala Leu
        115                 120                 125

Asp Leu Leu Ile Lys Leu Leu Gln Thr Phe Arg Ser Ser Arg Leu Met
    130                 135                 140

Asp Glu Phe Lys Ile Gly Glu Leu Phe Ser Lys Phe Tyr Gly Glu Leu
145                 150                 155                 160
```

-continued

Ala Leu Lys Lys Lys Ile Pro Asp Thr Val Leu Glu Lys Val Tyr Glu
            165                 170                 175
Leu Leu Gly Leu Leu Gly Glu Val His Pro Ser Glu Met Ile Asn Asn
        180                 185                 190
Ala Glu Asn Leu Phe Arg Ala Phe Leu Gly Glu Leu Lys Thr Gln Met
    195                 200                 205
Thr Ser Ala Val Arg Glu Pro Lys Leu Pro Val Leu Ala Gly Cys Leu
210                 215                 220
Lys Gly Leu Ser Ser Leu Leu Cys Asn Phe Thr Lys Ser Met Glu Glu
225                 230                 235                 240
Asp Pro Gln Thr Ser Arg Glu Ile Phe Asn Phe Val Leu Lys Ala Ile
            245                 250                 255
Arg Pro Gln Ile Asp Leu Lys Arg Tyr Ala Val Pro Ser Ala Gly Leu
            260                 265                 270
Arg Leu Phe Ala Leu His Ala Ser Gln Phe Ser Thr Cys Leu Leu Asp
        275                 280                 285
Asn Tyr Val Ser Leu Phe Glu Val Leu Leu Lys Trp Cys Ala His Thr
    290                 295                 300
Asn Val Glu Leu Lys Lys Ala Ala Leu Ser Ala Leu Glu Ser Phe Leu
305                 310                 315                 320
Lys Gln Val Ser Asn Met Val Ala Lys Asn Ala Glu Met His Lys Asn
            325                 330                 335
Lys Leu Gln Tyr Phe Met Glu Gln Phe Tyr Gly Ile Ile Arg Asn Val
            340                 345                 350
Asp Ser Asn Asn Lys Glu Leu Ser Ile Ala Ile Arg Gly Tyr Gly Leu
        355                 360                 365
Phe Ala Gly Pro Cys Lys Val Ile Asn Ala Lys Asp Val Asp Phe Met
    370                 375                 380
Tyr Val Glu Leu Ile Gln Arg Cys Lys Gln Met Phe Leu Thr Gln Thr
385                 390                 395                 400
Asp Thr Gly Asp Tyr Arg Val Tyr Gln Met Pro Ser Phe Leu Gln Ser
            405                 410                 415
Val Ala Ser Val Leu Leu Tyr Leu Asp Thr Val Pro Glu Val Tyr Thr
            420                 425                 430
Pro Val Leu Glu His Leu Val Val Met Gln Ile Asp Ser Phe Pro Gln
        435                 440                 445
Tyr Ser Pro Lys Met Gln Leu Val Cys Cys Arg Ala Ile Val Lys Val
    450                 455                 460
Phe Leu Ala Leu Ala Ala Lys Gly Pro Val Leu Arg Asn Cys Ile Ser
465                 470                 475                 480
Thr Val Val His Gln Gly Leu Ile Arg Ile Cys Ser Lys Pro Val Val
            485                 490                 495
Leu Pro Lys Gly Pro Glu Ser Glu Ser Glu Asp His Arg Ala Ser Gly
            500                 505                 510
Glu Val Arg Thr Gly Lys Trp Lys Val Pro Thr Tyr Lys Asp Tyr Val
        515                 520                 525
Asp Leu Phe Arg His Leu Leu Ser Ser Asp Gln Met Met Asp Ser Ile
    530                 535                 540
Leu Ala Asp Glu Ala Phe Phe Ser Val Asn Ser Ser Glu Ser Leu
545                 550                 555                 560
Asn His Leu Leu Tyr Asp Glu Phe Val Lys Ser Val Leu Lys Ile Val
            565                 570                 575

-continued

```
Glu Lys Leu Asp Leu Thr Leu Glu Ile Gln Thr Val Gly Glu Gln Glu
            580                 585                 590

Asn Gly Asp Glu Ala Pro Gly Val Trp Met Ile Pro Thr Ser Asp Pro
            595                 600                 605

Ala Ala Asn Leu His Pro Ala Lys Pro Lys Asp Phe Ser Ala Phe Ile
            610                 615                 620

Asn Leu Val Glu Phe Cys Arg Glu Ile Leu Pro Glu Lys Gln Ala Glu
625                 630                 635                 640

Phe Phe Glu Pro Trp Val Tyr Ser Phe Ser Tyr Glu Leu Ile Leu Gln
                645                 650                 655

Ser Thr Arg Leu Pro Leu Ile Ser Gly Phe Tyr Lys Leu Leu Ser Ile
            660                 665                 670

Thr Val Arg Asn Ala Lys Lys Ile Lys Tyr Phe Glu Gly Val Ser Pro
            675                 680                 685

Lys Ser Leu Lys His Ser Pro Glu Asp Pro Glu Lys Tyr Ser Cys Phe
            690                 695                 700

Ala Leu Phe Val Lys Phe Gly Lys Glu Val Ala Val Lys Met Lys Gln
705                 710                 715                 720

Tyr Lys Asp Glu Leu Leu Ala Ser Cys Leu Thr Phe Leu Leu Ser Leu
                725                 730                 735

Pro His Asn Ile Ile Glu Leu Asp Val Arg Ala Tyr Val Pro Ala Leu
            740                 745                 750

Gln Met Ala Phe Lys Leu Gly Leu Ser Tyr Thr Pro Leu Ala Glu Val
            755                 760                 765

Gly Leu Asn Ala Leu Glu Glu Trp Ser Ile Tyr Ile Asp Arg His Val
            770                 775                 780

Met Gln Pro Tyr Tyr Lys Asp Ile Leu Pro Cys Leu Asp Gly Tyr Leu
785                 790                 795                 800

Lys Thr Ser Ala Leu Ser Asp Glu Thr Lys Asn Asn Trp Glu Val Ser
                805                 810                 815

Ala Leu Ser Arg Ala Ala Gln Lys Gly Phe Asn Lys Val Val Leu Lys
            820                 825                 830

His Leu Lys Lys Thr Lys Asn Leu Ser Ser Asn Glu Ala Ile Ser Leu
            835                 840                 845

Glu Glu Ile Arg Ile Arg Val Val Gln Met Leu Gly Ser Leu Gly Gly
            850                 855                 860

Gln Ile Asn Lys Asn Leu Leu Thr Val Thr Ser Ser Asp Glu Met Met
865                 870                 875                 880

Lys Ser Tyr Val Ala Trp Asp Arg Glu Lys Arg Leu Ser Phe Ala Val
                885                 890                 895

Pro Phe Arg Glu Met Lys Pro Val Ile Phe Leu Asp Val Phe Leu Pro
            900                 905                 910

Arg Val Thr Glu Leu Ala Leu Thr Ala Ser Asp Arg Gln Thr Lys Val
            915                 920                 925

Ala Ala Cys Glu Leu Leu His Ser Met Val Met Phe Met Leu Gly Lys
            930                 935                 940

Ala Thr Gln Met Pro Glu Gly Gly Gln Gly Ala Pro Pro Met Tyr Gln
945                 950                 955                 960

Leu Tyr Lys Arg Thr Phe Pro Val Leu Leu Arg Leu Ala Cys Asp Val
                965                 970                 975

Asp Gln Val Thr Arg Gln Leu Tyr Glu Pro Leu Val Met Gln Leu Ile
            980                 985                 990

His Trp Phe Thr Asn Asn Lys Lys  Phe Glu Ser Gln Asp  Thr Val Ser
```

-continued

|     |     |     |     |     |     |     |     |     |     |     |     |
|-----|-----|-----|-----|-----|-----|-----|-----|-----|-----|-----|-----|
|     |     |     | 995 |     |     | 1000|     |     | 1005|     |     |
| Leu | Leu | Glu | Ala | Ile | Leu | Asp | Gly | Ile | Val | Asp | Pro | Val | Asp | Ser |
| 1010 | | | | 1015 | | | | 1020 | | | |
| Thr | Leu | Arg | Asp | Phe | Cys | Gly | Arg | Cys | Ile | Arg | Glu | Phe | Leu | Lys |
| 1025 | | | | 1030 | | | | 1035 | | | |
| Trp | Ser | Ile | Lys | Gln | Ile | Thr | Pro | Gln | Gln | Glu | Lys | Ser | Pro |
| 1040 | | | | 1045 | | | | 1050 | | | |
| Val | Asn | Thr | Lys | Ser | Leu | Phe | Lys | Arg | Leu | Tyr | Ser | Leu | Ala | Leu |
| 1055 | | | | 1060 | | | | 1065 | | | |
| His | Pro | Asn | Ala | Phe | Lys | Arg | Leu | Gly | Ala | Ser | Leu | Ala | Phe | Asn |
| 1070 | | | | 1075 | | | | 1080 | | | |
| Asn | Ile | Tyr | Arg | Glu | Phe | Arg | Glu | Glu | Glu | Ser | Leu | Val | Glu | Gln |
| 1085 | | | | 1090 | | | | 1095 | | | |
| Phe | Val | Phe | Glu | Ala | Leu | Val | Ile | Tyr | Met | Glu | Ser | Leu | Ala | Leu |
| 1100 | | | | 1105 | | | | 1110 | | | |
| Ala | His | Ala | Asp | Glu | Lys | Ser | Leu | Gly | Thr | Ile | Gln | Gln | Cys | Cys |
| 1115 | | | | 1120 | | | | 1125 | | | |
| Asp | Ala | Ile | Asp | His | Leu | Cys | Arg | Ile | Ile | Glu | Lys | Lys | His | Val |
| 1130 | | | | 1135 | | | | 1140 | | | |
| Ser | Leu | Asn | Lys | Ala | Lys | Lys | Arg | Arg | Leu | Pro | Arg | Gly | Phe | Pro |
| 1145 | | | | 1150 | | | | 1155 | | | |
| Pro | Ser | Ala | Ser | Leu | Cys | Leu | Leu | Asp | Leu | Val | Lys | Trp | Leu | Leu |
| 1160 | | | | 1165 | | | | 1170 | | | |
| Ala | His | Cys | Gly | Arg | Pro | Gln | Thr | Glu | Cys | Arg | His | Lys | Ser | Ile |
| 1175 | | | | 1180 | | | | 1185 | | | |
| Glu | Leu | Phe | Tyr | Lys | Phe | Val | Pro | Leu | Leu | Pro | Gly | Asn | Arg | Ser |
| 1190 | | | | 1195 | | | | 1200 | | | |
| Pro | Asn | Leu | Trp | Leu | Lys | Asp | Val | Leu | Lys | Glu | Glu | Gly | Val | Ser |
| 1205 | | | | 1210 | | | | 1215 | | | |
| Phe | Leu | Ile | Asn | Thr | Phe | Glu | Gly | Gly | Gly | Cys | Gly | Gln | Pro | Ser |
| 1220 | | | | 1225 | | | | 1230 | | | |
| Gly | Ile | Leu | Ala | Gln | Pro | Thr | Leu | Leu | Tyr | Leu | Arg | Gly | Pro | Phe |
| 1235 | | | | 1240 | | | | 1245 | | | |
| Ser | Leu | Gln | Ala | Thr | Leu | Cys | Trp | Leu | Asp | Leu | Leu | Ala | Ala |
| 1250 | | | | 1255 | | | | 1260 | | | |
| Leu | Glu | Cys | Tyr | Asn | Thr | Phe | Ile | Gly | Glu | Arg | Thr | Val | Gly | Ala |
| 1265 | | | | 1270 | | | | 1275 | | | |
| Leu | Gln | Val | Leu | Gly | Thr | Glu | Ala | Gln | Ser | Ser | Leu | Leu | Lys | Ala |
| 1280 | | | | 1285 | | | | 1290 | | | |
| Val | Ala | Phe | Phe | Leu | Glu | Ser | Ile | Ala | Met | His | Asp | Ile | Ile | Ala |
| 1295 | | | | 1300 | | | | 1305 | | | |
| Ala | Glu | Lys | Cys | Phe | Gly | Thr | Gly | Ala | Ala | Gly | Asn | Arg | Thr | Ser |
| 1310 | | | | 1315 | | | | 1320 | | | |
| Pro | Gln | Glu | Gly | Glu | Arg | Tyr | Asn | Tyr | Ser | Lys | Cys | Thr | Val | Val |
| 1325 | | | | 1330 | | | | 1335 | | | |
| Val | Arg | Ile | Met | Glu | Phe | Thr | Thr | Thr | Leu | Leu | Asn | Thr | Ser | Pro |
| 1340 | | | | 1345 | | | | 1350 | | | |
| Glu | Gly | Trp | Lys | Leu | Leu | Lys | Lys | Asp | Leu | Cys | Asn | Thr | His | Leu |
| 1355 | | | | 1360 | | | | 1365 | | | |
| Met | Arg | Val | Leu | Val | Gln | Thr | Leu | Cys | Glu | Pro | Ala | Ser | Ile | Gly |
| 1370 | | | | 1375 | | | | 1380 | | | |
| Phe | Asn | Ile | Gly | Asp | Val | Gln | Val | Met | Ala | His | Leu | Pro | Asp | Val |
| 1385 | | | | 1390 | | | | 1395 | | | |

-continued

```
Cys Val Asn Leu Met Lys Ala Leu Lys Met Ser Pro Tyr Lys Asp
    1400            1405            1410

Ile Leu Glu Thr His Leu Arg Glu Lys Ile Thr Ala Gln Ser Ile
    1415            1420            1425

Glu Glu Leu Cys Ala Val Asn Leu Tyr Gly Pro Asp Ala Gln Val
    1430            1435            1440

Asp Arg Ser Arg Leu Ala Ala Val Val Ser Ala Cys Lys Gln Leu
    1445            1450            1455

His Arg Ala Gly Leu Leu His Asn Ile Leu Pro Ser Gln Ser Thr
    1460            1465            1470

Asp Leu His His Ser Val Gly Thr Glu Leu Leu Ser Leu Val Tyr
    1475            1480            1485

Lys Gly Ile Ala Pro Gly Asp Glu Arg Gln Cys Leu Pro Ser Leu
    1490            1495            1500

Asp Leu Ser Cys Lys Gln Leu Ala Ser Gly Leu Leu Glu Leu Ala
    1505            1510            1515

Phe Ala Phe Gly Gly Leu Cys Glu Arg Leu Val Ser Leu Leu Leu
    1520            1525            1530

Asn Pro Ala Val Leu Ser Thr Ala Ser Leu Gly Ser Ser Gln Gly
    1535            1540            1545

Ser Val Ile His Phe Ser His Gly Glu Tyr Phe Tyr Ser Leu Phe
    1550            1555            1560

Ser Glu Thr Ile Asn Thr Glu Leu Leu Lys Asn Leu Asp Leu Ala
    1565            1570            1575

Val Leu Glu Leu Met Gln Ser Ser Val Asp Asn Thr Lys Met Val
    1580            1585            1590

Ser Ala Val Leu Asn Gly Met Leu Asp Gln Ser Phe Arg Glu Arg
    1595            1600            1605

Ala Asn Gln Lys His Gln Gly Leu Lys Leu Ala Thr Thr Ile Leu
    1610            1615            1620

Gln His Trp Lys Lys Cys Asp Ser Trp Trp Ala Lys Asp Ser Pro
    1625            1630            1635

Leu Glu Thr Lys Met Ala Val Leu Ala Leu Leu Ala Lys Ile Leu
    1640            1645            1650

Gln Ile Asp Ser Ser Val Ser Phe Asn Thr Ser His Gly Ser Phe
    1655            1660            1665

Pro Glu Val Phe Thr Thr Tyr Ile Ser Leu Leu Ala Asp Thr Lys
    1670            1675            1680

Leu Asp Leu His Leu Lys Gly Gln Ala Val Thr Leu Leu Pro Phe
    1685            1690            1695

Phe Thr Ser Leu Thr Gly Gly Ser Leu Glu Glu Leu Arg Arg Val
    1700            1705            1710

Leu Glu Gln Leu Ile Val Ala His Phe Pro Met Gln Ser Arg Glu
    1715            1720            1725

Phe Pro Pro Gly Thr Pro Arg Phe Asn Asn Tyr Val Asp Cys Met
    1730            1735            1740

Lys Lys Phe Leu Asp Ala Leu Glu Leu Ser Gln Ser Pro Met Leu
    1745            1750            1755

Leu Glu Leu Met Thr Glu Val Leu Cys Arg Glu Gln Gln His Val
    1760            1765            1770

Met Glu Glu Leu Phe Gln Ser Ser Phe Arg Arg Ile Ala Arg Arg
    1775            1780            1785
```

-continued

```
Gly Ser Cys Val Thr Gln Val Gly Leu Leu Glu Ser Val Tyr Glu
    1790            1795                1800

Met Phe Arg Lys Asp Asp Pro Arg Leu Ser Phe Thr Arg Gln Ser
    1805            1810                1815

Phe Val Asp Arg Ser Leu Leu Thr Leu Leu Trp His Cys Ser Leu
    1820            1825                1830

Asp Ala Leu Arg Glu Phe Phe Ser Thr Ile Val Val Asp Ala Ile
    1835            1840                1845

Asp Val Leu Lys Ser Arg Phe Thr Lys Leu Asn Glu Ser Thr Phe
    1850            1855                1860

Asp Thr Gln Ile Thr Lys Lys Met Gly Tyr Tyr Lys Ile Leu Asp
    1865            1870                1875

Val Met Tyr Ser Arg Leu Pro Lys Asp Asp Val His Ala Lys Glu
    1880            1885                1890

Ser Lys Ile Asn Gln Val Phe His Gly Ser Cys Ile Thr Glu Gly
    1895            1900                1905

Asn Glu Leu Thr Lys Thr Leu Ile Lys Leu Cys Tyr Asp Ala Phe
    1910            1915                1920

Thr Glu Asn Met Ala Gly Glu Asn Gln Leu Leu Glu Arg Arg Arg
    1925            1930                1935

Leu Tyr His Cys Ala Ala Tyr Asn Cys Ala Ile Ser Val Ile Cys
    1940            1945                1950

Cys Val Phe Asn Glu Leu Lys Phe Tyr Gln Gly Phe Leu Phe Ser
    1955            1960                1965

Glu Lys Pro Glu Lys Asn Leu Leu Ile Phe Glu Asn Leu Ile Asp
    1970            1975                1980

Leu Lys Arg Arg Tyr Asn Phe Pro Val Glu Val Glu Val Pro Met
    1985            1990                1995

Glu Arg Lys Lys Lys Tyr Ile Glu Ile Arg Lys Glu Ala Arg Glu
    2000            2005                2010

Ala Ala Asn Gly Asp Ser Asp Gly Pro Ser Tyr Met Ser Ser Leu
    2015            2020                2025

Ser Tyr Leu Ala Asp Ser Thr Leu Ser Glu Glu Met Ser Gln Phe
    2030            2035                2040

Asp Phe Ser Thr Gly Val Gln Ser Tyr Ser Tyr Ser Ser Gln Asp
    2045            2050                2055

Pro Arg Pro Ala Thr Gly Arg Phe Arg Arg Glu Gln Arg Asp
    2060            2065                2070

Pro Thr Val His Asp Asp Val Leu Glu Leu Glu Met Asp Glu Leu
    2075            2080                2085

Asn Arg His Glu Cys Met Ala Pro Leu Thr Ala Leu Val Lys His
    2090            2095                2100

Met His Arg Ser Leu Gly Pro Pro Gln Gly Glu Glu Asp Ser Val
    2105            2110                2115

Pro Arg Asp Leu Pro Ser Trp Met Lys Phe Leu His Gly Lys Leu
    2120            2125                2130

Gly Asn Pro Ile Val Pro Leu Asn Ile Arg Leu Phe Leu Ala Lys
    2135            2140                2145

Leu Val Ile Asn Thr Glu Glu Val Phe Arg Pro Tyr Ala Lys His
    2150            2155                2160

Trp Leu Ser Pro Leu Leu Gln Leu Ala Ala Ser Glu Asn Asn Gly
    2165            2170                2175

Gly Glu Gly Ile His Tyr Met Val Val Glu Ile Val Ala Thr Ile
```

-continued

```
             2180               2185              2190
Leu Ser Trp Thr Gly Leu Ala Thr Pro Thr Gly Val Pro Lys Asp
    2195               2200              2205

Glu Val Leu Ala Asn Arg Leu Leu Asn Phe Leu Met Lys His Val
    2210               2215              2220

Phe His Pro Lys Arg Ala Val Phe Arg His Asn Leu Glu Ile Ile
    2225               2230              2235

Lys Thr Leu Val Glu Cys Trp Lys Asp Cys Leu Ser Ile Pro Tyr
    2240               2245              2250

Arg Leu Ile Phe Glu Lys Phe Ser Gly Lys Asp Pro Asn Ser Lys
    2255               2260              2265

Asp Asn Ser Val Gly Ile Gln Leu Leu Gly Ile Val Met Ala Asn
    2270               2275              2280

Asp Leu Pro Pro Tyr Asp Pro Gln Cys Gly Ile Gln Ser Ser Glu
    2285               2290              2295

Tyr Phe Gln Ala Leu Val Asn Asn Met Ser Phe Val Arg Tyr Lys
    2300               2305              2310

Glu Val Tyr Ala Ala Ala Glu Val Leu Gly Leu Ile Leu Arg
    2315               2320              2325

Tyr Val Met Glu Arg Lys Asn Ile Leu Glu Glu Ser Leu Cys Glu
    2330               2335              2340

Leu Val Ala Lys Gln Leu Lys Gln His Gln Asn Thr Met Glu Asp
    2345               2350              2355

Lys Phe Ile Val Cys Leu Asn Lys Val Thr Lys Ser Phe Pro Pro
    2360               2365              2370

Leu Ala Asp Arg Phe Met Asn Ala Val Phe Phe Leu Leu Pro Lys
    2375               2380              2385

Phe His Gly Val Leu Lys Thr Leu Cys Leu Glu Val Val Leu Cys
    2390               2395              2400

Arg Val Glu Gly Met Thr Glu Leu Tyr Phe Gln Leu Lys Ser Lys
    2405               2410              2415

Asp Phe Val Gln Val Met Arg His Arg Asp Asp Glu Arg Gln Lys
    2420               2425              2430

Val Cys Leu Asp Ile Ile Tyr Lys Met Met Pro Lys Leu Lys Pro
    2435               2440              2445

Val Glu Leu Arg Glu Leu Leu Asn Pro Val Val Glu Phe Val Ser
    2450               2455              2460

His Pro Ser Thr Thr Cys Arg Glu Gln Met Tyr Asn Ile Leu Met
    2465               2470              2475

Trp Ile His Asp Asn Tyr Arg Asp Pro Glu Ser Glu Thr Asp Asn
    2480               2485              2490

Asp Ser Gln Glu Ile Phe Lys Leu Ala Lys Asp Val Leu Ile Gln
    2495               2500              2505

Gly Leu Ile Asp Glu Asn Pro Gly Leu Gln Leu Ile Ile Arg Asn
    2510               2515              2520

Phe Trp Ser His Glu Thr Arg Leu Pro Ser Asn Thr Leu Asp Arg
    2525               2530              2535

Leu Leu Ala Leu Asn Ser Leu Tyr Ser Pro Lys Ile Glu Val His
    2540               2545              2550

Phe Leu Ser Leu Ala Thr Asn Phe Leu Leu Glu Met Thr Ser Met
    2555               2560              2565

Ser Pro Asp Tyr Pro Asn Pro Met Phe Glu His Pro Leu Ser Glu
    2570               2575              2580
```

```
Cys Glu Phe Gln Glu Tyr Thr Ile Asp Ser Asp Trp Arg Phe Arg
    2585                2590                2595

Ser Thr Val Leu Thr Pro Met Phe Val Glu Thr Gln Ala Ser Gln
    2600                2605                2610

Gly Thr Leu Gln Thr Arg Thr Gln Glu Gly Ser Leu Ser Ala Arg
    2615                2620                2625

Trp Pro Val Ala Gly Gln Ile Arg Ala Thr Gln Gln His Asp
    2630                2635                2640

Phe Thr Leu Thr Gln Thr Ala Asp Gly Arg Ser Ser Phe Asp Trp
    2645                2650                2655

Leu Thr Gly Ser Ser Thr Asp Pro Leu Val Asp His Thr Ser Pro
    2660                2665                2670

Ser Ser Asp Ser Leu Leu Phe Ala His Lys Arg Ser Glu Arg Leu
    2675                2680                2685

Gln Arg Ala Pro Leu Lys Ser Val Gly Pro Asp Phe Gly Lys Lys
    2690                2695                2700

Arg Leu Gly Leu Pro Gly Asp Glu Val Asp Asn Lys Val Lys Gly
    2705                2710                2715

Ala Ala Gly Arg Thr Asp Leu Leu Arg Leu Arg Arg Phe Met
    2720                2725                2730

Arg Asp Gln Glu Lys Leu Ser Leu Met Tyr Ala Arg Lys Gly Val
    2735                2740                2745

Ala Glu Gln Lys Arg Glu Lys Glu Ile Lys Ser Glu Leu Lys Met
    2750                2755                2760

Lys Gln Asp Ala Gln Val Val Leu Tyr Arg Ser Tyr Arg His Gly
    2765                2770                2775

Asp Leu Pro Asp Ile Gln Ile Lys His Ser Ser Leu Ile Thr Pro
    2780                2785                2790

Leu Gln Ala Val Ala Gln Arg Asp Pro Ile Ile Ala Lys Gln Leu
    2795                2800                2805

Phe Ser Ser Leu Phe Ser Gly Ile Leu Lys Glu Met Asp Lys Phe
    2810                2815                2820

Lys Thr Leu Ser Glu Lys Asn Asn Ile Thr Gln Lys Leu Leu Gln
    2825                2830                2835

Asp Phe Asn Arg Phe Leu Asn Thr Thr Phe Ser Phe Phe Pro Pro
    2840                2845                2850

Phe Val Ser Cys Ile Gln Asp Ile Ser Cys Gln His Ala Ala Leu
    2855                2860                2865

Leu Ser Leu Asp Pro Ala Ala Val Ser Ala Gly Cys Leu Ala Ser
    2870                2875                2880

Leu Gln Gln Pro Val Gly Ile Arg Leu Leu Glu Glu Ala Leu Leu
    2885                2890                2895

Arg Leu Leu Pro Ala Glu Leu Pro Ala Lys Arg Val Arg Gly Lys
    2900                2905                2910

Ala Arg Leu Pro Pro Asp Val Leu Arg Trp Val Glu Leu Ala Lys
    2915                2920                2925

Leu Tyr Arg Ser Ile Gly Glu Tyr Asp Val Leu Arg Gly Ile Phe
    2930                2935                2940

Thr Ser Glu Ile Gly Thr Lys Gln Ile Thr Gln Ser Ala Leu Leu
    2945                2950                2955

Ala Glu Ala Arg Ser Asp Tyr Ser Glu Ala Ala Lys Gln Tyr Asp
    2960                2965                2970
```

-continued

```
Glu Ala Leu Asn Lys Gln Asp Trp Val Asp Gly Glu Pro Thr Glu
    2975                2980                2985
Ala Glu Lys Asp Phe Trp Glu Leu Ala Ser Leu Asp Cys Tyr Asn
    2990                2995                3000
His Leu Ala Glu Trp Lys Ser Leu Glu Tyr Cys Ser Thr Ala Ser
    3005                3010                3015
Ile Asp Ser Glu Asn Pro Pro Asp Leu Asn Lys Ile Trp Ser Glu
    3020                3025                3030
Pro Phe Tyr Gln Glu Thr Tyr Leu Pro Tyr Met Ile Arg Ser Lys
    3035                3040                3045
Leu Lys Leu Leu Leu Gln Gly Glu Ala Asp Gln Ser Leu Leu Thr
    3050                3055                3060
Phe Ile Asp Lys Ala Met His Gly Glu Leu Gln Lys Ala Ile Leu
    3065                3070                3075
Glu Leu His Tyr Ser Gln Glu Leu Ser Leu Leu Tyr Leu Leu Gln
    3080                3085                3090
Asp Asp Val Asp Arg Ala Lys Tyr Tyr Ile Gln Asn Gly Ile Gln
    3095                3100                3105
Ser Phe Met Gln Asn Tyr Ser Ser Ile Asp Val Leu Leu His Gln
    3110                3115                3120
Ser Arg Leu Thr Lys Leu Gln Ser Val Gln Ala Leu Thr Glu Ile
    3125                3130                3135
Gln Glu Phe Ile Ser Phe Ile Ser Lys Gln Gly Asn Leu Ser Ser
    3140                3145                3150
Gln Val Pro Leu Lys Arg Leu Leu Asn Thr Trp Thr Asn Arg Tyr
    3155                3160                3165
Pro Asp Ala Lys Met Asp Pro Met Asn Ile Trp Asp Asp Ile Ile
    3170                3175                3180
Thr Asn Arg Cys Phe Phe Leu Ser Lys Ile Glu Glu Lys Leu Thr
    3185                3190                3195
Pro Leu Pro Glu Asp Asn Ser Met Asn Val Asp Gln Asp Gly Asp
    3200                3205                3210
Pro Ser Asp Arg Met Glu Val Gln Glu Gln Glu Glu Asp Ile Ser
    3215                3220                3225
Ser Leu Ile Arg Ser Cys Lys Phe Ser Met Lys Met Lys Met Ile
    3230                3235                3240
Asp Ser Ala Arg Lys Gln Asn Asn Phe Ser Leu Ala Met Lys Leu
    3245                3250                3255
Leu Lys Glu Leu His Lys Glu Ser Lys Thr Arg Asp Asp Trp Leu
    3260                3265                3270
Val Ser Trp Val Gln Ser Tyr Cys Arg Leu Ser His Cys Arg Ser
    3275                3280                3285
Arg Ser Gln Gly Cys Ser Glu Gln Val Leu Thr Val Leu Lys Thr
    3290                3295                3300
Val Ser Leu Leu Asp Glu Asn Asn Val Ser Ser Tyr Leu Ser Lys
    3305                3310                3315
Asn Ile Leu Ala Phe Arg Asp Gln Asn Ile Leu Leu Gly Thr Thr
    3320                3325                3330
Tyr Arg Ile Ile Ala Asn Ala Leu Ser Ser Glu Pro Ala Cys Leu
    3335                3340                3345
Ala Glu Ile Glu Glu Asp Lys Ala Arg Arg Ile Leu Glu Leu Ser
    3350                3355                3360
Gly Ser Ser Ser Glu Asp Ser Glu Lys Val Ile Ala Gly Leu Tyr
```

-continued

```
              3365                3370                3375
Gln Arg Ala Phe Gln His Leu Ser Glu Ala Val Gln Ala Ala Glu
        3380                3385                3390
Glu Glu Ala Gln Pro Pro Ser Trp Ser Cys Gly Pro Ala Ala Gly
        3395                3400                3405
Val Ile Asp Ala Tyr Met Thr Leu Ala Asp Phe Cys Asp Gln Gln
        3410                3415                3420
Leu Arg Lys Glu Glu Glu Asn Ala Ser Val Thr Asp Ser Ala Glu
        3425                3430                3435
Leu Gln Ala Tyr Pro Ala Leu Val Val Glu Lys Met Leu Lys Ala
        3440                3445                3450
Leu Lys Leu Asn Ser Asn Glu Ala Arg Leu Lys Phe Pro Arg Leu
        3455                3460                3465
Leu Gln Ile Ile Glu Arg Tyr Pro Glu Glu Thr Leu Ser Leu Met
        3470                3475                3480
Thr Lys Glu Ile Ser Ser Val Pro Cys Trp Gln Phe Ile Ser Trp
        3485                3490                3495
Ile Ser His Met Val Ala Leu Leu Asp Lys Asp Gln Ala Val Ala
        3500                3505                3510
Val Gln His Ser Val Glu Glu Ile Thr Asp Asn Tyr Pro Gln Ala
        3515                3520                3525
Ile Val Tyr Pro Phe Ile Ile Ser Ser Glu Ser Tyr Ser Phe Lys
        3530                3535                3540
Asp Thr Ser Thr Gly His Lys Asn Lys Glu Phe Val Ala Arg Ile
        3545                3550                3555
Lys Ser Lys Leu Asp Gln Gly Gly Val Ile Gln Asp Phe Ile Asn
        3560                3565                3570
Ala Leu Asp Gln Leu Ser Asn Pro Glu Leu Leu Phe Lys Asp Trp
        3575                3580                3585
Ser Asn Asp Val Arg Ala Glu Leu Ala Lys Thr Pro Val Asn Lys
        3590                3595                3600
Lys Asn Ile Glu Lys Met Tyr Glu Arg Met Tyr Ala Ala Leu Gly
        3605                3610                3615
Asp Pro Lys Ala Pro Gly Leu Gly Ala Phe Arg Arg Lys Phe Ile
        3620                3625                3630
Gln Thr Phe Gly Lys Glu Phe Asp Lys His Phe Gly Lys Gly Gly
        3635                3640                3645
Ser Lys Leu Leu Arg Met Lys Leu Ser Asp Phe Asn Asp Ile Thr
        3650                3655                3660
Asn Met Leu Leu Leu Lys Met Asn Lys Asp Ser Lys Pro Pro Gly
        3665                3670                3675
Asn Leu Lys Glu Cys Ser Pro Trp Met Ser Asp Phe Lys Val Glu
        3680                3685                3690
Phe Leu Arg Asn Glu Leu Glu Ile Pro Gly Gln Tyr Asp Gly Arg
        3695                3700                3705
Gly Lys Pro Leu Pro Glu Tyr His Val Arg Ile Ala Gly Phe Asp
        3710                3715                3720
Glu Arg Val Thr Val Met Ala Ser Leu Arg Arg Pro Lys Arg Ile
        3725                3730                3735
Ile Ile Arg Gly His Asp Glu Arg Glu His Pro Phe Leu Val Lys
        3740                3745                3750
Gly Gly Glu Asp Leu Arg Gln Asp Gln Arg Val Glu Gln Leu Phe
        3755                3760                3765
```

```
Gln Val Met Asn Gly Ile Leu Ala Gln Asp Ser Ala Cys Ser Gln
    3770                3775                3780

Arg Ala Leu Gln Leu Arg Thr Tyr Ser Val Val Pro Met Thr Ser
    3785                3790                3795

Arg Leu Gly Leu Ile Glu Trp Leu Glu Asn Thr Val Thr Leu Lys
    3800                3805                3810

Asp Leu Leu Asn Thr Met Ser Gln Glu Glu Lys Ala Ala Tyr
    3815                3820                3825

Leu Ser Asp Pro Arg Ala Pro Pro Cys Glu Tyr Lys Asp Trp Leu
    3830                3835                3840

Thr Lys Met Ser Gly Lys His Asp Val Gly Ala Tyr Met Leu Met
    3845                3850                3855

Tyr Lys Gly Ala Asn Arg Thr Glu Thr Val Thr Ser Phe Arg Lys
    3860                3865                3870

Arg Glu Ser Lys Val Pro Ala Asp Leu Leu Lys Arg Ala Phe Val
    3875                3880                3885

Arg Met Ser Thr Ser Pro Glu Ala Phe Leu Ala Leu Arg Ser His
    3890                3895                3900

Phe Ala Ser Ser His Ala Leu Ile Cys Ile Ser His Trp Ile Leu
    3905                3910                3915

Gly Ile Gly Asp Arg His Leu Asn Asn Phe Met Val Ala Met Glu
    3920                3925                3930

Thr Gly Gly Val Ile Gly Ile Asp Phe Gly His Ala Phe Gly Ser
    3935                3940                3945

Ala Thr Gln Phe Leu Pro Val Pro Glu Leu Met Pro Phe Arg Leu
    3950                3955                3960

Thr Arg Gln Phe Ile Asn Leu Met Leu Pro Met Lys Glu Thr Gly
    3965                3970                3975

Leu Met Tyr Ser Ile Met Val His Ala Leu Arg Ala Phe Arg Ser
    3980                3985                3990

Asp Pro Gly Leu Leu Thr Asn Thr Met Asp Val Phe Val Lys Glu
    3995                4000                4005

Pro Ser Phe Asp Trp Lys Asn Phe Glu Gln Lys Met Leu Lys Lys
    4010                4015                4020

Gly Gly Ser Trp Ile Gln Ile Asn Val Ala Glu Lys Asn Trp
    4025                4030                4035

Tyr Pro Arg Gln Lys Ile Cys Tyr Ala Lys Arg Lys Leu Ala Gly
    4040                4045                4050

Ala Asn Pro Ala Val Ile Thr Cys Asp Glu Leu Leu Leu Gly His
    4055                4060                4065

Glu Lys Ala Pro Ala Phe Arg Asp Tyr Val Ala Val Ala Arg Gly
    4070                4075                4080

Ser Lys Asp His Asn Ile Arg Ala Gln Glu Pro Glu Ser Gly Leu
    4085                4090                4095

Ser Glu Glu Thr Gln Val Lys Cys Leu Met Asp Gln Ala Thr Asp
    4100                4105                4110

Pro Asn Ile Leu Gly Arg Thr Trp Glu Gly Trp Glu Pro Trp Met
    4115                4120                4125

<210> SEQ ID NO 4
<211> LENGTH: 21
<212> TYPE: PRT
<213> ORGANISM: Artificial Sequence
<220> FEATURE:
```

```
<221> NAME/KEY: PEPTIDE
<222> LOCATION: (1)..(21)
<223> OTHER INFORMATION: HUMAN GENETIC ORIGIN
<220> FEATURE:
<221> NAME/KEY: MOD_RES
<222> LOCATION: (11)..(11)
<223> OTHER INFORMATION: PHOSPHORYLATION at T2609

<400> SEQUENCE: 4

Ser Thr Val Leu Thr Pro Met Phe Val Glu Thr Gln Ala Ser Gln Gly
 1               5                  10                  15

Thr Leu Gln Thr Arg
            20

<210> SEQ ID NO 5
<211> LENGTH: 29
<212> TYPE: PRT
<213> ORGANISM: Artificial Sequence
<220> FEATURE:
<221> NAME/KEY: PEPTIDE
<222> LOCATION: (1)..(29)
<223> OTHER INFORMATION: HUMAN GENETIC ORIGIN
<220> FEATURE:
<221> NAME/KEY: MOD_RES
<222> LOCATION: (13)..(13)
<223> OTHER INFORMATION: PHOSPHORYLATION at S2056

<400> SEQUENCE: 5

Asp Phe Ser Thr Gly Val Gln Ser Tyr Ser Tyr Ser Ser Gln Asp Pro
 1               5                  10                  15

Arg Pro Ala Thr Gly Arg Phe Arg Arg Glu Gln Arg
            20                  25

<210> SEQ ID NO 6
<211> LENGTH: 303
<212> TYPE: PRT
<213> ORGANISM: Artificial Sequence
<220> FEATURE:
<221> NAME/KEY: PEPTIDE
<222> LOCATION: (1)..(303)
<223> OTHER INFORMATION: HUMAN GENETIC ORIGIN
<220> FEATURE:
<221> NAME/KEY: MOD_RES
<222> LOCATION: (177)..(177)
<223> OTHER INFORMATION: PHOSPHORYLATION at S2056

<400> SEQUENCE: 6

Met Tyr Ser Arg Leu Pro Lys Asp Asp Val His Ala Lys Glu Ser Lys
 1               5                  10                  15

Ile Asn Gln Val Phe His Gly Ser Cys Ile Thr Glu Gly Asn Glu Leu
            20                  25                  30

Thr Lys Thr Leu Ile Lys Leu Cys Tyr Asp Ala Phe Thr Glu Asn Met
        35                  40                  45

Ala Gly Glu Asn Gln Leu Leu Glu Arg Arg Arg Leu Tyr His Cys Ala
    50                  55                  60

Ala Tyr Asn Cys Ala Ile Ser Val Ile Cys Cys Val Phe Asn Glu Leu
65                  70                  75                  80

Lys Phe Tyr Gln Gly Phe Leu Phe Ser Glu Lys Pro Glu Lys Asn Leu
                85                  90                  95

Leu Ile Phe Glu Asn Leu Ile Asp Leu Lys Arg Arg Tyr Asn Phe Pro
            100                 105                 110

Val Glu Val Glu Val Pro Met Glu Arg Lys Lys Lys Tyr Ile Glu Ile
        115                 120                 125

Arg Lys Glu Ala Arg Glu Ala Ala Asn Gly Asp Ser Asp Gly Pro Ser
```

-continued

```
                130                 135                 140
Tyr Met Ser Ser Leu Ser Tyr Leu Ala Asp Ser Thr Leu Ser Glu Glu
145                 150                 155                 160

Met Ser Gln Phe Asp Phe Ser Thr Gly Val Gln Ser Tyr Ser Tyr Ser
                165                 170                 175

Ser Gln Asp Pro Arg Pro Ala Thr Gly Arg Phe Arg Arg Arg Glu Gln
            180                 185                 190

Arg Asp Pro Thr Val His Asp Val Leu Glu Leu Glu Met Asp Glu
        195                 200                 205

Leu Asn Arg His Glu Cys Met Ala Pro Leu Thr Ala Leu Val Lys His
    210                 215                 220

Met His Arg Ser Leu Gly Pro Pro Gln Gly Glu Glu Asp Ser Val Pro
225                 230                 235                 240

Arg Asp Leu Pro Ser Trp Met Lys Phe Leu His Gly Lys Leu Gly Asn
                245                 250                 255

Pro Ile Val Pro Leu Asn Ile Arg Leu Phe Leu Ala Lys Leu Val Ile
            260                 265                 270

Asn Thr Glu Glu Val Phe Arg Pro Tyr Ala Lys His Trp Leu Ser Pro
        275                 280                 285

Leu Leu Gln Leu Ala Ala Ser Glu Asn Asn Gly Gly Glu Gly Ile
    290                 295                 300
```

<210> SEQ ID NO 7
<211> LENGTH: 388
<212> TYPE: PRT
<213> ORGANISM: Artificial Sequence
<220> FEATURE:
<221> NAME/KEY: PEPTIDE
<222> LOCATION: (1)..(388)
<223> OTHER INFORMATION: HUMAN GENETIC ORIGIN
<220> FEATURE:
<221> NAME/KEY: MOD_RES
<222> LOCATION: (177)..(177)
<223> OTHER INFORMATION: PHOSPHORYLATION at S2056

<400> SEQUENCE: 7

```
Met Tyr Ser Arg Leu Pro Lys Asp Asp Val His Ala Lys Glu Ser Lys
1               5                   10                  15

Ile Asn Gln Val Phe His Gly Ser Cys Ile Thr Glu Gly Asn Glu Leu
            20                  25                  30

Thr Lys Thr Leu Ile Lys Leu Cys Tyr Asp Ala Phe Thr Glu Asn Met
        35                  40                  45

Ala Gly Glu Asn Gln Leu Leu Glu Arg Arg Arg Leu Tyr His Cys Ala
    50                  55                  60

Ala Tyr Asn Cys Ala Ile Ser Val Ile Cys Cys Val Phe Asn Glu Leu
65                  70                  75                  80

Lys Phe Tyr Gln Gly Phe Leu Phe Ser Glu Lys Pro Glu Lys Asn Leu
                85                  90                  95

Leu Ile Phe Glu Asn Leu Ile Asp Leu Lys Arg Arg Tyr Asn Phe Pro
            100                 105                 110

Val Glu Val Glu Val Pro Met Glu Arg Lys Lys Lys Tyr Ile Glu Ile
        115                 120                 125

Arg Lys Glu Ala Arg Glu Ala Ala Asn Gly Asp Ser Asp Gly Pro Ser
    130                 135                 140

Tyr Met Ser Ser Leu Ser Tyr Leu Ala Asp Ser Thr Leu Ser Glu Glu
145                 150                 155                 160

Met Ser Gln Phe Asp Phe Ser Thr Gly Val Gln Ser Tyr Ser Tyr Ser
```

-continued

```
            165                 170                 175
Ser Gln Asp Pro Arg Pro Ala Thr Gly Arg Phe Arg Arg Glu Gln
            180                 185                 190

Arg Asp Pro Thr Val His Asp Val Leu Glu Leu Glu Met Asp Glu
            195                 200                 205

Leu Asn Arg His Glu Cys Met Ala Pro Leu Thr Ala Leu Val Lys His
    210                 215                 220

Met His Arg Ser Leu Gly Pro Pro Gln Gly Glu Asp Ser Val Pro
225                 230                 235                 240

Arg Asp Leu Pro Ser Trp Met Lys Phe Leu His Gly Lys Leu Gly Asn
                245                 250                 255

Pro Ile Val Pro Leu Asn Ile Arg Leu Phe Leu Ala Lys Leu Val Ile
            260                 265                 270

Asn Thr Glu Glu Val Phe Arg Pro Tyr Ala Lys His Trp Leu Ser Pro
            275                 280                 285

Leu Leu Gln Leu Ala Ala Ser Glu Asn Asn Gly Gly Glu Gly Ile His
            290                 295                 300

Tyr Met Val Val Glu Ile Val Ala Thr Ile Leu Ser Trp Thr Gly Leu
305                 310                 315                 320

Ala Thr Pro Thr Gly Val Pro Lys Asp Glu Val Leu Ala Asn Arg Leu
                325                 330                 335

Leu Asn Phe Leu Met Lys His Val Phe His Pro Lys Arg Ala Val Phe
            340                 345                 350

Arg His Asn Leu Glu Ile Ile Lys Thr Leu Val Glu Cys Trp Lys Asp
            355                 360                 365

Cys Leu Ser Ile Pro Tyr Arg Leu Ile Phe Glu Lys Phe Ser Gly Lys
    370                 375                 380

Asp Pro Asn Ser
385

<210> SEQ ID NO 8
<211> LENGTH: 821
<212> TYPE: PRT
<213> ORGANISM: Artificial Sequence
<220> FEATURE:
<221> NAME/KEY: PEPTIDE
<222> LOCATION: (1)..(821)
<223> OTHER INFORMATION: HUMAN GENETIC ORIGIN
<220> FEATURE:
<221> NAME/KEY: MOD_RES
<222> LOCATION: (177)..(177)
<223> OTHER INFORMATION: PHOSPHORYLATION at S2056
<220> FEATURE:
<221> NAME/KEY: MOD_RES
<222> LOCATION: (730)..(730)
<223> OTHER INFORMATION: PHOSPHORYLATION at T2609

<400> SEQUENCE: 8

Met Tyr Ser Arg Leu Pro Lys Asp Asp Val His Ala Lys Glu Ser Lys
1               5                   10                  15

Ile Asn Gln Val Phe His Gly Ser Cys Ile Thr Glu Gly Asn Glu Leu
            20                  25                  30

Thr Lys Thr Leu Ile Lys Leu Cys Tyr Asp Ala Phe Thr Glu Asn Met
        35                  40                  45

Ala Gly Glu Asn Gln Leu Leu Glu Arg Arg Arg Leu Tyr His Cys Ala
    50                  55                  60

Ala Tyr Asn Cys Ala Ile Ser Val Ile Cys Cys Val Phe Asn Glu Leu
65                  70                  75                  80
```

-continued

```
Lys Phe Tyr Gln Gly Phe Leu Phe Ser Glu Lys Pro Glu Lys Asn Leu
                85                  90                  95

Leu Ile Phe Glu Asn Leu Ile Asp Leu Lys Arg Arg Tyr Asn Phe Pro
                100                 105                 110

Val Glu Val Glu Val Pro Met Glu Arg Lys Lys Tyr Ile Glu Ile
            115                 120                 125

Arg Lys Glu Ala Arg Glu Ala Ala Asn Gly Asp Ser Asp Gly Pro Ser
130                 135                 140

Tyr Met Ser Ser Leu Ser Tyr Leu Ala Asp Ser Thr Leu Ser Glu Glu
145                 150                 155                 160

Met Ser Gln Phe Asp Phe Ser Thr Gly Val Gln Ser Tyr Ser Tyr Ser
                165                 170                 175

Ser Gln Asp Pro Arg Pro Ala Thr Gly Arg Phe Arg Arg Glu Gln
                180                 185                 190

Arg Asp Pro Thr Val His Asp Val Leu Glu Leu Glu Met Asp Glu
        195                 200                 205

Leu Asn Arg His Glu Cys Met Ala Pro Leu Thr Ala Leu Val Lys His
        210                 215                 220

Met His Arg Ser Leu Gly Pro Pro Gln Gly Glu Asp Ser Val Pro
225                 230                 235                 240

Arg Asp Leu Pro Ser Trp Met Lys Phe Leu His Gly Lys Leu Gly Asn
                245                 250                 255

Pro Ile Val Pro Leu Asn Ile Arg Leu Phe Leu Ala Lys Leu Val Ile
                260                 265                 270

Asn Thr Glu Glu Val Phe Arg Pro Tyr Ala Lys His Trp Leu Ser Pro
            275                 280                 285

Leu Leu Gln Leu Ala Ala Ser Glu Asn Gly Gly Glu Gly Ile His
        290                 295                 300

Tyr Met Val Val Glu Ile Val Ala Thr Ile Leu Ser Trp Thr Gly Leu
305                 310                 315                 320

Ala Thr Pro Thr Gly Val Pro Lys Asp Glu Val Leu Ala Asn Arg Leu
                325                 330                 335

Leu Asn Phe Leu Met Lys His Val Phe His Pro Lys Arg Ala Val Phe
                340                 345                 350

Arg His Asn Leu Glu Ile Ile Lys Thr Leu Val Glu Cys Trp Lys Asp
            355                 360                 365

Cys Leu Ser Ile Pro Tyr Arg Leu Ile Phe Glu Lys Phe Ser Gly Lys
        370                 375                 380

Asp Pro Asn Ser Lys Asp Asn Ser Val Gly Ile Gln Leu Leu Gly Ile
385                 390                 395                 400

Val Met Ala Asn Asp Leu Pro Pro Tyr Asp Pro Gln Cys Gly Ile Gln
                405                 410                 415

Ser Ser Glu Tyr Phe Gln Ala Leu Val Asn Asn Met Ser Phe Val Arg
            420                 425                 430

Tyr Lys Glu Val Tyr Ala Ala Ala Glu Val Leu Gly Leu Ile Leu
        435                 440                 445

Arg Tyr Val Met Glu Arg Lys Asn Ile Leu Glu Glu Ser Leu Cys Glu
        450                 455                 460

Leu Val Ala Lys Gln Leu Lys Gln His Gln Asn Thr Met Glu Asp Lys
465                 470                 475                 480

Phe Ile Val Cys Leu Asn Lys Val Thr Lys Ser Phe Pro Pro Leu Ala
                485                 490                 495

Asp Arg Phe Met Asn Ala Val Phe Phe Leu Leu Pro Lys Phe His Gly
```

-continued

```
                500                 505                 510
Val Leu Lys Thr Leu Cys Leu Glu Val Val Leu Cys Arg Val Glu Gly
            515                 520                 525

Met Thr Glu Leu Tyr Phe Gln Leu Lys Ser Lys Asp Phe Val Gln Val
530                 535                 540

Met Arg His Arg Asp Asp Glu Arg Gln Lys Val Cys Leu Asp Ile Ile
545                 550                 555                 560

Tyr Lys Met Met Pro Lys Leu Lys Pro Val Glu Leu Arg Glu Leu Leu
                565                 570                 575

Asn Pro Val Val Glu Phe Val Ser His Pro Ser Thr Thr Cys Arg Glu
            580                 585                 590

Gln Met Tyr Asn Ile Leu Met Trp Ile His Asp Asn Tyr Arg Asp Pro
            595                 600                 605

Glu Ser Glu Thr Asp Asn Asp Ser Gln Glu Ile Phe Lys Leu Ala Lys
            610                 615                 620

Asp Val Leu Ile Gln Gly Leu Ile Asp Glu Asn Pro Gly Leu Gln Leu
625                 630                 635                 640

Ile Ile Arg Asn Phe Trp Ser His Glu Thr Arg Leu Pro Ser Asn Thr
                645                 650                 655

Leu Asp Arg Leu Leu Ala Leu Asn Ser Leu Tyr Ser Pro Lys Ile Glu
            660                 665                 670

Val His Phe Leu Ser Leu Ala Thr Asn Phe Leu Leu Glu Met Thr Ser
            675                 680                 685

Met Ser Pro Asp Tyr Pro Asn Pro Met Phe Glu His Pro Leu Ser Glu
690                 695                 700

Cys Glu Phe Gln Glu Tyr Thr Ile Asp Ser Asp Trp Arg Phe Arg Ser
705                 710                 715                 720

Thr Val Leu Thr Pro Met Phe Val Glu Thr Gln Ala Ser Gln Gly Thr
                725                 730                 735

Leu Gln Thr Arg Thr Gln Glu Gly Ser Leu Ser Ala Arg Trp Pro Val
            740                 745                 750

Ala Gly Gln Ile Arg Ala Thr Gln Gln His Asp Phe Thr Leu Thr
            755                 760                 765

Gln Thr Ala Asp Gly Arg Ser Ser Phe Asp Trp Leu Thr Gly Ser Ser
770                 775                 780

Thr Asp Pro Leu Val Asp His Thr Ser Pro Ser Ser Asp Ser Leu Leu
785                 790                 795                 800

Phe Ala His Lys Arg Ser Glu Arg Leu Gln Arg Ala Pro Leu Lys Ser
                805                 810                 815

Val Gly Pro Asp Phe
            820

<210> SEQ ID NO 9
<211> LENGTH: 440
<212> TYPE: PRT
<213> ORGANISM: Artificial Sequence
<220> FEATURE:
<221> NAME/KEY: PEPTIDE
<222> LOCATION: (1)..(440)
<223> OTHER INFORMATION: HUMAN GENETIC ORIGIN
<220> FEATURE:
<221> NAME/KEY: MOD_RES
<222> LOCATION: (349)..(349)
<223> OTHER INFORMATION: PHOSPHORYLATION at T2609

<400> SEQUENCE: 9

Ser Gly Lys Asp Pro Asn Ser Lys Asp Asn Ser Val Gly Ile Gln Leu
```

```
1               5                    10                   15
Leu Gly Ile Val Met Ala Asn Asp Leu Pro Tyr Asp Pro Gln Cys
            20                  25                  30

Gly Ile Gln Ser Ser Glu Tyr Phe Gln Ala Leu Val Asn Asn Met Ser
            35                  40                  45

Phe Val Arg Tyr Lys Glu Val Tyr Ala Ala Ala Glu Val Leu Gly
            50                  55                  60

Leu Ile Leu Arg Tyr Val Met Glu Arg Lys Asn Ile Leu Glu Glu Ser
65                  70                  75                  80

Leu Cys Glu Leu Val Ala Lys Gln Leu Lys Gln His Gln Asn Thr Met
                    85                  90                  95

Glu Asp Lys Phe Ile Val Cys Leu Asn Lys Val Thr Lys Ser Phe Pro
                    100                 105                 110

Pro Leu Ala Asp Arg Phe Met Asn Ala Val Phe Phe Leu Leu Pro Lys
                    115                 120                 125

Phe His Gly Val Leu Lys Thr Leu Cys Leu Glu Val Val Leu Cys Arg
                    130                 135                 140

Val Glu Gly Met Thr Glu Leu Tyr Phe Gln Leu Lys Ser Lys Asp Phe
145                 150                 155                 160

Val Gln Val Met Arg His Arg Asp Asp Glu Arg Gln Lys Val Cys Leu
                    165                 170                 175

Asp Ile Ile Tyr Lys Met Met Pro Lys Leu Lys Pro Val Glu Leu Arg
                    180                 185                 190

Glu Leu Leu Asn Pro Val Val Glu Phe Val Ser His Pro Ser Thr Thr
                    195                 200                 205

Cys Arg Glu Gln Met Tyr Asn Ile Leu Met Trp Ile His Asp Asn Tyr
                    210                 215                 220

Arg Asp Pro Glu Ser Glu Thr Asp Asn Asp Ser Gln Glu Ile Phe Lys
225                 230                 235                 240

Leu Ala Lys Asp Val Leu Ile Gln Gly Leu Ile Asp Glu Asn Pro Gly
                    245                 250                 255

Leu Gln Leu Ile Ile Arg Asn Phe Trp Ser His Glu Thr Arg Leu Pro
                    260                 265                 270

Ser Asn Thr Leu Asp Arg Leu Leu Ala Leu Asn Ser Leu Tyr Ser Pro
                    275                 280                 285

Lys Ile Glu Val His Phe Leu Ser Leu Ala Thr Asn Phe Leu Leu Glu
                    290                 295                 300

Met Thr Ser Met Ser Pro Asp Tyr Pro Asn Pro Met Phe Glu His Pro
305                 310                 315                 320

Leu Ser Glu Cys Glu Phe Gln Glu Tyr Thr Ile Asp Ser Asp Trp Arg
                    325                 330                 335

Phe Arg Ser Thr Val Leu Thr Pro Met Phe Val Glu Thr Gln Ala Ser
                    340                 345                 350

Gln Gly Thr Leu Gln Thr Arg Thr Gln Glu Gly Ser Leu Ser Ala Arg
                    355                 360                 365

Trp Pro Val Ala Gly Gln Ile Arg Ala Thr Gln Gln His Asp Phe
                    370                 375                 380

Thr Leu Thr Gln Thr Ala Asp Gly Arg Ser Ser Phe Asp Trp Leu Thr
385                 390                 395                 400

Gly Ser Ser Thr Asp Pro Leu Val Asp His Thr Ser Pro Ser Ser Asp
                    405                 410                 415

Ser Leu Leu Phe Ala His Lys Arg Ser Glu Arg Leu Gln Arg Ala Pro
                    420                 425                 430
```

```
Leu Lys Ser Val Gly Pro Asp Phe
        435                 440

<210> SEQ ID NO 10
<211> LENGTH: 200
<212> TYPE: PRT
<213> ORGANISM: Artificial Sequence
<220> FEATURE:
<221> NAME/KEY: PEPTIDE
<222> LOCATION: (1)..(200)
<223> OTHER INFORMATION: HUMAN GENETIC ORIGIN
<220> FEATURE:
<221> NAME/KEY: MOD_RES
<222> LOCATION: (109)..(109)
<223> OTHER INFORMATION: PHOSPHORYLATION at T2609

<400> SEQUENCE: 10

Leu Ala Lys Asp Val Leu Ile Gln Gly Leu Ile Asp Glu Asn Pro Gly
1               5                   10                  15

Leu Gln Leu Ile Ile Arg Asn Phe Trp Ser His Glu Thr Arg Leu Pro
            20                  25                  30

Ser Asn Thr Leu Asp Arg Leu Leu Ala Leu Asn Ser Leu Tyr Ser Pro
        35                  40                  45

Lys Ile Glu Val His Phe Leu Ser Leu Ala Thr Asn Phe Leu Leu Glu
    50                  55                  60

Met Thr Ser Met Ser Pro Asp Tyr Pro Asn Pro Met Phe Glu His Pro
65                  70                  75                  80

Leu Ser Glu Cys Glu Phe Gln Glu Tyr Thr Ile Asp Ser Asp Trp Arg
                85                  90                  95

Phe Arg Ser Thr Val Leu Thr Pro Met Phe Val Glu Thr Gln Ala Ser
            100                 105                 110

Gln Gly Thr Leu Gln Thr Arg Thr Gln Glu Gly Ser Leu Ser Ala Arg
        115                 120                 125

Trp Pro Val Ala Gly Gln Ile Arg Ala Thr Gln Gln His Asp Phe
    130                 135                 140

Thr Leu Thr Gln Thr Ala Asp Gly Arg Ser Ser Phe Asp Trp Leu Thr
145                 150                 155                 160

Gly Ser Ser Thr Asp Pro Leu Val Asp His Thr Ser Pro Ser Ser Asp
                165                 170                 175

Ser Leu Leu Phe Ala His Lys Arg Ser Glu Arg Leu Gln Arg Ala Pro
            180                 185                 190

Leu Lys Ser Val Gly Pro Asp Phe
        195                 200

<210> SEQ ID NO 11
<211> LENGTH: 428
<212> TYPE: PRT
<213> ORGANISM: Artificial Sequence
<220> FEATURE:
<221> NAME/KEY: PEPTIDE
<222> LOCATION: (1)..(428)
<223> OTHER INFORMATION: HUMAN GENETIC ORIGIN
<220> FEATURE:
<221> NAME/KEY: MOD_RES
<222> LOCATION: (335)..(335)
<223> OTHER INFORMATION: PHOSPHORYLATION at T2609

<400> SEQUENCE: 11

Gln Leu Leu Gly Ile Val Met Ala Asn Asp Leu Pro Pro Tyr Asp Pro
1               5                   10                  15

Gln Cys Gly Ile Gln Ser Ser Glu Tyr Phe Gln Ala Leu Val Asn Asn
```

```
                20                  25                  30
Met Ser Phe Val Arg Tyr Lys Glu Val Tyr Ala Ala Ala Glu Val
            35                  40                  45

Leu Gly Leu Ile Leu Arg Tyr Val Met Glu Arg Lys Asn Ile Leu Glu
    50                  55                  60

Glu Ser Leu Cys Glu Leu Val Ala Lys Gln Leu Lys Gln His Gln Asn
65                  70                  75                  80

Thr Met Glu Asp Lys Phe Ile Val Cys Leu Asn Lys Val Thr Lys Ser
                85                  90                  95

Phe Pro Pro Leu Ala Asp Arg Phe Met Asn Ala Val Phe Phe Leu Leu
            100                 105                 110

Pro Lys Phe His Gly Val Leu Lys Thr Leu Cys Leu Glu Val Val Leu
        115                 120                 125

Cys Arg Val Glu Gly Met Thr Glu Leu Tyr Phe Gln Leu Lys Ser Lys
        130                 135                 140

Asp Phe Val Gln Val Met Arg His Arg Asp Glu Arg Gln Lys Val
145                 150                 155                 160

Cys Leu Asp Ile Ile Tyr Lys Met Met Pro Lys Leu Lys Pro Val Glu
                165                 170                 175

Leu Arg Glu Leu Leu Asn Pro Val Glu Phe Val Ser His Pro Ser
            180                 185                 190

Thr Thr Cys Arg Glu Gln Met Tyr Asn Ile Leu Met Trp Ile His Asp
            195                 200                 205

Asn Tyr Arg Asp Pro Glu Ser Glu Thr Asp Asn Asp Ser Gln Glu Ile
    210                 215                 220

Phe Lys Leu Ala Lys Asp Val Leu Ile Gln Gly Leu Ile Asp Glu Asn
225                 230                 235                 240

Pro Gly Leu Gln Leu Ile Ile Arg Asn Phe Trp Ser His Glu Thr Arg
            245                 250                 255

Leu Pro Ser Asn Thr Leu Asp Arg Leu Ala Leu Asn Ser Leu Tyr
            260                 265                 270

Ser Pro Lys Ile Glu Val His Phe Leu Ser Leu Ala Thr Asn Phe Leu
    275                 280                 285

Leu Glu Met Thr Ser Met Ser Pro Asp Tyr Pro Asn Pro Met Phe Glu
290                 295                 300

His Pro Leu Ser Glu Cys Glu Phe Gln Glu Tyr Thr Ile Asp Ser Asp
305                 310                 315                 320

Trp Arg Phe Arg Ser Thr Val Leu Thr Pro Met Phe Val Glu Thr Gln
                325                 330                 335

Ala Ser Gln Gly Thr Leu Gln Thr Arg Thr Gln Glu Gly Ser Leu Ser
            340                 345                 350

Ala Arg Trp Pro Val Ala Gly Gln Ile Arg Ala Thr Gln Gln His
        355                 360                 365

Asp Phe Thr Leu Thr Gln Thr Ala Asp Gly Arg Ser Ser Phe Asp Trp
            370                 375                 380

Leu Thr Gly Ser Ser Thr Asp Pro Leu Val Asp His Thr Ser Pro Ser
385                 390                 395                 400

Ser Asp Ser Leu Leu Phe Ala His Lys Arg Ser Glu Arg Leu Gln Arg
                405                 410                 415

Ala Pro Leu Lys Ser Val Gly Pro Asp Phe Gly Lys
            420                 425
```

<210> SEQ ID NO 12

```
<211> LENGTH: 273
<212> TYPE: PRT
<213> ORGANISM: Artificial Sequence
<220> FEATURE:
<221> NAME/KEY: PEPTIDE
<222> LOCATION: (1)..(273)
<223> OTHER INFORMATION: HUMAN GENETIC ORIGIN
<220> FEATURE:
<221> NAME/KEY: MOD_RES
<222> LOCATION: (180)..(180)
<223> OTHER INFORMATION: PHOSPHORYLATION at T2609

<400> SEQUENCE: 12
```

Glu Arg Gln Lys Val Cys Leu Asp Ile Ile Tyr Lys Met Met Pro Lys
1               5                   10                  15

Leu Lys Pro Val Glu Leu Arg Glu Leu Leu Asn Pro Val Val Glu Phe
            20                  25                  30

Val Ser His Pro Ser Thr Thr Cys Arg Glu Gln Met Tyr Asn Ile Leu
        35                  40                  45

Met Trp Ile His Asp Asn Tyr Arg Asp Pro Glu Ser Glu Thr Asp Asn
    50                  55                  60

Asp Ser Gln Glu Ile Phe Lys Leu Ala Lys Asp Val Leu Ile Gln Gly
65                  70                  75                  80

Leu Ile Asp Glu Asn Pro Gly Leu Gln Leu Ile Ile Arg Asn Phe Trp
                85                  90                  95

Ser His Glu Thr Arg Leu Pro Ser Asn Thr Leu Asp Arg Leu Leu Ala
            100                 105                 110

Leu Asn Ser Leu Tyr Ser Pro Lys Ile Glu Val His Phe Leu Ser Leu
        115                 120                 125

Ala Thr Asn Phe Leu Leu Glu Met Thr Ser Met Ser Pro Asp Tyr Pro
    130                 135                 140

Asn Pro Met Phe Glu His Pro Leu Ser Glu Cys Glu Phe Gln Glu Tyr
145                 150                 155                 160

Thr Ile Asp Ser Asp Trp Arg Phe Arg Ser Thr Val Leu Thr Pro Met
                165                 170                 175

Phe Val Glu Thr Gln Ala Ser Gln Gly Thr Leu Gln Thr Arg Thr Gln
            180                 185                 190

Glu Gly Ser Leu Ser Ala Arg Trp Pro Val Ala Gly Gln Ile Arg Ala
        195                 200                 205

Thr Gln Gln His Asp Phe Thr Leu Thr Gln Thr Ala Asp Gly Arg
    210                 215                 220

Ser Ser Phe Asp Trp Leu Thr Gly Ser Ser Thr Asp Pro Leu Val Asp
225                 230                 235                 240

His Thr Ser Pro Ser Ser Asp Ser Leu Leu Phe Ala His Lys Arg Ser
                245                 250                 255

Glu Arg Leu Gln Arg Ala Pro Leu Lys Ser Val Gly Pro Asp Phe Gly
            260                 265                 270

Lys

```
<210> SEQ ID NO 13
<211> LENGTH: 140
<212> TYPE: PRT
<213> ORGANISM: Artificial Sequence
<220> FEATURE:
<221> NAME/KEY: PEPTIDE
<222> LOCATION: (1)..(140)
<223> OTHER INFORMATION: HUMAN GENETIC ORIGIN
<220> FEATURE:
<221> NAME/KEY: MOD_RES
<222> LOCATION: (49)..(49)
```

<223> OTHER INFORMATION: PHOSPHORYLATION at T2609

<400> SEQUENCE: 13

```
Phe Leu Leu Glu Met Thr Ser Met Ser Pro Asp Tyr Pro Asn Pro Met
1               5                   10                  15

Phe Glu His Pro Leu Ser Glu Cys Glu Phe Gln Glu Tyr Thr Ile Asp
            20                  25                  30

Ser Asp Trp Arg Phe Arg Ser Val Leu Thr Pro Met Phe Val Glu
        35                  40                  45

Thr Gln Ala Ser Gln Gly Thr Leu Gln Thr Arg Thr Gln Glu Gly Ser
    50                  55                  60

Leu Ser Ala Arg Trp Pro Val Ala Gly Gln Ile Arg Ala Thr Gln Gln
65                  70                  75                  80

Gln His Asp Phe Thr Leu Thr Gln Thr Ala Asp Gly Arg Ser Ser Phe
                85                  90                  95

Asp Trp Leu Thr Gly Ser Ser Thr Asp Pro Leu Val Asp His Thr Ser
            100                 105                 110

Pro Ser Ser Asp Ser Leu Leu Phe Ala His Lys Arg Ser Glu Arg Leu
        115                 120                 125

Gln Arg Ala Pro Leu Lys Ser Val Gly Pro Asp Phe
    130                 135                 140
```

<210> SEQ ID NO 14
<211> LENGTH: 102
<212> TYPE: PRT
<213> ORGANISM: Artificial Sequence
<220> FEATURE:
<221> NAME/KEY: PEPTIDE
<222> LOCATION: (1)..(102)
<223> OTHER INFORMATION: HUMAN GENETIC ORIGIN
<220> FEATURE:
<221> NAME/KEY: MOD_RES
<222> LOCATION: (9)..(9)
<223> OTHER INFORMATION: PHOSPHORYLATION at T2609

<400> SEQUENCE: 14

```
Val Leu Thr Pro Met Phe Val Glu Thr Gln Ala Ser Gln Gly Thr Leu
1               5                   10                  15

Gln Thr Arg Thr Gln Glu Gly Ser Leu Ser Ala Arg Trp Pro Val Ala
            20                  25                  30

Gly Gln Ile Arg Ala Thr Gln Gln Gln His Asp Phe Thr Leu Thr Gln
        35                  40                  45

Thr Ala Asp Gly Arg Ser Ser Phe Asp Trp Leu Thr Gly Ser Ser Thr
    50                  55                  60

Asp Pro Leu Val Asp His Thr Ser Pro Ser Ser Asp Ser Leu Leu Phe
65                  70                  75                  80

Ala His Lys Arg Ser Glu Arg Leu Gln Arg Ala Pro Leu Lys Ser Val
                85                  90                  95

Gly Pro Asp Phe Gly Lys
            100
```

<210> SEQ ID NO 15
<211> LENGTH: 13509
<212> TYPE: DNA
<213> ORGANISM: Homo sapiens
<220> FEATURE:
<221> NAME/KEY: misc_feature
<222> LOCATION: (6233)..(6235)
<223> OTHER INFORMATION: Encodes S2056
<220> FEATURE:
<221> NAME/KEY: misc_feature
<222> LOCATION: (7882)..(7884)
<223> OTHER INFORMATION: Encodes T2609

<400> SEQUENCE: 15

| | | | | | |
|---|---|---|---|---|---|
| ggggcatttc | cgggtccggg | ccgagcgggc | gcacgcgcgg | gagcgggact | cggcggcatg | 60 |
| gcgggctccg | gagccggtgt | gcgttgctcc | ctgctgcggc | tgcaggagac | cttgtccgct | 120 |
| gcggaccgct | gcggtgctgc | cctggccggt | catcaactga | tccgcggcct | ggggcaggaa | 180 |
| tgcgtcctga | gcagcagccc | cgcggtgctg | gcattacaga | catctttagt | tttttccaga | 240 |
| gatttcggtt | tgcttgtatt | tgtccggaag | tcactcaaca | gtattgaatt | tcgtgaatgt | 300 |
| agagaagaaa | tcctaaagtt | tttatgtatt | ttcttagaaa | aaatgggcca | aagatcgca | 360 |
| ccttactctg | ttgaaattaa | gaacacttgt | accagtgttt | atacaaaaga | tagagctgct | 420 |
| aaatgtaaaa | ttccagccct | ggaccttctt | attaagttac | ttcagacttt | tagaagttct | 480 |
| agactcatgg | atgaatttaa | aattggagaa | ttatttagta | aattctatgg | agaacttgca | 540 |
| ttgaaaaaaa | aaataccaga | tacagtttta | gaaaagtat | atgagctcct | aggattattg | 600 |
| ggtgaagttc | atcctagtga | gatgataaat | aatgcagaaa | acctgttccg | cgcttttctg | 660 |
| ggtgaactta | agacccagat | gacatcagca | gtaagagagc | ccaaactacc | tgttctggca | 720 |
| ggatgtctga | aggggttgtc | ctcacttctg | tgcaacttca | ctaagtccat | ggaagaagat | 780 |
| ccccagactt | caagggagat | ttttaatttt | gtactaaagg | caattcgtcc | tcagattgat | 840 |
| ctgaagagat | atgctgtgcc | ctcagctggc | ttgcgcctat | ttgccctgca | tgcatctcag | 900 |
| tttagcacct | gccttctgga | caactacgtg | tctctatttg | aagtcttgtt | aaagtggtgt | 960 |
| gcccacacaa | atgtagaatt | gaaaaagct | gcactttcag | ccctggaatc | ctttctgaaa | 1020 |
| caggtttcta | atatggtggc | gaaaaatgca | gaaatgcata | aaaataaact | gcagtacttt | 1080 |
| atggagcagt | tttatggaat | catcagaaat | gtggattcga | caacaagga | gttatctatt | 1140 |
| gctatccgtg | gatatggact | ttttgcagga | ccgtgcaagg | ttataaacgc | aaaagatgtt | 1200 |
| gacttcatgt | acgttgagct | cattcagcgc | tgcaagcaga | tgttcctcac | ccagacagac | 1260 |
| actggtgacg | accgtgttta | tcagatgcca | agcttcctcc | agtctgttgc | aagcgtcttg | 1320 |
| ctgtaccttg | acacagttcc | tgaggtgtat | actccagttc | tggagcacct | cgtggtgatg | 1380 |
| cagatagaca | gtttcccaca | gtacagtcca | aaaatgcagc | tggtgtgttg | cagagccata | 1440 |
| gtgaaggtgt | tcctagcttt | ggcagcaaaa | gggccagttc | tcaggaattg | cattagtact | 1500 |
| gtggtgcatc | agggttaat | cagaatatgt | tctaaaccag | tggtccttcc | aaagggccct | 1560 |
| gagtctgaat | ctgaagacca | ccgtgcttca | ggggaagtca | gaactggcaa | atggaaggtg | 1620 |
| cccacataca | aagactacgt | ggatctcttc | agacatctcc | tgagctctga | ccagatgatg | 1680 |
| gattctattt | tagcagatga | agcatttttc | tctgtgaatt | cctccagtga | aagtctgaat | 1740 |
| catttacttt | atgatgaatt | tgtaaaatcc | gttttgaaga | ttgttgagaa | attggatctt | 1800 |
| acacttgaaa | tacagactgt | tggggaacaa | gagaatggag | atgaggcgcc | tggtgtttgg | 1860 |
| atgatcccaa | cttcagatcc | agcggctaac | ttgcatccag | ctaaacctaa | agattttcg | 1920 |
| gctttcatta | acctggtgga | attttgcaga | gagattctcc | ctgagaaaca | agcagaattt | 1980 |
| tttgaaccat | gggtgtactc | attttcatat | gaattaattt | tgcaatctac | aaggttgccc | 2040 |
| ctcatcagtg | gtttctacaa | attgctttct | attacagtaa | gaaatgccaa | gaaaataaaa | 2100 |
| tatttcgagg | gagttagtcc | aaagagtctg | aaacactctc | ctgaagaccc | agaaaagtat | 2160 |
| tcttgctttg | ctttatttgt | gaaatttggc | aaagaggtgg | cagttaaaat | gaagcagtac | 2220 |

-continued

```
aaagatgaac ttttggcctc ttgtttgacc tttcttctgt ccttgccaca caacatcatt    2280
gaactcgatg ttagagccta cgttcctgca ctgcagatgg ctttcaaact gggcctgagc    2340
tataccccct tggcagaagt aggcctgaat gctctagaag aatggtcaat ttatattgac    2400
agacatgtaa tgcagcctta ttacaaagac attctcccct gcctggatgg atacctgaag    2460
acttcagcct tgtcagatga gaccaagaat aactgggaag tgtcagctct ttctcgggct    2520
gcccagaaag gatttaataa agtggtgtta aagcatctga agaagacaaa gaacctttca    2580
tcaaacgaag caatatcctt agaagaaata agaattagag tagtacaaat gcttggatct    2640
ctaggaggac aaataaacaa aaatcttctg acagtcacgt cctcagatga gatgatgaag    2700
agctatgtgg cctgggacag agagaagcgg ctgagctttg cagtgcccct tagagagatg    2760
aaacctgtca ttttcctgga tgtgttcctg cctcgagtca cagaattagc gctcacagcc    2820
agtgacagac aaactaaagt tgcagcctgt gaacttttac atagcatggt tatgtttatg    2880
ttgggcaaag ccacgcagat gccagaaggg ggacagggag ccccacccat gtaccagctc    2940
tataagcgga cgtttcctgt gctgcttcga cttgcgtgtg atgttgatca ggtgacaagg    3000
caactgtatg agccactagt tatgcagctg attcactggt tcactaacaa caagaaattt    3060
gaaagtcagg atactgttgc cttactagaa gctatattgg atggaattgt ggaccctgtt    3120
gacagtactt taagagattt ttgtggtcgg tgtattcgag aattccttaa atggtccatt    3180
aagcaaataa caccacagca gcaggagaag agtccagtaa acaccaaatc gcttttcaag    3240
cgactttata gccttgcgct tcaccccaat gctttcaaga ggctgggagc atcacttgcc    3300
tttaataata tctacaggga attcagggaa gaagagtctc tggtggaaca gtttgtgttt    3360
gaagccttgg tgatatacat ggagagtctg gccttagcac atgcagatga gaagtcctta    3420
ggtacaattc aacagtgttg tgatgccatt gatcacctat gccgcatcat tgaaaagaag    3480
catgtttctt taaataaagc aaagaaacga cgtttgccgc gaggatttcc accttccgca    3540
tcattgtgtt tattggatct ggtcaagtgg cttttagctc attgtgggag ccccagaca    3600 gaatgtcgac acaaatccat tgaactcttt tataaattcg ttcctttatt gccaggcaac    3660
agatccccta atttgtggct gaaagatgtt ctcaaggaag aaggtgtctc ttttctcatc    3720
aacacctttg agggggtgg ctgtggccag ccctcgggca tcctggccca gcccacccctc    3780 ttgtaccttc gggggccatt cagcctgcag gccacgctat gctggctgga cctgctcctg    3840
gccgcgttgg agtgctacaa cacgttcatt ggcgagagaa ctgtaggagc gctccaggtc    3900
ctaggtactg aagcccagtc ttcacttttg aaagcagtgg ctttcttctt agaaagcatt    3960
gccatgcatg acattatagc agcagaaaag tgctttggca ctgggcagc aggtaacaga    4020 acaagcccac aagagggaga aaggtacaac tacagcaaat gcaccgttgt ggtccggatt    4080
atggagttta ccacgactct gctaaacacc tccccggaag gatggaagct cctgaagaag    4140
gacttgtgta atacacacct gatgagagtc ctggtgcaga cgctgtgtga gcccgcaagc    4200
ataggtttca acatcggaga cgtccaggtt atggctcatc ttcctgatgt ttgtgtgaat    4260
ctgatgaaag ctctaaagat gtccccatac aaagatatcc tagagaccca tctgagagag    4320
aaaataacag cacagagcat tgaggagctt tgtgccgtca acttgtatgg ccctgacgcg    4380
caagtggaca ggagcaggct ggctgctgtt gtgtctgcct gtaaacagct tcacagagct    4440
gggcttctgc ataatatatt accgtctcag tccacagatt tgcatcattc tgttggcaca    4500
gaacttcttt ccctggttta taaaggcatt gcccctggag atgagagaca gtgtctgcct    4560
tctctagacc tcagttgtaa gcagctggcc agcggacttc tggagttagc ctttgctttt    4620
```

```
ggaggactgt gtgagcgcct tgtgagtctt ctcctgaacc cagcggtgct gtccacggcg   4680
tccttgggca gctcacaggg cagcgtcatc cacttctccc atggggagta tttctatagc   4740
ttgttctcag aaacgatcaa cacgaatta ttgaaaaatc tggatcttgc tgtattggag    4800
ctcatgcagt cttcagtgga taataccaaa atggtgagtg ccgttttgaa cggcatgtta   4860
gaccagagct tcagggagcg agcaaaccag aaacaccaag gactgaaact tgcgactaca   4920
attctgcaac actggaagaa gtgtgattca tggtgggcca agattcccc tctcgaaact    4980 aaaatggcag tgctggcctt actggcaaaa atttttacaga ttgattcatc tgtatctttt  5040
aatacaagtc atggttcatt ccctgaagtc tttacaacat atattagtct acttgctgac   5100
acaaagctgg atctacattt aaagggccaa gctgtcactc ttcttccatt cttcaccagc   5160
ctcactggag gcagtctgga ggaacttaga cgtgttctgg agcagctcat cgttgctcac   5220
ttccccatgc agtccaggga atttcctcca ggaactccgc ggttcaataa ttatgtggac   5280
tgcatgaaaa agtttctaga tgcattggaa ttatctcaaa gccctatgtt gttggaattg   5340
atgacagaag ttcttttgtcg gaacagcag catgtcatgg aagaattatt tcaatccagt   5400
ttcaggagga ttgccagaag gggttcatgt gtcacacaag taggccttct ggaaagcgtg   5460
tatgaaatgt tcaggaagga tgaccccgc ctaagtttca cacgccagtc ctttgtggac    5520
cgctccctcc tcactctgct gtggcactgt agcctggatg ctttgagaga attcttcagc   5580
acaattgtgg tggatgccat tgatgtgttg aagtccaggt ttacaaagct aaatgaatct   5640
acctttgata ctcaaatcac caagaagatg ggctactata agattctaga cgtgatgtat   5700
tctcgccttc ccaaagatga tgttcatgct aaggaatcaa aaattaatca agttttccat   5760
ggctcgtgta ttacagaagg aaatgaactt acaaagacat tgattaaatt gtgctacgat   5820
gcatttacag agaacatggc aggagagaat cagctgctgg agaggagaag actttaccat   5880
tgtgcagcat acaactgcgc catatctgtc atctgctgtg tcttcaatga gttaaaattt   5940
taccaaggtt ttctgtttag tgaaaaacca gaaaagaact tgcttatttt tgaaaatctg   6000
atcgacctga agcgccgcta aattttcct gtagaagttg aggttcctat ggaaagaaag    6060
aaaaagtaca ttgaaattag gaaagaagcc agagaagcag caaatgggga ttcagatggt   6120
ccttcctata tgtcttccct gtcatatttg gcagacagta ccctgagtga ggaaatgagt   6180
caatttgatt tctcaaccgg agttcagagc tattcataca gctcccaaga ccctagacct   6240
gccactggtc gttttcggag acgggagcag cgggacccca cggtgcatga tgatgtgctg   6300
gagctggaga tggacgagct caatcggcat gagtgcatgg cgcccctgac ggccctggtc   6360
aagcacatgc acagaagcct gggcccgcct caaggagaag aggattcagt gccaagagat   6420
cttccttctt ggatgaaatt cctccatggc aaactgggaa atccaatagt accattaaat   6480
atccgtctct tcttagccaa gcttgttatt aatacagaag aggtcttttcg cccttacgcg  6540 aagcactggc ttagcccctt gctgcagctg gctgcttctg aaaacaatgg aggagaagga   6600
attcactaca tggtggttga gatagtggcc actattcttt catggacagg cttggccact   6660
ccaacagggg tccctaaaga tgaagtgtta gcaaatcgat tgcttaattt cctaatgaaa   6720
catgtctttc atccaaaaag agctgtgttt agacacaacc ttgaaattat aaagacccttt  6780 gtcgagtgct ggaaggattg tttatccatc ccttataggt taatatttga aaagttttcc   6840
ggtaaagatc ctaattctaa agacaactca gtagggattc aattgctagg catcgtgatg   6900
gccaatgacc tgcctcccta tgacccacag tgtggcatcc agagtagcga atacttccag   6960
```

```
gctttggtga ataatatgtc ctttgtaaga tataaagaag tgtatgccgc tgcagcagaa      7020
gttctaggac ttatacttcg atatgttatg gagagaaaaa acatactgga ggagtctctg      7080
tgtgaactgg ttgcgaaaca attgaagcaa catcagaata ctatggagga caagtttatt      7140
gtgtgcttga acaaagtgac caagagcttc cctcctcttg cagacaggtt catgaatgct      7200
gtgttctttc tgctgccaaa atttcatgga gtgttgaaaa cactctgtct ggaggtggta      7260
ctttgtcgtg tggagggaat gacagagctg tacttccagt taaagagcaa ggacttcgtt      7320
caagtcatga gacatagaga tgatgaaaga caaaaagtat gtttggacat aatttataag      7380
atgatgccaa agttaaaacc agtagaactc cgagaacttc tgaacccgt tgtggaattc       7440 gtttcccatc cttctacaac atgtagggaa caaatgtata atattctcat gtggattcat      7500
gataattaca gagatccaga aagtgagaca gataatgact cccaggaaat atttaagttg      7560
gcaaaagatg tgctgattca aggattgatc gatgagaacc ctggacttca attaattatt      7620
cgaaatttct ggagccatga aactaggtta ccttcaaata ccttggaccg gttgctggca      7680
ctaaattcct tatattctcc taagatagaa gtgcactttt taagtttagc aacaaatttt      7740
ctgctcgaaa tgaccagcat gagcccagat tatccaaacc ccatgttcga gcatcctctg      7800
tcagaatgcg aatttcagga atataccatt gattctgatt ggcgtttccg aagtactgtt      7860
ctcactccga tgtttgtgga gacccaggcc tcccagggca ctctccagac ccgtacccag      7920
gaagggtccc tctcagctcg ctggccagtg gcagggcaga taagggccac ccagcagcag      7980
catgacttca cactgacaca gactgcagat ggaagaagct catttgattg gctgaccggg      8040
agcagcactg acccgctggt cgaccacacc agtccctcat ctgactcctt gctgtttgcc      8100
cacaagagga gtgaaaggtt acagagagca cccttgaagt cagtggggcc tgattttggg      8160
aaaaaaaggc tgggccttcc aggggacgag gtggataaca aagtgaaagg tgcggccggc      8220
cggacggacc tactacgact gcgcagacgg tttatgaggg accaggagaa gctcagtttg      8280
atgtatgcca gaaaaggcgt tgctgagcaa aaacgagaga aggaaatcaa gagtgagtta      8340
aaaatgaagc aggatgccca ggtcgttctg tacagaagct accggcacgg agaccttcct      8400
gacattcaga tcaagcacag cagcctcatc accccgttac aggccgtggc ccagagggac      8460
ccaataattg caaacagct ctttagcagc ttgttttctg aattttgaa agagatggat       8520 aaatttaaga cactgtctga aaaaacaac atcactcaaa agttgcttca agacttcaat       8580
cgttttctta ataccacctt ctctttcttt ccacccttg tctcttgtat tcaggacatt       8640
agctgtcagc acgcagccct gctgagcctc gacccagcgg ctgttagcgc tggttgcctg      8700
gccagcctac agcagcccgt gggcatccgc ctgctagagg aggctctgct ccgcctgctg      8760
cctgctgagc tgcctgccaa gcgagtccgt gggaaggccc gcctccctcc tgatgtcctc      8820
agatgggtgg agcttgctaa gctgtataga tcaattggag aatacgacgt cctccgtggg      8880
attttaccca gtgagatagg aacaaagcaa atcactcaga gtgcattatt agcagaagcc      8940
agaagtgatt attctgaagc tgctaagcag tatgatgagg ctctcaataa acaagactgg      9000
gtagatggtg agcccacaga agccgagaag gattttgtgg aacttgcatc ccttgactgt      9060
tacaaccacc ttgctgagtg gaaatcactt gaatactgtt ctacagccag tatagacagt      9120 gagaacccc cagacctaaa taaatctgg agtgaaccat tttatcagga aacatatcta       9180
ccttacatga tccgcagcaa gctgaagctg ctgctccagg gagaggctga ccagtccctg      9240 ctgacatttta ttgacaaagc tatgcacggg gagctccaga aggcgattct agagcttcat      9300
tacagtcaag agctgagtct gctttacctc ctgcaagatg atgttgacag agccaaatat      9360
```

```
tacattcaaa atggcattca gagttttatg cagaattatt ctagtattga tgtcctctta    9420
caccaaagta gactcaccaa attgcagtct gtacaggctt aacagaaaat tcaggagttc    9480
atcagcttta taagcaaaca aggcaattta tcatctcaag ttccccttaa gagacttctg    9540
aacacctgga caaacagata tccagatgct aaaatggacc caatgaacat ctgggatgac    9600
atcatcacaa atcgatgttt ctttctcagc aaaatagagg agaagcttac ccctcttcca    9660
gaagataata gtatgaatgt ggatcaagat ggagacccca gtgacaggat ggaagtgcaa    9720
gagcaggaag aagatatcag ctccctgatc aggagttgca agttttccat gaaaatgaag    9780
atgatagaca gtgcccggaa gcagaacaat ttctcacttg ctatgaaact actgaaggag    9840
ctgcataaag agtcaaaaac cagagacgat tggctggtga gctgggtgca gagctactgc    9900
cgcctgagcc actgccggag ccggtcccag ggctgctctg agcaggtgct cactgtgctg    9960
aaaacagtct ctttgttgga tgagaacaac gtgtcaagct acttaagcaa aaatattctg   10020
gctttccgtg accagaacat tctcttgggt acaacttaca ggatcatagc gaatgctctc   10080
agcagtgagc cagcctgcct tgctgaaatc gaggaggaca aggctagaag aatcttagag   10140
cttttctgga tccagttcag aggattcagag aaggtgatcg cgggtctgta ccagagagca   10200
ttccagcacc tctctgaggc tgtgcaggcg gctgaggagg aggcccagcc tccctcctgg   10260
agctgtgggc ctgcagctgg ggtgattgat gcttacatga cgctggcaga tttctgtgac   10320
caacagctgc gcaaggagga agagaatgca tcagttattg attctgcaga actgcaggcg   10380
tatccagcac ttgtggtgga gaaaatgttg aaagctttaa aattaaattc caatgaagcc   10440
agattgaagt ttcctagatt acttcagatt atagaacggt atccagagga gactttgagc   10500
ctcatgacaa aagagatctc ttccgttccc tgctggcagt tcatcagctg gatcagccac   10560
atggtggcct tactggacaa agaccaagcc gttgctgttc agcactctgt ggaagaaatc   10620
actgataact acccgcaggc tattgtttat cccttcatca taagcagcga aagctattcc   10680
ttcaaggata cttctactgg tcataagaat aaggagtttg tggcaaggat taaaagtaag   10740
ttggatcaag gaggagtgat tcaagatttt attaatgcct tagatcagct ctctaatcct   10800
gaactgctct ttaaggattg gagcaatgat gtaagagctg aactagcaaa aaccccctgta   10860
aataaaaaaa acattgaaaa aatgtatgaa agaatgtatg cagccttggg tgacccaaag   10920
gctccaggcc tgggggcctt tagaaggaag tttattcaga cttttggaaa agaatttgat   10980
aaacattttg ggaaaggagg ttctaaacta ctgagaatga agctcagtga cttcaacgac   11040
attaccaaca tgctactttt aaaaatgaac aaagactcaa agcccctgg gaatctgaaa   11100
gaatgttcac cctggatgag cgacttcaaa gtggagttcc tgagaaatga gctggagatt   11160
cccggtcagt atgacggtag gggaaagcca ttgccagagt accacgtgcg aatcgccggg   11220
tttgatgagc gggtgacagt catggcgtct ctgcgaaggc ccaagcgcat catcatccgt   11280
ggccatgacg agagggaaca cccttttcctg gtgaagggtg gcgaggacct gcggcaggac   11340
cagcgcgtgg agcagctctt ccaggtcatg aatgggatcc tggcccaaga ctccgcctgc   11400
agccagaggg ccctgcagct gaggacctat agcgttgtgc ccatgacctc caggttagga   11460
ttaattgagt ggcttgaaaa tactgttacc ttgaaggacc ttcttttgaa caccatgtcc   11520
caagaggaga aggcggctta cctgagtgat cccagggcac cgccgtgtga atataaagat   11580
tggctgacaa aaatgtcagg aaaacatgat gttggagctt acatgctaat gtataagggc   11640
gctaatcgta ctgaaacagt cacgtctttt agaaaacgag aaagtaaagt gcctgctgat   11700
```

-continued

```
ctcttaaagc gggccttcgt gaggatgagt acaagccctg aggctttcct ggcgctccgc    11760
tcccacttcg ccagctctca cgctctgata tgcatcagcc actggatcct cgggattgga    11820
gacagacatc tgaacaactt tatggtggcc atggagactg gcggcgtgat cgggatcgac    11880
tttgggcatg cgtttggatc cgctacacag tttctgccag tccctgagtt gatgcctttt    11940
cggctaactc gccagtttat caatctgatg ttaccaatga agaaacgggc cttatgtac     12000 agcatcatgg tacacgcact ccgggccttc cgctcagacc ctggcctgct caccaacacc    12060
atggatgtgt tgtcaagga gccctccttt gattggaaaa attttgaaca gaaaatgctg    12120
aaaaaaggag ggtcatggat tcaagaaata aatgttgctg aaaaaaattg gtaccccga    12180 cagaaaatat gttacgctaa gagaaagtta gcaggtgcca atccagcagt cattacttgt    12240
gatgagctac tcctgggtca tgagaaggcc ctgccttca gagactatgt ggctgtggca    12300
cgaggaagca agatcacaa cattcgtgcc caagaaccag agagtgggct ttcagaagag    12360
actcaagtga agtgcctgat ggaccaggca acagacccca acatccttgg cagaacctgg    12420
gaaggatggg agccctggat gtgaggtctg tgggagtctg cagatagaaa gcattacatt    12480
gtttaaagaa tctactatac tttggttggc agcattccat gagctgattt tcctgaaaca    12540
ctaaagagaa atgtctttg tgctacagtt tcgtagcatg agtttaaatc aagattatga    12600
tgagtaaatg tgtatgggtt aaatcaaaga taaggttata gtaacatcaa agattaggtg    12660
aggtttatag aaagatagat atccaggctt accaaagtat taagtcaaga atataatatg    12720
tgatcagctt tcaaagcatt tacaagtgct gcaagttagt gaaacagctg tctccgtaaa    12780
tggaggaaat gtggggaagc cttggaatgc ccttctggtt ctggcacatt ggaaagcaca    12840
ctcagaaggc ttcatcacca agatttgg agagtaaagc taagtatagt tgatgtaaca    12900
ttgtagaagc agcataggaa caataagaac aataggtaaa gctataatta tggcttatat    12960
ttagaaatga ctgcatttga tattttagga tattttcta ggttttttcc tttcattta    13020 ttctcttcta gttttgacat tttatgatag atttgctctc tagaaggaaa cgtctttatt    13080
taggagggca aaaattttgg tcatagcatt cactttgtct attccaatct acaactggaa    13140
gatacataaa agtgctttgc attgaatttg ggataacttc aaaaatccca tggttgttgt    13200
tagggatagt actaagcatt tcagttccag gagaataaaa gaaattccta tttgaaatga    13260
attcctcatt tggaggaaaa aaagcatgca ttctagcaca acaagatgaa attatggaat    13320 acaaagtgg ctccttccca tgtgcagtcc ctgtccccc cgccagtcc tccacaccca     13380 aactgtttct gattggcttt tagcttttg ttgttttttt ttttccttct aacacttgta    13440
tttggaggct cttctgtgat tttgagaagt atactcttga gtgtttaata aagtttttt    13500 ccaaaagta                                                           13509
```

<210> SEQ ID NO 16
<211> LENGTH: 63
<212> TYPE: DNA
<213> ORGANISM: Artificial Sequence
<220> FEATURE:
<223> OTHER INFORMATION: cDNA sequence encoding the 2599-2619 peptide
<220> FEATURE:
<221> NAME/KEY: CDS
<222> LOCATION: (1)..(63)
<223> OTHER INFORMATION: HUMAN GENETIC ORIGIN
<220> FEATURE:
<221> NAME/KEY: misc_feature
<222> LOCATION: (31)..(33)
<223> OTHER INFORMATION: encodes T2609 residue

<400> SEQUENCE: 16

```
agtactgttc tcactccgat gtttgtggag acccaggcct cccagggcac tctccagacc    60
cgt                                                                  63

<210> SEQ ID NO 17
<211> LENGTH: 87
<212> TYPE: DNA
<213> ORGANISM: Artificial sequence
<220> FEATURE:
<223> OTHER INFORMATION: cDNA sequence encoding the 2044-2072 peptide
<220> FEATURE:
<221> NAME/KEY: CDS
<222> LOCATION: (1)..(87)
<223> OTHER INFORMATION: HUMAN GENETIC ORIGIN
<220> FEATURE:
<221> NAME/KEY: misc_feature
<222> LOCATION: (37)..(37)
<223> OTHER INFORMATION: encodes S2056 resdiue

<400> SEQUENCE: 17
gatttctcaa ccggagttca gagctattca tacagctccc aagaccctag acctgccact    60
ggtcgttttc ggagacggga gcagcgg                                        87

<210> SEQ ID NO 18
<211> LENGTH: 909
<212> TYPE: DNA
<213> ORGANISM: Artificial Sequence
<220> FEATURE:
<223> OTHER INFORMATION: cDNA sequence encoding the 1879-2182 peptide
<220> FEATURE:
<221> NAME/KEY: CDS
<222> LOCATION: (1)..(909)
<223> OTHER INFORMATION: HUMAN GENETIC ORIGIN
<220> FEATURE:
<221> NAME/KEY: misc_feature
<222> LOCATION: (529)..(529)
<223> OTHER INFORMATION: encodes S2056 residue

<400> SEQUENCE: 18
atgtattctc gccttcccaa agatgatgtt catgctaagg aatcaaaaat taatcaagtt    60
ttccatggct cgtgtattac agaaggaaat gaacttacaa agacattgat taaattgtgc   120
tacgatgcat ttacagagaa catggcagga gagaatcagc tgctggagag agaagactt    180 taccattgtg cagcatacaa ctgcgccata tctgtcatct gctgtgtctt caatgagtta   240
aaattttacc aaggttttct gtttagtgaa aaaccagaaa agaacttgct tattttgaa    300 aatctgatcg acctgaagcg ccgctataat tttcctgtag aagttgaggt tcctatggaa   360
agaaagaaaa agtacattga aattaggaaa gaagccagag aagcagcaaa tgggattca    420 gatggtcctt cctatatgtc ttccctgtca tatttggcag acagtaccct gagtgaggaa   480
atgagtcaat tgatttctc aaccggagtt cagagctatt catacagctc caagaccct    540 agacctgcca ctggtcgttt tcggagacgg gagcagcggg accccacggt gcatgatgat   600
gtgctggagc tggagatgga cgagctcaat cggcatgagt gcatggcgcc cctgacggcc   660
ctggtcaagc acatgcacag aagcctgggc ccgcctcaag agaagaggg ttcagtgcca    720 agagatcttc cttcttggat gaattcctc catggcaaac tgggaaatcc aatagtacca   780
ttaaatatcc gtctcttctt agccaagctt gttattaata cagaagaggt ctttcgccct   840
tacgcgaagc actggcttag ccccttgctg cagctggctg cttctgaaaa caatggagga   900
gaaggaatt                                                           909

<210> SEQ ID NO 19
```

```
<211> LENGTH: 1164
<212> TYPE: DNA
<213> ORGANISM: Artificial sequence
<220> FEATURE:
<223> OTHER INFORMATION: Cloned DNA sequence encoding the 1879-2267
      peptide
<220> FEATURE:
<221> NAME/KEY: CDS
<222> LOCATION: (1)..(1164)
<223> OTHER INFORMATION: HUMAN GENETIC ORIGIN
<220> FEATURE:
<221> NAME/KEY: misc_feature
<222> LOCATION: (529)..(531)
<223> OTHER INFORMATION: encodes S2056 residue

<400> SEQUENCE: 19
atgtattctc gccttcccaa agatgatgtt catgctaagg aatcaaaaat taatcaagtt      60
ttccatggct cgtgtattac agaaggaaat gaacttacaa agacattgat taaattgtgc    120
tacgatgcat ttacagagaa catggcagga gagaatcagc tgctggagag gagaagactt    180
taccattgtg cagcatacaa ctgcgccata tctgtcatct gctgtgtctt caatgagtta    240 aaatttacc aaggttttct gtttagtgaa aaaccagaaa agaacttgct tattttgaa     300 aatctgatcg acctgaagcg ccgctataat tttcctgtag aagttgaggt tcctatggaa    360
agaaagaaaa agtacattga aattaggaaa gaagccagag aagcagcaaa tggggattca    420
gatggtcctt cctatatgtc ttccctgtca tatttggcag acagtaccct gagtgaggaa    480
atgagtcaat tgatttctc aaccggagtt cagagctatt catacagctc ccaagaccct    540
agacctgcca ctggtcgttt tcggagacgg gagcagcggg acccacggt gcatgatgat    600 gtgctggagc tggagatgga cgagctcaat cggcatgagt gcatggcgcc cctgacggcc    660
ctggtcaagc acatgcacag aagcctgggc ccgcctcaag gagaagagga ttcagtgcca    720
agagatcttc cttcttggat gaaattcctc catggcaaac tgggaaatcc aatagtacca    780
ttaaatatcc gtctcttctt agccaagctt gttattaata cagaagaggt ctttcgcccct    840 tacgcgaagc actggcttag ccccttgctg cagctggctg cttctgaaaa caatggagga    900
gaaggaattc actacatggt ggttgagata gtggccacta ttctttcatg gacaggcttg    960
gccactccaa caggggtccc taaagatgaa gtgttagcaa atcgattgct taatttccta   1020
atgaaacatg tctttcatcc aaaaagagct gtgtttagac acaaccttga aattataaag   1080
acccttgtcg agtgctggaa ggattgttta tccatccctt ataggttaat atttgaaaag   1140
ttttccggta aagatcctaa ttct                                           1164

<210> SEQ ID NO 20
<211> LENGTH: 2463
<212> TYPE: DNA
<213> ORGANISM: Artificial Sequence
<220> FEATURE:
<223> OTHER INFORMATION: cDNA sequence encoding the 1879-2700 peptide
<220> FEATURE:
<221> NAME/KEY: CDS
<222> LOCATION: (1)..(2463)
<223> OTHER INFORMATION: HUMAN GENETIC ORIGIN
<220> FEATURE:
<221> NAME/KEY: misc_feature
<222> LOCATION: (529)..(531)
<223> OTHER INFORMATION: encodes S2056 residue
<220> FEATURE:
<221> NAME/KEY: misc_feature
<222> LOCATION: (2188)..(2190)
<223> OTHER INFORMATION: encodes T2609 residue

<400> SEQUENCE: 20
```

```
atgtattctc gccttcccaa agatgatgtt catgctaagg aatcaaaaat taatcaagtt      60
ttccatggct cgtgtattac agaaggaaat gaacttacaa agacattgat taaattgtgc     120
tacgatgcat ttacagagaa catggcagga gagaatcagc tgctggagag gagaagactt    180
taccattgtg cagcatacaa ctgcgccata tctgtcatct gctgtgtctt caatgagtta    240 aaatttacc aaggttttct gtttagtgaa aaaccagaaa agaacttgct tattttgaa     300 aatctgatcg acctgaagcg ccgctataat tttcctgtag aagttgaggt tcctatggaa    360
agaaagaaaa agtacattga aattaggaaa gaagccagag aagcagcaaa tggggattca    420
gatggtcctt cctatatgtc ttccctgtca tatttggcag acagtaccct gagtgaggaa    480
atgagtcaat ttgatttctc aaccggagtt cagagctatt catacagctc ccaagaccct    540
agacctgcca ctggtcgttt tcggagacgg agcagcggg accccacggt gcatgatgat    600
gtgctggagc tggagatgga cgagctcaat cggcatgagt gcatggcgcc cctgacggcc    660
ctggtcaagc acatgcacag aagcctgggc ccgcctcaag gagaagagga ttcagtgcca    720
agagatcttc cttcttggat gaaattcctc catggcaaac tgggaaatcc aatagtacca    780
ttaaatatcc gtctcttctt agccaagctt gttattaata cagaagaggt ctttcgccct    840
tacgcgaagc actggcttag ccccttgctg cagctggctg cttctgaaaa caatggagga    900
gaaggaattc actacatggt ggttgagata gtggccacta ttctttcatg gacaggcttg    960
gccactccaa caggggtccc taaagatgaa gtgttagcaa atcgattgct taatttccta    1020
atgaaacatg tctttcatcc aaaaagagct gtgtttagac acaaccttga aattataaag    1080
acccttgtcg agtgctggaa ggattgttta tccatccctt ataggttaat atttgaaaag    1140
ttttccggta aagatcctaa ttctaaagac aactcagtag ggattcaatt gctaggcatc    1200
gtgatggcca atgacctgcc tccctatgac ccacagtgtg gcatccagag tagcgaatac    1260
ttccaggctt tggtgaataa tatgtccttt gtaagatata aagaagtgta tgccgctgca    1320
gcagaagttc taggacttat acttcgatat gttatggaga gaaaaaacat actggaggag    1380
tctctgtgtg aactggttgc gaaacaattg aagcaacatc agaatactat ggaggacaag    1440
tttattgtgt gcttgaacaa agtgaccaag agcttccctc ctcttgcaga caggttcatg    1500
aatgctgtgt tctttctgct gccaaaattt catggagtgt tgaaaacact ctgtctggag    1560
gtggtacttt gtcgtgtgga gggaatgaca gagctgtact tccagttaaa gagcaaggac    1620
ttcgttcaag tcatgagaca tagagatgat gaaagacaaa aagtatgttt ggacataatt    1680
tataagatga tgccaaagtt aaaaccagta gaactccgag aacttctgaa ccccgttgtg    1740
gaattcgttt cccatccttc tacaacatgt agggaacaaa tgtataatat tctcatgtgg    1800
attcatgata attacagaga tccagaaagt gagacagata atgactccca ggaaatattt    1860
aagttggcaa aagatgtgct gattcaagga ttgatcgatg agaaccctgg acttcaatta    1920
attattcgaa atttctggag ccatgaaact aggttacctt caaataccct ggaccggttg    1980
ctggcactaa attccttata ttctcctaag atagaagtgc acttttaag tttagcaaca    2040 aattttctgc tcgaaatgac cagcatgagc ccagattatc aaacccccat gttcgagcat    2100
cctctgtcag aatgcgaatt tcaggaatat accattgatt ctgattggcg tttccgaagt    2160
actgttctca ctccgatgtt tgtggagacc caggcctccc agggcactct ccagacccgt    2220
acccaggaag ggtccctctc agctcgctgg ccagtggcag ggcagataag ggccacccag    2280
cagcagcatg acttcacact gacacagact gcagatggaa gaagctcatt tgattggctg    2340
accgggagca gcactgaccc gctggtcgac cacaccagtc cctcatctga ctccttgctg    2400
```

```
tttgcccaca agaggagtga aaggttacag agagcaccct tgaagtcagt ggggcctgat    2460
ttt                                                                 2463

<210> SEQ ID NO 21
<211> LENGTH: 1320
<212> TYPE: DNA
<213> ORGANISM: Artificial sequence
<220> FEATURE:
<223> OTHER INFORMATION: cDNA sequence encoding the 2261-2700 peptide
<220> FEATURE:
<221> NAME/KEY: CDS
<222> LOCATION: (1)..(1320)
<223> OTHER INFORMATION: HUMAN GENETIC ORIGIN
<220> FEATURE:
<221> NAME/KEY: misc_feature
<222> LOCATION: (1045)..(1047)
<223> OTHER INFORMATION: encodes T2609 residue

<400> SEQUENCE: 21
tccggtaaag atcctaattc taaagacaac tcagtaggga ttcaattgct aggcatcgtg     60
atggccaatg acctgcctcc ctatgaccca cagtgtggca tccagagtag cgaatacttc    120
caggctttgg tgaataatat gtcctttgta agatataaag aagtgtatgc cgctgcagca    180
gaagttctag gacttatact tcgatatgtt atggagagaa aaacatact ggaggagtct     240 ctgtgtgaac tggttgcgaa acaattgaag caacatcaga atactatgga ggacaagttt    300
attgtgtgct tgaacaaagt gaccaagagc ttccctcctc ttgcagacag gttcatgaat    360
gctgtgttct ttctgctgcc aaaatttcat ggagtgttga aaacactctg tctggaggtg    420
gtactttgtc gtgtggaggg aatgacagag ctgtacttcc agttaaagag caaggacttc    480
gttcaagtca tgagacatag agatgatgaa agacaaaaag tatgtttgga cataatttat    540
aagatgatgc caaagttaaa accagtagaa ctccgagaac ttctgaaccc cgttgtggaa    600
ttcgtttccc atccttctac aacatgtagg gaacaaatgt ataatattct catgtggatt    660
catgataatt acagagatcc agaaagtgag acagataatg actcccagga aatatttaag    720
ttggcaaaag atgtgctgat tcaaggattg atcgatgaga ccctggact tcaattaatt    780 attcgaaatt tctggagcca tgaaactagg ttaccttcaa ataccttgga ccggttgctg    840
gcactaaatt cctatattc tcctaagata gaagtgcact tttaagttt agcaacaaat    900 tttctgctcg aaatgaccag catgagccca gattatccaa accccatgtt cgagcatcct    960
ctgtcagaat gcgaatttca ggaatatacc attgattctg attggcgttt ccgaagtact   1020
gttctcactc cgatgtttgt ggagacccag gcctcccagg gcactctcca gacccgtacc   1080
caggaagggt ccctctcagc tcgctggcca gtggcagggc agataagggc cacccagcag   1140
cagcatgact tcacactgac acagactgca gatggaagaa gctcatttga ttggctgacc   1200
gggagcagca ctgacccgct ggtcgaccac accagtccct catctgactc cttgctgttt   1260
gcccacaaga ggagtgaaag gttacagaga gcacccttga agtcagtggg gcctgattt   1320

<210> SEQ ID NO 22
<211> LENGTH: 600
<212> TYPE: DNA
<213> ORGANISM: Artificial Sequence
<220> FEATURE:
<223> OTHER INFORMATION: cDNA sequence encoding the 2500-2700 peptide
<220> FEATURE:
<221> NAME/KEY: CDS
<222> LOCATION: (1)..(600)
<223> OTHER INFORMATION: HUMAN GENETIC ORIGIN
<220> FEATURE:
```

```
<221> NAME/KEY: misc_feature
<222> LOCATION: (325)..(327)
<223> OTHER INFORMATION: encodes T2609 residue

<400> SEQUENCE: 22
ttggcaaaag atgtgctgat tcaaggattg atcgatgaga accctggact tcaattaatt      60
attcgaaatt tctggagcca tgaaactagg ttaccttcaa ataccttgga ccggttgctg     120
gcactaaatt ccttatattc tcctaagata gaagtgcact ttttaagttt agcaacaaat     180
tttctgctcg aaatgaccag catgagccca gattatccaa accccatgtt cgagcatcct     240
ctgtcagaat gcgaatttca ggaatatacc attgattctg attggcgttt ccgaagtact     300
gttctcactc cgatgtttgt ggagacccag gcctcccagg gcactctcca gacccgtacc     360
caggaagggt ccctctcagc tcgctggcca gtggcagggc agataagggc cacccagcag     420
cagcatgact tcacactgac acagactgca gatggaagaa gctcatttga ttggctgacc     480
gggagcagca ctgacccgct ggtcgaccac accagtccct catctgactc cttgctgttt     540
gcccacaaga ggagtgaaag gttacagaga gcaccttga agtcagtggg gcctgatttt     600

<210> SEQ ID NO 23
<211> LENGTH: 1284
<212> TYPE: DNA
<213> ORGANISM: Artificial sequence
<220> FEATURE:
<223> OTHER INFORMATION: cDNA sequence encoding 2275-2702 peptide
<220> FEATURE:
<221> NAME/KEY: CDS
<222> LOCATION: (1)..(1284)
<223> OTHER INFORMATION: HUMAN GENETIC ORIGIN
<220> FEATURE:
<221> NAME/KEY: misc_feature
<222> LOCATION: (1003)..(1005)
<223> OTHER INFORMATION: encodes T2609 residue

<400> SEQUENCE: 23
caattgctag gcatcgtgat ggccaatgac ctgcctccct atgacccaca gtgtggcatc      60
cagagtagcg aatacttcca ggctttggtg aataatatgt cctttgtaag atataaagaa     120
gtgtatgccg ctgcagcaga agttctagga cttatacttc gatatgttat ggagagaaaa     180
aacatactgg aggagtctct gtgtgaactg gttgcgaaac aattgaagca acatcagaat     240
actatggagg acaagtttat tgtgtgcttg aacaaagtga ccaagagctt ccctcctctt     300
gcagacaggt tcatgaatgc tgtgttcttt ctgctgccaa aatttcatgg agtgttgaaa     360
acactctgtc tggaggtggt actttgtcgt gtggagggaa tgacagagct gtacttccag     420
ttaaagagca aggacttcgt tcaagtcatg agacatagag atgatgaaag acaaaaagta     480
tgtttggaca taatttataa gatgatgcca agttaaaaac cagtagaact ccgagaactt     540
ctgaaccccg ttgtggaatt cgtttcccat ccttctacaa catgtaggga caaatgtat      600 aatattctca tgtggattca tgataattac agagatccaa aagtgagac agataatgac     660 tcccaggaaa tatttaagtt ggcaaaagat gtgctgattc aaggattgat cgatgagaac     720
cctggacttc aattaattat tcgaaatttc tggagccatg aaactaggtt accttcaaat     780
accttggacc ggttgctggc actaaattcc ttatattctc ctaagataga agtgcacttt     840
ttaagtttag caacaaattt tctgctcgaa atgaccagca tgagcccaga ttatccaaac     900
cccatgttcg agcatcctct gtcagaatgc gaatttcagg aatataccat tgattctgat     960
tggcgtttcc gaagtactgt tctcactccg atgtttgtgg agacccaggc ctcccagggc    1020
actctccaga cccgtaccca ggaagggtcc ctctcagctc gctggccagt ggcagggcag    1080
```

```
ataagggcca cccagcagca gcatgacttc acactgacac agactgcaga tggaagaagc    1140
tcatttgatt ggctgaccgg gagcagcact gacccgctgg tcgaccacac cagtccctca    1200
tctgactcct tgctgtttgc ccacaagagg agtgaaaggt tacagagagc acccttgaag    1260
tcagtggggc ctgattttgg gaaa                                           1284
```

<210> SEQ ID NO 24
<211> LENGTH: 819
<212> TYPE: DNA
<213> ORGANISM: Artificial Sequence
<220> FEATURE:
<223> OTHER INFORMATION: cDNA sequence encoding 2429-2072 peptide
<220> FEATURE:
<221> NAME/KEY: CDS
<222> LOCATION: (1)..(819)
<223> OTHER INFORMATION: HUMAN GENETIC ORIGIN
<220> FEATURE:
<221> NAME/KEY: misc_feature
<222> LOCATION: (538)..(540)
<223> OTHER INFORMATION: encodes T2609 residue

<400> SEQUENCE: 24

```
gaaagacaaa aagtatgttt ggacataatt tataagatga tgccaaagtt aaaaccagta      60
gaactccgag aacttctgaa ccccgttgtg gaattcgttt cccatccttc tacaacatgt     120
agggaacaaa tgtataatat tctcatgtgg attcatgata attacagaga tccagaaagt     180
gagacagata atgactccca ggaaatattt aagttggcaa aagatgtgct gattcaagga     240
ttgatcgatg agaaccctgg acttcaatta attattcgaa atttctggag ccatgaaact     300
aggttacctt caaataccct tggaccggtt ctggcactaa attccttata ttctcctaag     360
atagaagtgc acttttttaag tttagcaaca aatttttctgc tcgaaatgac cagcatgagc     420
ccagattatc aaaccccat gttcgagcat cctctgtcag aatgcgaatt tcaggaatat     480
accattgatt ctgattggcg tttccgaagt actgttctca ctccgatgtt tgtggagacc     540
caggcctccc agggcactct ccagacccgt acccaggaag ggtccctctc agctcgctgg     600
ccagtggcag ggcagataag ggccacccag cagcagcatg acttcacact gacacagact     660
gcagatggaa gaagctcatt tgattggctg accgggagca gcactgaccc gctggtcgac     720
cacaccagtc cctcatctga ctccttgctg tttgcccaca agaggagtga aaggttacag     780
agagcaccct tgaagtcagt ggggcctgat tttgggaaa                            819
```

<210> SEQ ID NO 25
<211> LENGTH: 420
<212> TYPE: DNA
<213> ORGANISM: Artificial Sequence
<220> FEATURE:
<223> OTHER INFORMATION: cDNA Sequence encoding 2561-2700 peptide
<220> FEATURE:
<221> NAME/KEY: CDS
<222> LOCATION: (1)..(420)
<223> OTHER INFORMATION: HUMAN GENETIC ORIGIN
<220> FEATURE:
<221> NAME/KEY: misc_feature
<222> LOCATION: (145)..(147)
<223> OTHER INFORMATION: Encodes T2609 residue

<400> SEQUENCE: 25

```
tttctgctcg aaatgaccag catgagccca gattatccaa accccatgtt cgagcatcct      60
ctgtcagaat gcgaatttca ggaatatacc attgattctg attggcgttt ccgaagtact     120
gttctcactc cgatgtttgt ggagacccag gcctcccagg gcactctcca gacccgtacc     180
```

```
caggaagggt ccctctcagc tcgctggcca gtggcagggc agataagggc cacccagcag    240
cagcatgact tcacactgac acagactgca gatggaagaa gctcatttga ttggctgacc    300
gggagcagca ctgacccgct ggtcgaccac accagtccct catctgactc cttgctgttt    360
gcccacaaga ggagtgaaag gttacagaga gcacccttga agtcagtggg gcctgatttt    420

<210> SEQ ID NO 26
<211> LENGTH: 306
<212> TYPE: DNA
<213> ORGANISM: Artificial Sequence
<220> FEATURE:
<223> OTHER INFORMATION: cDNA sequence encoding 2600-2702 peptide
<220> FEATURE:
<221> NAME/KEY: CDS
<222> LOCATION: (1)..(306)
<223> OTHER INFORMATION: HUMAN GENETIC ORIGIN
<220> FEATURE:
<221> NAME/KEY: misc_feature
<222> LOCATION: (25)..(27)
<223> OTHER INFORMATION: Encodes T2609 residue

<400> SEQUENCE: 26
gttctcactc cgatgtttgt ggagacccag gcctcccagg gcactctcca gacccgtacc     60
caggaagggt ccctctcagc tcgctggcca gtggcagggc agataagggc cacccagcag    120
cagcatgact tcacactgac acagactgca gatggaagaa gctcatttga ttggctgacc    180
gggagcagca ctgacccgct ggtcgaccac accagtccct catctgactc cttgctgttt    240
gcccacaaga ggagtgaaag gttacagaga gcacccttga agtcagtggg gcctgatttt    300
gggaaa                                                              306

<210> SEQ ID NO 27
<211> LENGTH: 34
<212> TYPE: DNA
<213> ORGANISM: Artificial sequence
<220> FEATURE:
<223> OTHER INFORMATION: Primer to create T2609A mutation

<400> SEQUENCE: 27
tccgatgttt gtggaggacc aggcctccca gggc                                34

<210> SEQ ID NO 28
<211> LENGTH: 34
<212> TYPE: DNA
<213> ORGANISM: Artificial Sequence
<220> FEATURE:
<223> OTHER INFORMATION: Reverse primer to create T2609A mutation

<400> SEQUENCE: 28
gccctgggag gcctggtcct ccacaaacat cgga                                34
```

DNA DEPENDENT PROTEIN KINASE CATALYTIC SUBUNIT PHOSPHORYLATION SITES AND ANTIBODIES THERETO

CROSS-REFERENCE TO RELATED APPLICATIONS

This application claims priority to U.S. Provisional Patent Application No. 60/375,094, which was filed on Apr. 22, 2002, which is incorporated by reference in its entirety.

STATEMENT REGARDING SEQUENCE LISTING

Applicants assert that the attached paper copy of the Sequence Listing for the utility application, "DNA Dependent Protein Kinase Catalytic Subunit Phosphorylation Sites and Antibodies Thereto," claiming priority to U.S. Provisional Patent Application No. 60/375,094, filed on Apr. 21, 2003, is identical to the Sequence Listing in computer readable form found on the accompanying computer disk, as required by 37 CFR 1.821(c) and is hereby incorporated by reference in its entirety.

BACKGROUND OF THE INVENTION

1. Field of the Invention

This invention generally relates to the field of cancer treatment, therapeutics and diagnostics. More specifically, the invention describes antibodies and a method useful for increasing the radiation sensitivity of cancer cells. The invention also provides methods of designing inhibitors of DNA-PKcs that are more specific and result in less harmful side effects.

2. Description of the Related Art

In the clinical setting, the two most common treatments for cancer patients are a drug regimen or treatment with high doses of radiation, or a combination of both. Both approaches kill cancerous (and healthy) cells through a common mechanism of inducing DNA damage. DNA double-strand breaks (DSB) are the most common type of DNA damage resulting from either treatment. In human cells, DNA DSBs are repaired mainly by, the non-homologous end-joining pathway (NHEJ). The DNA-dependent protein kinase complex (DNA-PK) is a key player in the repair of DNA DSBs by this pathway, if DNA-PK is defective, cells are unable to repair DNA DSBs, and thus become highly sensitive to the effects of ionizing radiation and of various cancer drugs. Since DNA-PK is a protein kinase, it is able to transfer phosphate groups to target proteins, and thereby regulate their function. DNA-PK is a protein complex consisting of its DNA-binding and regulatory subunit, which is the Ku protein, and the catalytic subunit, called DNA-PKcs. In the presence of DNA DSBs, Ku binds to the ends of the DNA and recruits DNA-PKcs to the site of the DSB. Once bound to Ku and DNA, DNA-PKcs becomes activated and is capable of phosphorylating target proteins.

Although the biochemical properties of DNA-PK have been extensively studies in vitro, very little is known about how DNA-PK functions in vivo in relation to the repair of DNA DSBs. This lack of progress in studying the physiological functions of DNA-PK is in part due to the unavailability of the right tools or assays to evaluate DNA-PK in vivo activity. Currently, one of the most commonly used methods to study DNA repair proteins is by immunofluorescence with an antibody to the protein of interest. In response to DNA damage, many of the DNA repair proteins form "foci" that can be visualized with antibodies. It is generally believed that these DNA damage-induced foci correspond to sites where the damages DNA is actively being repaired.

It is currently not possible to detect DNA-PK foci with the antibodies available because DNA-PK is quite abundant in the nucleus, thus when one performs immunofluorescence with any of the available antibodies, the entire nucleus will produce a signal, making it impossible to see any discernable foci. Therefore, it is of interest to develop an antibody that can overcome the problem associated with a very high background signal and can recognize the phosphorylated form of DNA-PKcs when bound to site of DNA DSBs.

DNA-PK is a serine/threonine protein kinase that in vitro is activated by DNA ends and has long been established to play an important role in the repair of DNA double-strand breaks (DSB) by the NHEJ pathway (Smith and Jackson, *Genes Dev.* 1999 Apr. 15;13(8):916-34). DNA-PK is capable of autophosphorylating the two Ku subunits, Ku70 and Ku80 according to Chan et al., *Biochemistry* 1999 Feb. 9;38(6): 1819-28. Autophosphorylation of DNA-PKcs causes it to dissociate from Ku, resulting in the loss of kinase activity (Chan and Lees-Miller, J Biol Chem. 1996 Apr. 12;271(15): 8936-41). in addition, the inventors have shown that the kinase activity of DNA-PKcs is absolutely required for its function in the NHEJ pathway since a DNA-PKcs-deficient CHO cell line expressing a kinase dead form of DNA-PKcs was incapable of repair (Kurimasa et al., *The Journal of Immunology*, 2000, 165: 3883-3889). Therefore, the kinase activity of DNA-PK is absolutely required for the repair of DNA DSBs; however, the molecular mechanism of this requirement for kinase activity remains to be elucidated. DNA-PK is also capable of autophosphorylation, that is, it transfers phosphate groups onto itself, and that autophosphorylation may be an important mechanism for regulating its kinase activity (Kurimasa et al., *Molecular and Cellular Biology*, May 1999, p. 3877-3884, Vol. 19, No. 5).

DNA-PKcs is an extremely large protein consisting of 4129 amino acids, and therefore identifying the site of autophosphorylation is comparable to finding a very small needle in a large haystack. Cloning of the DNA-PKcs cDNA is difficult, since the cDNA exceeds 13 kb. In the past, using classical biochemical techniques, several labs have attempted but failed to identify the autophosphorylation sites. For example, in vivo radiolabelling with $^{32}P$ and 2-dimensional phosphopeptide mapping failed to identify any autophosphorylation sites.

One goal of radiation biology is to find ways to increase the radiation sensitivity of cancer cells. If this could be achieved, it would then be possible to treat cancer patients with lower doses of radiation and thereby dramatically decrease the side effects and complications associated with radiation treatment.

If the site of phosphorylation in DNA-PK could be specifically blocked in cancer cells, for example with a DNA-PKcs inhibitor, then this should inhibit DNA-PKcs-mediated repair of DNA DSBs and thereby increase the radiation sensitivity of the treated cancer cells. Another possible means of increasing radiation sensitivity is the development of therapeutic antibodies that can specifically recognize and bind to the phosphorylated protein.

BRIEF SUMMARY OF THE INVENTION

The present invention is directed to the identification and use of two major DNA-PKcs autophosphorylation sites, Threonine (T) 2609 and Serine (S) 2056, including antibodies specific for phosphorylated T2609 and S2056. It is demonstrated that phosphorylation of these sites, carried out in vivo by the DNA-PKcs itself (i.e. autophosphorylation), is required for DNA-PK activity and, furthermore, that such activity repairs double strand DNA breaks (DSBs) and improves cell survival to ionizing radiation (IR). For example, it is demonstrated a point mutation at position 2056 from serine to alanine and position 2609 from threonine to alanine results in cells that are radiosensitive.

The present invention further provides phosphospecific antibodies that recognize these specific sites of phosphorylation in DNA-PKcs. The antibodies do not bind to the unphosphorylated DNA-PKcs protein or peptide. This provides diagnostic tools based on the ability to identify the phosphorylation status of the DNA-PKcs autophosphorylation sites. One can monitor the effectiveness of treatments which target the DNA repair pathway of cancer cells, such as radiation treatment and inhibitor drugs. Also, the ability to intervene in autophosphorylation of T2609 or S2056, either through application of a drug or an antibody, would increase the radiation-induced killing of cancer cells.

In one embodiment there is provided an antibody which specifically binds to an epitope defined by at least a ten amino acid sequence from DNA-PKcs and comprising a phosphorylated threonine at position T2609 in human DNA-PKcs, which antibody does not bind when T2609 is not phosphorylated. The antibody may be an affinity purified polyclonal antibody or a monoclonal antibody. The monoclonal may be a conventional hybridoma produced mouse monoclonal, or may be a human monoclonal produced by known techniques. In one embodiment, the human monoclonal is produced using a mouse with a human immune system as an immune cell donor in a hybridoma process. One specific embodiment is the pT2609 monoclonal antibody, pT2609mAb.

The invention further comprises an antibody which specifically binds to an epitope defined by at least a ten amino acid sequence from DNA-PKcs and comprising a phosphorylated serine at position S2056 in human DNA-PKcs, which antibody does not bind when S2056 is not phosphorylated. Again, the antibody may be an affinity purified polygonal antibody or a monoclonal.antibody. The monoclonal may be a conventional hybridoma produced mouse monoclonal, or may be a human monoclonal produced by known techniques. In one embodiment, the human monoclonal is produced by using a mouse with a human immune system as an immune cell donor in a hybridoma process. One specific embodiment is the pS2056 monoclonal antibody, pS2056mAb.

In any case, the binding epitope is contained both on full length DNA-PKcs and subsequences thereof, said subsequences having at least about 10 amino acids.

The present invention further comprises methods for determining the ability of a test compound to block phosphorylation of human DNA-PKcs. One method comprising the following steps: (a) providing a sample containing a DNA-PKcs peptide fragment capable of being phosphorylated; (b) adding the test compound to the sample; (c) inducing phosphorylation of the DNA-PKcs protein in the sample; and (d) measuring the resulting phosphorylation of DNA-PKcs at T2609 or S2056 in the presence of the test compound. This is preferably done in comparison to a sample containing a DNA-Pcs peptide fragment which is phosphorylated in the absence of the test compound.

The method may also involve providing a sample containing an artificial peptide containing the T2609 and/or S2056 site. Recombinant DNA-PK or DNA-PKcs is added to the mixture and will phosphorylate the artificial peptide. The artificial peptide may be on the order of about 1000 amino acids long or as short as 20 amino acids long.

The measuring step may be carried out by measuring the binding of an antibody which specifically binds to an epitope comprising either or both of (a) a phosphorylated serine at position S2056 in human DNA-PKcs or (b) a phosphorylated threonin at position T2609 in human DNA-PKcs Known kinase inhibitors provide suitable starting points for assaying test compounds that are capable of blocking or inhibiting phosphorylation of DNA-PKcs. In this assay, test compounds are any organic molecules that are capable of blocking or inhibiting phosphorylation of DNA-PKcs. Non-limiting examples include wortmannin, substituted or unsubstituted imidazoles, pyrazoles, benzofluoranthenes, thiazoles, isoquinolinones, dihydrolisoquinolinones, phthalazinones and related compounds and derivatives thereof. For example, since wortmannin has been shown herein to inhibit the phosphorylation of T2609 and S2056, derivatives and analogs of wortmannin provide sources of test compounds to be tested in the present assay. Functional groups could be introduced into the wortmannin structure adjacent to the heterocyclic oxygen adjacent to C21 or the double bond between C4 and C21.

To identify drug inhibitors of DNA-PK, one first initially screens available chemical libraries for test compounds that could inhibit DNA-PK kinase activity in vitro or organic molecules that are capable of blocking or inhibiting phosphorylation of DNA-PKcs. The compounds in these chemical libraries can be added to in vitro DNA-PK kinase assays to identify, the ones that could inhibit DNA-PK activity. Because phosphorylation of T2609 and S2056 is via an autophosphorylation mechanism, it can be speculated that any drug compounds that inhibit the kinase activity will inhibit the autophosphorylation of these two sites. Once these compounds have been identified, cellular studies can then be carried out to evaluate their efficacy.

Further aspects of the present invention involve phosphopeptides that have been prepared for use in injection into animals in the course of antibody preparation (haptens) or for use as artificial phosphorylation substrates. These peptides will have less than 30 amino acids and comprise SEQ ID NO: 1 or SEQ ID NO: 2, or sequences having at least 90% homology thereto having the requisite serine or threonine residues, preferably in an SQ or TQ sequence. These phosphopeptides may also have an amino acid other than the wild type T2609 or S2056, to serve as negative controls.

The above described isolated peptides have further utility when T2609 and/or S2056 is replaced by an amino acid which is not phosphorylated, such as: Valine, Alanine, Glycine, or Leucine. These embodiments serve as negative controls and will inhibit phosphorylation.

The above described peptides may be encoded by an isolated polynucleotide cloned and inserted into a suitable host vector.

The present invention further comprises a method of measuring radiosensitivity of cells in a subject undergoing radiation treatment. This method comprises the steps of (a) providing a cell sample from said subject and containing DNA-PKcs, for example a blood sample or a tissue sample from the irradiated area (e.g. a nuclear extract may be prepared from this sample); (b) adding to said sample a labeled antibody which binds to phosphorylated residue T2609 or phosphorylated residue S2056 but not the unphosphorylated residues; (c) removing unbound antibody from the sample, such as by washing, as is known in the art; and (d) measuring the degree of phosphorylation of the DNA-PKcs by determining the amount of antibody bound to the DNA-PK in the sample. The degree of antibody binding to DNA-PKcs in the cell sample correlates to the degree of phosphorylation, a higher degree of phosphorylation indicating less radiation sensitivity Since most treatment for cancer entails inducing DNA damage, a pT2609 or pS2056 antibody can be a very useful diagnostic tool for determining the efficacy of the treatment. For example, the antibody can be used to confirm that the cancer treatment is indeed causing DNA damage in the cancer cells; conversely, the antibody can be used to determine the effects of the treatment on healthy cells.

DETAILED DESCRIPTION OF THE PREFFERRED EMBODIMENT

A. Definitions

Figure 1:
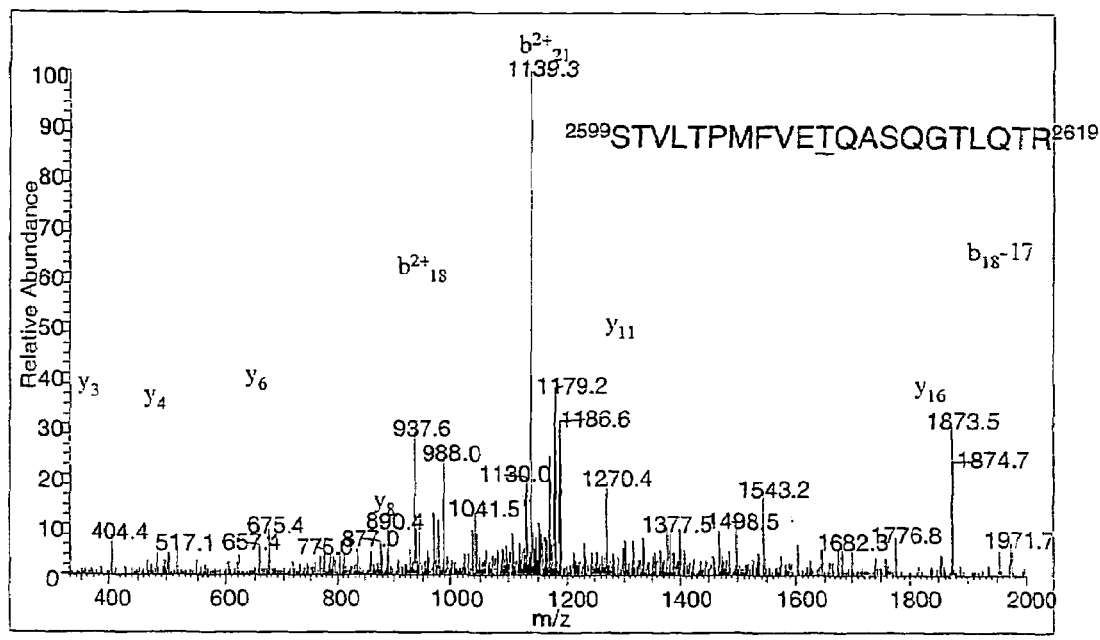
FIG. 1 is a mass spectra of sequencing of the in vitro phosphorylated DNA-PKcs peptide that was first identified by MALDI-TOF mass spectrometry. The plot shows a plot of relative intensity vs the mass-to-charge ratio (m/z) of the phosphorylated peptide having the shown sequence from 2599 to 2619. Assignment of all the mass spectra peaks unequivocally identify T2609 as the site of phosphorylation.

"Radiosensitization" herein refers to a means of increasing the sensitivity of human cells to the effects of ionizing radiation and cancer drugs that induce DNA double-strand breaks (DSBs). By increasing the radiosensitivity of cancer cells, patients can be treated with lower doses of radiation or chemotherapeutic regimen and thereby decrease the harmful side effects of the treatment.

"Gy" herein refers to describe the unit (SI unit) of absorbed dose of radiation (Gy), wherein 1 Gy=1 J kg$^{-1}$=100 rad.

"Epitope" has its conventional meaning, i.e. a single antigenic determinant. Functionally it is the portion of an antigen (e.g. a PKcs peptide) which combines with the antibody paratope. Structurally, it is the specific amino acid residues or portions thereof to which an anti-peptide antibody binds.

"DNA-PKcs" herein refers to DNA-dependent protein kinase catalytic subunit (EC 2.7.1.37), preferably human DNA-PKcs. As used herein, the numbering is based on GenBank Accession Number P78527, as set out in SEQ ID NO: 3. Specifically, T2609 is threonine 2609 in Genbank Accession Number P78527. S2056 is serine 2056 in GenBank Accession Number P78527. DNA-PK refers to the entire enzyme. DNA-PKcs is encoded by the nucleotide sequence as set out in SEQ ID NO: 15, having GenBank Accession Number U47077.

"Monoclonal antibody" has its conventional meaning, and is explained more fully in U.S. Pat. No. 4,619,895, hereby incorporated by reference for purposes of describing preparation and characterization of mouse monoclonal antibodies. U.S. Pat. No. 4,744,982 hereby incorporated by reference for purposes of describing human/human monoclonal antibody preparation and characterization, U.S. Pat. No. 5,874,540, hereby incorporated by reference for purposes of describing the preparation and characterization of CDR-grafted humanized antibodies, and U.S. Pat. No. 6,075,181, hereby incorporated by reference for purposes of describing the preparation and characterization of human antibodies derived from immunized xenomice.

The abbreviation "mAb" herein refers to monoclonal antibodies and the abbreviation "pAb" herein refers to polyclonal antibodies.

"Humanize," when applied to antibodies, herein refers to methods of generating human monoclonal antibodies, as exemplified by van de Winkel, in U.S. Pat. No. 6,111,166, hereby incorporated by reference for purposes of describing such methods.

"Isolated," when applied to a polynucleotide, herein refers to that the polynucleotide has been removed from its natural genetic milieu and is thus free of the extraneous or unwanted coding sequences, and is in a form suitable for use within genetically engineered protein production systems. Such isolated molecules are those that are separated from their natural environment and include cDNA, synthetic DNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

"Isolated," when applied to a polypeptide or protein, herein refers to a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

"Polynucleotide" herein refers to a single- or double-stranded polymer of deoxyribonucleotide or ribonucleotide bases read from the 51 to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

"Polypeptide" herein refers to a polymer of amino acid residues joined by peptide bonds, whether produced naturally or synthetically. Polypeptides of less than about 10 amino acid residues are commonly referred to as "peptides".

"Homologous" herein refers to the sequence similarity between two polymeric molecules, e.g., between two nucleic acid molecules, e.g., two DNA molecules or two RNA molecules, or between two peptide molecules. When a subunit position in both of the two molecules is occupied by the same monomeric subunit, e.g., if a position in each of two DNA molecules is occupied by adenine, then they are homologous at that position. The homology between-two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGCG 5' share 50% homology. Any of a variety of known algorithms may be used to calculate the percent homology between two nucleic acids or two proteins of interest and these are well-known in the art.

"Substantial homology" or "substantial identity", when referring to polypeptides, herein refers to that the polypeptide or protein in question exhibits at least about 30% identity using BLASTP (Altschul, S. F., Gish, W., Miller, W., Myers, E. W. & Lipman, D. J. (1990) "Basic local alignment search tool." J. Mol. Biol. 215:403-410) with an entire naturally-occurring protein or a portion thereof, usually at least about 70% identity over the common lengths, more usually at least about 80% identity, preferably at least about 90% identity, and more preferably at least about 90% identity or 90% positive, whichever is less. For purposes of calculating homology between two polypeptides, the standard BLASTP 2.2.5 defaults are used, namely "Expect 10," "Word size 3," "BLOSUM62 Matrix" and "Gap Costs Existence10, Extension 1."

In this specification, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

B. Role of DNA PK-cs in Double Strand Break Repair

Repair of DNA double strand breaks (DSBs) in mammalian cells is mainly mediated by the non-homologous end-joining pathway (NHEJ). The DNA-dependent, protein kinase (DNA-PK) complex play critical roles in the NHEJ pathway since mammalian cell lines that lack components of the complex show severe radiation sensitivity and DNA repair defects. DNA-PK is a serine/threonine protein kinase that is activated by the DNA ends in vitro and is composed of the DNA-binding and regulatory subunit, Ku, and the catalytic subunit, DNA-PKcs. DNA-PK kinase activity is required for the repair of DNA DSBs in vivo (Kurimasa et al., *Mol Cell Biol.* May 1999; 19(5):3877-84). Previously, it was demonstrated that DNA-PK activity is negatively regulated by an autophosphorylation mechanism in vitro. (Chan et al., *Biochem Cell Biol* 74: 67-73, 1996).

In the preferred embodiment, the DNA-PKcs being investigated has an amino acid sequence comprising SEQ ID NO: 3 and wild-type cDNA sequence comprising SEQ ID NO: 15.

Herein is reported the method and identification of residues of DNA-PKcs which can act as major in vitro and in vivo autophosphorylation sites.

C. Autophosphorylation Sites in DNA-PKcs

Determination of autophosphorylation sites in DNA-PKcs is preferably done by mass spectrometry. For example, purified DNA-PKcs and Ku can be autophosphorylated by adding a low concentration of ATP to allow phosphorylation of the most preferential site and then the autophosphorylated DNA-PKcs was analyzed by mass spectrometry. Alternatively, DNA-PKcs can be immunoprecipitated from nuclear extracts prepared from irradiated HeLa cells and then analyzed by mass spectrometry.

As described below, two major in vitro and in vivo autophosphorylation sites of the residues of T2609 and S2056 were identified by mass spectrometry. Purified DNA-PKcs and Ku were autophosphorylated with low concentration of ATP (50 uM) to allow phosphorylation of the most preferential site. Referring now to FIG. 1, the in vitro autophosphorylated DNA-PKcs was analyzed by mass spectrometry and T2609 was unambiguously identified as a major site of autophosphorylation. T2609 lies in a region of DNA-PKcs that is not conserved between the various members of the phosphatidylinositol 3-kinase (PI-3) family members, to which DNA-PKcs is a member of. However, T2609 was absolutely conserved in all known DNA-PKcs homologues found in GenBank (i.e. mouse, dog, horse, chicken and xenopus) when the sequences are compared. This suggests the significance of the phosphorylation of this residue and that phosphorylation of DNA-PKcs at this residue maybe be conserved throughout evolution.

Figure 2:
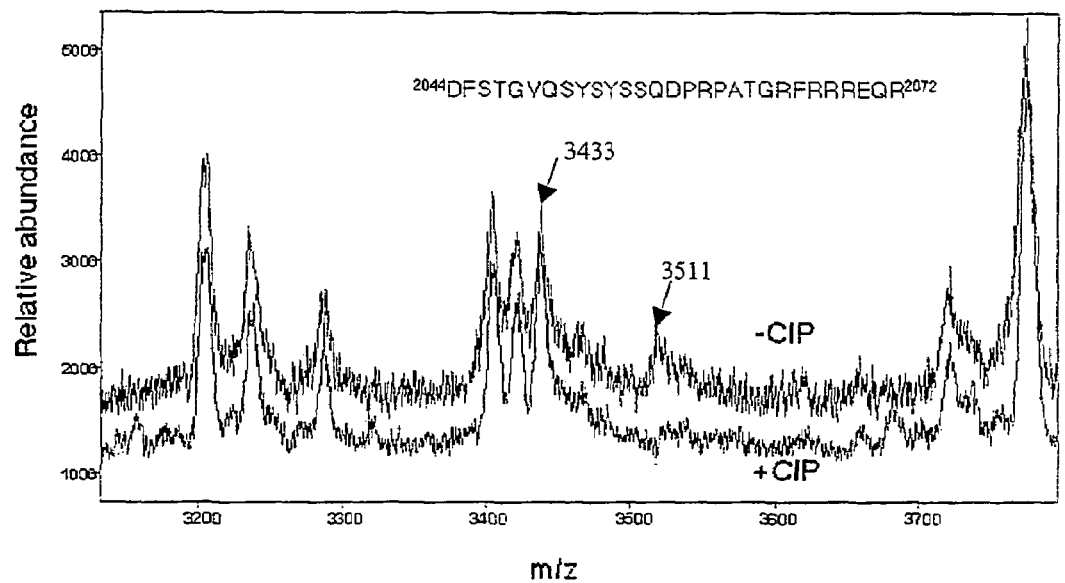
FIG. 2 is the mass spectra of phosphatase-treated (bottom trace) and the mock treated (top trace) DNA-PKcs peptides from irradiated HeLa cells which were purified by immuno-precipitation and digested with Asp-N protease, then analyzed by MALDI-TOP mass spectrometry. The loss of the peak with the m/z of 3511 with phosphatase treatment, and the presence of the peak corresponding to the unphosphorylated peptide (m/z of 3433) allowed the positive assignment of a phosphorylation site to the sequence of DNA-PKcs between amino acids 2044-2072.

Referring now to FIG. 2, a second major in vitro and in vivo autophosphorylation site of DNA-PKcs, S2056, was identified by immunoprecipitating DNA-PKcs from nuclear extracts prepared from irradiated HeLa cells and analyzed by mass spectrometry. As described in detail below, mass spectrometry identified the following phosphopeptide sequence, DFSTGVQSYSYSSQDPRPATGRFRRREQR (SEQ ID NO: 5), which corresponds to amino acids 2044 to 2072 of DNA-PKcs (S2056 is underlined). Upon careful analysis of the sequence, S2056 proved to be the Site of phosphorylation. This is consistent with prior suggestions that DNA-PK preferentially phosphorylates "SQ" and "TQ" sequences and S2056 followed this "SQ" consensus sequence. Similar to T2609, the sequence alignment with other vertebrate DNA-PKcs homologues in GenBank shows that amino acids 2044 to 2056 in DNA-PKcs are highly conserved throughout evolution in vertebrates.

D. Role of DNA-PKcs Autophosphorylation Sites in Radiation Sensitivity

To investigate the biological significance of the autophosphorylation of these DNA-PKcs sites in relation to DNA repair, wild-type or mutant DNA-PKcs having the site of autophosphorylation mutated were transfected into the DNA-PKcs-defective V3 cell line (Kurimasa et al., *J Immunol.* 2000 Oct. 1;165(7):3883-9). The resulting V3 cell lines were isolated and evaluated for DNA-PKcs protein expression levels, radiation sensitivity, and DNA repair defects. Cells expressing the mutant DNA-PKcs protein exhibit a more severe radiation sensitivity phenotype as compared with wild-type DNA-PKcs protein yet not as severe as the V3 cell line that totally lacks DNA-PKcs. The V3-mutant DNA-PKcs cells exhibits a radiation sensitivity phenotype of about a 10 fold increase in cell death at 5 Gy when compared with V3-wild type cells, demonstrating a dramatic difference in radiation sensitivity in mammalian cells.

E. Generation of Anti-pT2609 and Anti-pS2056 Phosphospecific Antibodies

To study the in vivo phosphorylation status of DNA-PKcs at the autophosphorylation sites, a phosphspecific antibody that recognizes the phosphorylated residue of DNA-PKcs is generated, then affinity purified to insure specificity.

DNA-PKcs phosphospecific antibodies can be made by a number of methods known in the art. These phosphospecific antibodies include antibodies which recognize phosphorylated T2609, herein referred to as pT2609 antibodies and phosphorylated S2056, herein referred to as pS2056 antibodies. A preferred method is by generating phosphopeptides. These phosphopeptides can be synthesized or produced by first amplifying and cloning cDNA fragments of SEQ ID NO: 15, the cDNA sequence of human DNA-PKcs (GenBank Accession No. U47077), and then expressing peptide fragments of DNA-PKcs from the cloned cDNAs. These phosphopeptide fragments include the site of autophosphorylation and the adjacent DNA-PKcs amino acid sequence on either side of the position being autophosphorylated. It is preferred that at least 6, preferably no more than 10 amino acids of the wild-type DNA-PKcs protein sequence are used on either side of the phosphorylation site to generate very specific antibodies. Two such preferred phosphopeptides are SEQ ID NO: 1 and 2 and shown below.

SEQ ID NO: 1 N'--PMFVET*QASQGTC--C' (* indicating phospho group at T2609)
SEQ ID NO: 2 N'--QSYSYSS*QDPRPAC--C' (* indicating phospho group at S2056)

Since synthesized phosphopeptides are not always immunogenic on their own, the peptides were conjugated to a carrier protein before use. Appropriate carrier proteins include, but are not limited to, Keyhole limpet hemacyanin (KLH), bovine serum albumin (BSA) and ovalbumin (OVA). The conjugated phosphopeptides should then be mixed with adjuvant and injected into a mammal, preferably a rabbit through intradermal injection, to elicit an immunogenic response. Samples of serum can be collected and tested by ELISA, assay to determine the titer of the antibodies and then harvested.

Polyclonal pT2609 and pS2056 antibodies can be purified by passing the harvested antibodies through an affinity column. However, monoclonal antibodies are preferred over polyclonal antibodies and can be generated according to standard methods known in the art of creating an immortal cell line which expresses the antibody.

Nonhuman antibodies are highly immunogenic in human thus limiting their therapeutic potential. In order to reduce their immunogenicity, nonhuman antibodies need to be humanized for therapeutic application. Through the years, many researchers have developed different strategies to humanize the nonhuman antibodies. One such example is using HuMAb Mouse® HuMAb Mouse® technology available from MEDAREX, Inc. (Princeton., N.J.). is a strain of transgenic mice that harbors the entire human immunoglobin (Ig) loci and thus can be used to produce fully human monoclonal pT2609 and pS2056 antibodies.

Immunoblotting using the phosphospecific antibodies of the invention with unphosphorylated DNA-PKcs should not produce a detectable signal at preferably 0.5-10 fold molar excess (relative to the phosphorylated DNA-PKcs), more preferably at 50 fold molar excess and most preferably no signal is detected at even 100 fold molar excess.

F. Designing and Making DNA-PKcs Inhibitor Drugs

The phosphorylation of DNA-PKcs at Threonine 2609 and Serine 2056 is required for the repair of DNA double strand breaks. By inhibiting the phosphorylation of these two sites with small molecules, it may be possible to increase the radiation-induced killing of cancer cells.

To identify drug inhibitors of DNA-PK, one first initially screens available chemical libraries for test compounds that could inhibit DNA-PK kinase activity in vitro or organic molecules that are capable of blocking or inhibiting phosphorylation of DNA-PKcs. Analysis of known kinase inhibitors provides suitable starting points and non-limiting examples, include wortmannin, substituted or unsubstituted imidazoles, pyrazoles, benzofluoranthenes, thiazoles, isoquinolinones, dihydrolisoquinolinones, phthalazinones and related compounds and derivatives thereof. The compounds in these chemical libraries can be added to in vitro DNA-PK kinase assays to identify the ones that could inhibit DNA-PK activity. Because phosphorylation of T2609 and S2056 is via an autophosphorylation mechanism, it can be speculated that any drug compounds that inhibit the kinase activity will inhibit the autophosphorylation of these two sites. Once these compounds have been identified, cellular studies can then be carried out to evaluate their efficacy.

Amino acid peptide fragments of DNA-PKcs around the T1609 and S2056 sites were expressed in *E. coli* despite the difficulty encountered in cloning the corresponding cDNA sequence. In a preferred embodiment, the DNA-PKcs cDNA clones containing SEQ ID NO: 18. and SEQ ID NO: 22, which express peptide fragments corresponding to the amino acid sequence of DNA-PKcs from residues 1879-2182 and from 2500-2700 respectively, are made. In another preferred embodiment, an 822 amino acid fragment (residues 1879-2700) can be expressed from a cDNA clone containing SEQ ID NO: 20 because this fragment once expressed encompasses both phosphorylation sites.

These fragments which encompass one of or both phosphorylation sites can be made by amplifying the appropriate, cDNA sequence from a full-length DNA-PKcs cDNA (SEQ ID NO: 15, GenBank Accession No. U47077) by PCR, then, cloning and expressing the cDNA sequence to generate the peptide fragment. Primers can be designed and made from SEQ:ID NO: 15. It is preferred that the peptide fragment containing the phosphorylation site, be of a length of at least 10, preferably 100, and more preferably about 1000 amino acids or the DNA-PKcs protein sequence.

In one embodiment, these fragments can be used to test how effectively potential drugs inhibit the phosphorylation and activation of DNA-PKcs. Recombinant fragments containing these two phosphorylation sites can be used as molecular targets for small molecular screening. Specifically, small molecules which can bind to these fragments with high affinity will be identified. The inhibition capability of these small molecules can be verified by their ability to block T2609 and S2056 phosphorylation. The radiation sensitization ability of these small molecules can then verified in human cells upon radiation damage.

In addition, fragments that may also be useful can be expressed from the following clones. These clones were made to express the following residues of DNA-PKcs from the indicated corresponding cloned cDNA sequence: 1879-2182 cDNA (SEQ ID NO: 18), 1879-2267 cDNA (SEQ ID NO: 19), 2261-2700 cDNA (SEQ ID NO: 21), 2275-2702 cDNA (SEQ ID NO: 23), 2429-2702 cDNA (SEQ ID NO: 24), 2561-2700 cDNA (SEQ ID NO: 25), and 2600-2702 cDNA (SEQ ID NO: 26).

G. Peptide Inhibitor Drugs

One embodiment is to use the antibodies of the invention for use as an inhibitor of the phosphorylation and thereby block DNA repair which results in radiosensitization of cancer cells. Because of the specificity of the pT2609 and pS2056 antibodies of the invention, only the sites of phosphorylation are inhibited. Furthermore, phosphorylation of T2609 and S2056 occurs only in cells that have been irradiated and suffer DNA damage. Therefore, the use of the antibodies, or peptide fragments thereof, as DNA repair inhibitors will not affect other proteins or even other parts and functions of the DNA-PKcs protein. This specificity will result in not only radiosensitizing cancer cells, but also this antibody will reduce the other harmful side effects of inhibiting all DNA-PKcs function.

If phosphorylation of T2609 is required for the recruitment of other proteins needed at the site of DNA DSBs, then another means of disrupting this step is to overexpress a small polypeptide spanning the region that surrounds T2609 or S2056 with an Aspartic acid mutation to simulate the phosphorylated state and create a "dominant negative" effect. Therefore, in another embodiment, a polypeptide, such as the peptides generated in Example 2, made with an Aspartic acid or other similarly negatively charged amino acid substituted at residue 2609 or 2056 to mimic the phosphorylated state of T2609, can be overexpressed or administered to compete with endogenous phosphorylated DNA-PKcs. This would "squelch" DNA-PKcs function and therefore lead to an increase in radiation sensitivity.

H. Diagnostic Tools for Detecting Efficacy of Therapeutic Treatments

Companies are developing specific inhibitors for DNA-PKcs or Ku for the purpose of sensitizing cancer cells for radiation therapy. Currently, there is no efficient way to estimate the amount of the inhibitors to be used for sensitization. Antibodies against T2609 or S2506 can be used as a diagnostic tool to effectively monitor blood samples in the test tube to estimate the dose to be used to effectively block the autophosphorylation of DNA-PKcs. The present pT2609 or pS2056 antibodies can provide a diagnostic tool for determining the efficacy of treatment using DNA-PKcs or Ku inhibitors. The antibodies of the invention can be used to confirm whether the cancer treatment the patient is undergoing is indeed causing DNA damage in the cancer cells; conversely, the antibody can be used to determine the effects of the treatment on healthy cells. Furthermore, diagnostic tests to test the efficacy of inhibitors during drug development can be made based on observations of phosphorylation of T2609, such as in Example 6 or 8.

In one embodiment, the antibodies of the invention can be used to determine the correct radiation dosage for each patient. The normal patient dosage is 2 Gy/day up to 50 Gy/day. Since every cancer patient responds to radiation therapy differently, the pT2609 and pS2056 antibodies can be a very useful tool to monitor the effectiveness of the cancer treatment. In a specific embodiment, for example, a small blood sample is drawn from a cancer patient and a quick radiation pulse is applied to the sample to induce DNA damage, then contacting a small volume of the radiated blood with the antibodies of the invention. To increase the signal, the antibodies can be conjugated to another antibody or other means of detection used. Unbound antibodies are washed from the sample and antibodies bound to the patient's DNA-PKcs are measured. A large signal as compared to a control will indicate to an oncologist that any inhibitors that target DNA-PKcs are not working and not inhibiting DNA repair. That is, there is a high degree of DNA-PK autophosphorylation. A low or no signal would indicate that the inhibitors are working which has resulted in the radiosensitization of cancer cells. Alternatively, the blood sample is not irradiated but taken from a patient following radiation treatment to monitor the radiation therapy. In addition, the cells may be taken from a biopsy of the patient's tumor or cancer cells.

In another embodiment, the peptide fragments of SEQ ID NOS: 4-14, would permit the screening of small molecular inhibitors to block phosphorylation at these sites. Small molecular inhibitors which would block the phosphorylation at T2609 or S2506 would be more effective radiosensitizers and have less side effects for radiotherapy. The reason is that the phosphorylation of these two sites only occurs after radiation or DNA damage in response to DSBs and only activated in DNA double-strand break repair. Therefore, inhibitors which are specific for these two sites should not have any effect in cells which have not been irradiated.

EXAMPLE 1

Determining T2609 and S2056 Sites of Autophosphorylation in DNA-PKcs by Mass Spectrometry First, purified human DNA-PKcs and Ku were autophosphorylated as previously described (Chan and Lees-Miler, *J Biol Chem* 271: 8936-8941, 1996), and hereby incorporated by reference, with the following change: 50 μM ATP was used instead of 250 μM to allow phosphorylation of the most preferential site. Purified DNA-PKcs and Ku proteins were preincubated at 30° C. Reactions contained 25 mM Hepes, pH 7.5. 75 mM KCl, 10 mM MgCl, 1 mM dithiothreitol, 0.2 mM EDTA, 0.1 mM EDTA plus 10 μg/ml sonicated calf thymus DNA, and 0.25 mM ATP containing stabilized [-P] ATP (Sigma Chemicals, St. Louis, Mo.) (specific activity. 500-1000 dpm/pmol) and were started by the addition of purified DNA-PK proteins (usually 0.05-0.1 μg as indicated). Reactions were at 30° C. for 5-10 min and DNA-PK activity was calculated as nmol of phosphate incorporated into the peptide substrate per minute per milligram of protein. Unlabeled ATP or the nonhydrolyzable ATP analogue AMP-PNP (Sigma Chemicals, Stl. Louis, Mo.) were present where indicated at 50 µM. After 0-10 min, aliquots were removed and analyzed by SDS-PAGE. The band corresponding to phosphorylated DNA-PKcs was excised and digested with trypsin.

The tryptic DNA-PKcs fragments were analyzed by mass spectrometry as previously described by Zhang et al., *Anal Chem* 70: 2050-2059, 1998. This procedure facilitates the identification of precise phosphorylation sites in proteins separated by polyacrylamide gel electrophoresis by a combination of matrix-assisted laser desorption/ionization time-of-flight mass spectrometry (MALDI/TOF) and on-line capillary liquid chromatography electrospray tandem ion trap mass spectrometry (LC/ESI/MS/MS).

To identify the DNA-PKcs in vitro T2609 phosphorylation site, purified DNA-PK was in vitro autophosphorylated under the conditions described above and analyzed by SDS PAGE. To identify the in vivo S2056 DNA-PKcs phosphorylation site, 10 L of HeLa S3 cells were irradiated with 25 Gy of ionizing radiation. Nuclear extracts made from the irradiated cells and immunoprecipitated, according to the method described in Example 3, with the 25-4 monoclonal antibody to DNA-PKcs (NeoMarkers, Lab Vision, Fremont, Calif.) and analyzed by SDS PAGE. All chemicals in this analysis were obtained from Fisher Scientific (Pittsburgh, Pa.).

The coomassie blue-stained DNA-PKcs bands were excised from the gel and destained with 50 mM $NH_4CO_3$ in 50% methanol. Once destained, the gel slices were fixed overnight with 10% acetic acid and 50% methanol. The gel slices was then swelled with water for 2 hr and grounded to a fine powder in 10 µL of 50 mM $NH_4HCO_3$. Trypsin (Roche Diagnostics, Alameda, Calif.) was added and the samples were incubated at 37° C. for 90 min. The digested peptides were extracted from the gel with acetonitrile and concentrated by centrifugation with SpeedVac. A portion of the dried peptides was redissolved in 50 mM $NH_4CO_3$ for digestion with Asp-N protease (Roche Diagnostics, Alameda, Calif.) at 37° C. for 90 min and dried. The dried tryptic and tryptic-Asp N peptides were dissolved in 10 µL of 50% acetonitrile for further processing. A portion of the sample was treated with calf intestine phosphatase (CIP) (New England Biolabs, Beverly, Mass.) in 50 mM $NH_4CO_3$ at 37° C. for 90 min and dried by centrifugation in a SpeedVac. The dried peptides were redissolved in 2 µL of 50% acetonitrile for MAIDI-TOF mass spectrometry.

The CIP-treated and untreated peptides were analyzed in a Voyager DE. MALDI-TOF system from Perspective Biosystems. Most of the peaks in the spectrum of the tryptic digest could be easily assigned to unique peptides predicted from the protein sequence and to peptides formed by autolysis of trypsin. Peaks that could not be accounted for in this way were candidates for modified peptides, and those peptides having observed masses that were 80 Da (or multiples of 80 Da) higher than that calculated for a predicted tryptic peptide were tentatively assigned as phosphopeptides. This assignment was confirmed by the absence of these peaks from the MALDI/TOF spectrum of the same peptide mixture after treatment with CIP and the appearance of new peaks that are 80 Da (or multiples of 80 Da) lower in mass. Once the phosphorylated peptide was identified, it was then analyzed on an electrospray ion trap mass spectrometer (LCQ, Finnigan MAT, San Jose, Calif.) coupled on-line with a capillary HPLC (Magic 2002, Michrom BioResources, Auburn, Calif.) to identify the phosphorylation sites in the phosphorylated peptides.

Referring now to FIG. 1, there is shown the mass spectra of one of the tryptic fragments. FIG. 1 is a mass spectra of sequencing of the in vitro phosphorylated DNA-PKcs peptide that was first identified by MALDI-TOF mass spectrometry. The plot shows a plot of relative intensity vs the mass-to-charge ratio (m/z) of the phosphorylated peptide having the sequence (shown in the Figure) from 2599 to 2619. Assignment of all the mass spectra peaks unequivocally identify T2609 as the site of phosphorylation. Thus, T2609 was unambiguously identified as a major site of autophosphorylation (FIG. 1).

Referring now to FIG. 2, a second major in vitro and in vivo autophosphorylation site of DNA-PKcs, S2056, was identified by immunoprecipitating DNA-PKcs from nuclear extracts prepared from irradiated HeLa cells and analyzing by mass spectrometry (FIG. 2). DNA-PKcs from irradiated HeLa cells was purified by immunoprecipitation and digested with Asp-N protease. The peptide mixture was treated or mock treated with alkaline phosphatase and analyzed by MALD-TOF mass spectrometry. Shown in FIG. 2 is the mass spectra of phosphatase-treated (bottom trace) and the mock treated (top trace) peptide mixture. The loss of the peak with the m/z of 3511 with phosphatase treatment, and the presence of the peak corresponding to the unphosphorylated peptide (m/z of 3433) allowed the inventors to positively assign a phosphorylation site to a sequence of DNA-Pkcs between amino acids 2044-2072. This peptide was then sequenced by tandem mass spectrometry (as in FIG. 1) to unequivocally identify S2056 as the site of phosphorylation.

Mass spectrometry identified the following phosphopeptide sequence, SEQ ID NO: 5, DFSTGVQSYSYS SQDPRPATGRFRRREQR, which corresponds to amino acids 2044 to 2072 of DNA-PKcs (S2056 is underlined).

EXAMPLE 2

DNA-PKcs Fragments and GST Fusion Proteins Containing Autophosphorylated Sites 20 bp oligomer primers were designed and ordered from Operon (Alameda, Calif.) using SEQ ID NO: 4 (the nucleotide sequence of DNA-PKcs, GenBank Accession Number: P78527) to created primers to amplify cDNA sequence that encodes the phosphorylation sites, T2609 and S2056. Designed DNA-PKcs cDNA fragments that cover the phosphorylation sites in DNA-PKcs found by mass spectrometer were PCR amplified from the full-length DNA-PKcs cDNA (isolated and described by several of the inventors in Kurimasa et al., *Mol Cell Biol* 19:3877-3884, 1999) using the custom designed PCR primers under normal PCR thermal cycling conditions. The reactions were carried out using pfu DNA polymerase (Stratagene, La Jolla, Calif.) and Gene-Amp® 9600 thermocycler (Perkin Elmer). The amplified cDNA fragments were cloned in frame into GEX-KG vector (Guan & Dixon 1991 *Analytical Biochem.* 192:262-67) for fusion between domains of DNA-PKcs and GST.

These clones were made to express the following residues of DNA-PKcs from the indicated corresponding cloned cDNA sequence: 1879-2182 cDNA (SEQ ID NO: 18), 1879-2267 cDNA (SEQ ID NO: 19), 2261-2700 cDNA (SEQ ID NO: 21), 2275-2702 cDNA (SEQ ID NO: 23), 2429-2702 cDNA (SEQ ID NO: 24), 2561-2700 cDNA (SEQ ID NO: 25), and 2600-2702 cDNA (SEQ ID NO: 26).

Peptide fragments were expressed by the clones which encode the following peptides and correspond to the following residues of DNA-PKcs: 1879-2182 (SEQ ID NO: 6), 1879-2267 (SEQ ID NO: 7), 1879-2700 (SEQ ID NO: 8), 2261-2700 (SEQ ID NO: 9), 2500-2702 (SEQ ID NO: 10), 2275-2702 (SEQ ID NO: 11), 2429-2702 (SEQ ID NO: 12), 2561-2700 (SEQ ID NO: 13), and 2600-2702 (SEQ ID NO: 14).

Several of these fragments were also made into glutathione-S-transferase (GST) fusion proteins. The PCR'd fragments were cut randomly and then fused with the GST protein using the commercially available GST fusion vector (Amersham Biosciences, Piscataway, N.J.).

EXAMPLE 3

Preparation of Cellular Nuclear Extracts from Cells

The preparation of nuclear extract from HeLa cells for the Examples that follow were made as generally described by Lees-Miller et al., Mol Cell Biol 10: 6472-6481, 1990 and is herein described. The cells were washed twice with cold PBS, collected, and spun at 2000 g for 5 min. The cell pellet is washed once with 5 ml LSB and spun again. The pellet is resuspended in 1 ml LSB and transfer to a centrifuge tube. (LSB (low salt): 10 mM Hepes pH7.5, 25 mM KCl, 10 mM NaCl. 1 mM $MgCl_2$, 0.1 mM EDTA).

After spinning down again, the volume of the cell pellet is estimated, then resuspended in 1× Pack cell volume (PCV) of LSB (with 50 mM NaF, 1 mM DTT. 0.5 mM PMSF, and other protease inhibitors), set in ice 5 min, and freezed in liquid $N_2$. Thaw, and spin immediately at 10,000 g for 10 min. Dispose of Supernatant (S10, cytosol fraction.

The pellet is again resuspended in 1× pack nuclear volume (PNV) of LSB with 0.5M NaCl and 10 mM $MgCl_2$ (500 mM NaCl, 10 mM $MgCl_2$, 50 mM NaF, 1 mM DTT 0.5 mM PMSF), set in ice for 10 min. For this step, LSB (0.5 M salt): 10 mM Hepes pH7.5, 25 mM KCl, 500 mM NaCl. 10 mM $MgCl_2$, 0.1 mM EDTA. The pellet is spun down at 40,000 g for 20 min, supernatant (P10 nuclear fraction). The collected P10 nuclear extract is mixed 1:1 with 2× Laemmli buffer (80 mM Tris-HCl pH 6.8, 2% SDS, 10% glycerol, 0.1% BPB), then the sample is boiled at 100° C. for 3 min.

EXAMPLE 4

SDS Gels and Western Blots for DNA-PKcs

Western blotting for the following Examples was performed as generally described by Chan et al., Biochem Cell Biol 74: 67-73, 1996 and herein described.

Preparation of 8% low bisacryiamidie gels. Resolution gel rnix (10 ml): 3 ml 30% acrylamide, 0.4 ml 2% bisacrylamide, 2 ml 1M Tris-HCl pH8.8, 3 ml water, 100 ul 10% SDS, 100 ul 10% APS, 8 ul TEED, allow to polymerize for at least 90 min. Stacking gel mix (5 ml): 3.4 ml water, 0.83 ml 30% acrylamide, 0.63 ml 1M Tris pH6.8, 50 ul 10% SDS, 50 ul 10% APS, 5 ul TEMED, allow to polymerize for at least 30 min.

Gel Running. Load the samples and run at 100V 1.5 to 2 hrs until BPB dye runs off. The electrophoresis running buffer is made as followed (per liter): 6 g Tris base, 28.8 g Glycine, 1 g SDS. Do not pH.

Transfer. Remove gel from glass plates and place in 50 ml electroblot, gently rock for 5-15 min. Electroblot (per liter): 5.8 g Tris base, 2.93 g glucine, 0.38 g SDS, 100 ml methanol. For each gel to be blotted, prepare 2 squares of 3 mm filter paper cut to size of gel and place them in electroblot. Cut 1 square piece of nitrocellulose or PVDF membrane about the same size.

Wet the PVDF membrane with Methanol, and equilibrate in electroblot for 5 min before use. For nitrocellulose, place directly in electroblot. Submerse blotting cassette and Scotchbrite pads in electroblot, assemble as follows: towards the black side of the cassette, scotchbrite (sponge), 3 mm filter paper, gel, nitrocellulose membrane, 3 mm filter paper, and then scotchbrite. Make sure that no air bubbles are trapped between the gel and the nitrocellulose membrane by smoothing out with gloved finger or rolling with a glass rod. Place assembly in transfer chamber with black side to black side; add the frozen cooling pack and fill to top with electroblot. Transfer at 100V (~250 mA) for 1 hour on ice bath or 15V overnight at RT with gentle stirring of the electroblot.

Western Blot. Place membrane in block solution (5% none fat milk powder in TTBS) for at least 60 min. TTBS: 10 mM Tris pH 8.0, 150 mM NaCl, 0.1% TWEEN-20.

Incubate the blot with primary antibody for 1 to 2 hrs at RT, 1:1000 dilution of purified DNA-PKcs antibodies in block solution. Wash blot with TTBS for 10 min, three times. Incubate blot with secondary antibody for 30 min at RT, 1:5000 dilution of goat anti-rabbit HRP conjugate (Santa Cruz Biotechnology, Inc., Santa Cruz, Calif.) in TTBS.

Wash blot with TTBS for 10 min, three times. Make up ECL solutions (Amersham Biosciences, Piscataway, N.J.): 1 ml of each A and B is sufficient for a blot. Immerse blot in ECL solution for 1 minute, remove from ECL solution, place in a sandwich of plastic wrap, expose blot to film in dark room for various times (5 sec to 10 min), and develop film.

EXAMPLE 5

Cellular Radiation Sensitivity and Defective DSB Repair in Cells Having T2609A and S2056A Mutant Proteins To investigate the biological significance of the T2609 and S2056 phosphorylation in relation to DNA repair, wild-type or mutant DNA-PKcs were tested for DNA DSB repair, and radiation survival. DNA-PKcs expression constructs were made and transfected into the DNA-PKcs-defective V3 CHO cell line (Kurimasa et al., J Immunol. 2000 Oct. 1;165(7): 3883-9). Stable V3 cell lines that were expressing wild-type DNA-PKcs (V3-F18), T2609A DNA-PKcs mutant proteins (V3-T2609A), S2056A DNA-PKcs mutant proteins (V3-S2056A) and S2056A/T2609A DNA-PKcs double-mutant proteins (V3-S2056A/T2609A) were isolated and evaluated for DNA-PKcs protein expression levels, radiation sensitivity and DNA repair defects. The radiation sensitivity of these cell lines was examined by assaying for their colony forming ability after IR.

The following was used to carry out site-directed mutagenesis and isolation of the mutant cell lines. The creation of the T2609A mutant (V3-T2609A) is herein described. The S2056A DNA-PKcs mutant (V3-S2056A) and S2056A/ T2609A DNA-PKcs double-mutant (V3-S2056A/T2609A) were generated using the same methods but different primers.

First, a 3 kb Hind III fragment of DNA-PKcs cDNA covering T2609 was used as the template for generating the T2609A mutation of DNA-PKcs cDNA. Site-directed mutagenesis was performed using the QuikChange® site-directed mutagenesis kit (Stratagene, La Jolla, Calif.) and the forward (tccgatgtttgtggaggaccaggcctcccagggc) (SEQ ID NO: 27) and reverse (gccctgggaggcctggtcctccacaaacatcgga) (SEQ ID NO: 28) primers. The mutated DNA-PKcs cDNA fragment was assembled back into the full length DNA-PKcs cDNA as described in Kurimasa et al., Mol Cell Biol 19: 3877-3884, 1999. Cells were maintained at 37° C. in a humidified atmosphere of 5% $CO_2$ in air by using alpha-MEM medium supplemented with 10% fetal calf serum, 100 U of penicillin per ml, and 100 μg of streptomycin per ml. Transfection of the DNA-PKcs expression plasmid was performed with a calcium phosphate transfection system (Catalog no. 18306-019; Gibco-BRL, Gaithersburg, Md.). For each $10^6$ cells in a 100-mm tissue culture dish, 10 μg of the DNA-PKcs expression vector and 10 μg of the pSV2neo or pPur plasmid were transfected.

T2609A DNA-PKcs expression plasmid together with pSV2neo plasmid were transfected into the V3 cell line. Forty-eight hours after transfection, cells were replated on selection medium containing 400 μg/mL of G418 for 10 days. After 7 to 21 days of selection, individual colonies were isolated and further cultured.

Colony formation and FAR (Fraction of Activity Released) assays were performed as previously described (Kurimasa et al., *Mol Cell Biol* 19: 3877-3884, 1999).

Radiation survival assays generated survival curves for each cell line. These survival curves were obtained by measuring the colony-forming abilities of irradiated cell populations. Three hundred cells were plated on 60-mm plastic petri dishes and irradiated with 137 Cs γ rays at 2 h after plating at a rate of 2.2 Gy/min to achieve a cumulative dose of 1, 2, 3, or 5 Gy. After 7 to 14 days, cells were fixed and stained with 1% crystal violet in a 70% ethanol solution, colonies containing more than 20 cells were scored, and the mean value for triplicate culture dishes was determined. Cell survival was normalized to plating efficiency of untreated controls for each cell type.

Figure 3A:
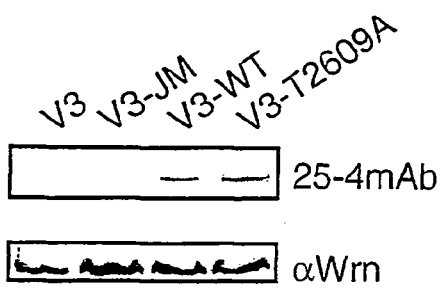
FIG. 3A is a Western blot showing DNA-PKcs protein expression levels of vector along (V3-JM), full-length wild-type DNA-PKcs (V3-F18) and T2609A mutant of DNA-PKcs in V3 cell line (top). Hamster Werner proteins were analyzed to show equal sample loading (bottom).

Referring now to FIG. 3A, nuclear extracts were prepared as described in Example 3 from V3 cells transfected with vector alone (V3-JM), full length wild-type DNA-PKcs (V3-WT) or DNA-PKcs containing the T2609A point mutant (V3-T2609A1) were analyzed for DNA-PKcs protein expression levels (top panel). Nuclear extracts (P10) were prepared as described in Example 3. 20-60 μg of each sample was analyzed by western blotting as described in Example 4. For analysis of the V3 cell lines, the DNA-cellulose pull-down method of Finnie et al. (*Proc Natl Acad Sci USA* 92: 320-324, 1995) was used to first concentrate DNA-PKcs onto the cellulose and then subjected to SDS-PAGE for western blotting. Hamster Werner proteins were analyzed to demonstrate equal sample loading (bottom panel). DNA-PKcs protein levels in V3 (lane 1) is undetectable due to low abundance of DNA-PKcs RNA, whereas, V3-WT (lane 3) and V3-T2609A (lane 4) showed similar levels of protein expression (FIG. 3A, top panel). On the bottom, the expression of wrn (another DNA repair protein) was determined to show the equal loading of the samples.

Figure 3C:
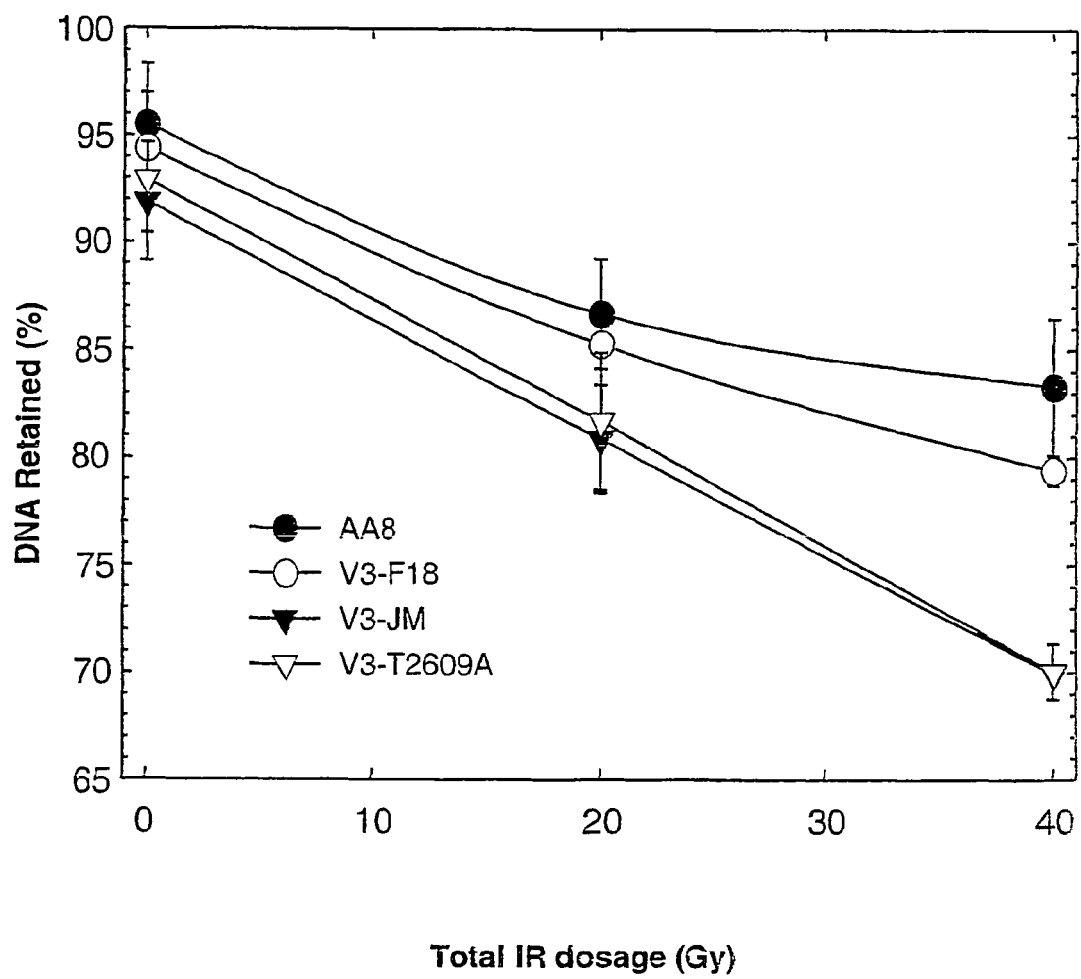
FIG. 3C is a graph showing that the T2609A and S2056A mutations compromise DSB repair in cells as determined by the fraction of activity released (FAR) assay.
Figure 3B:
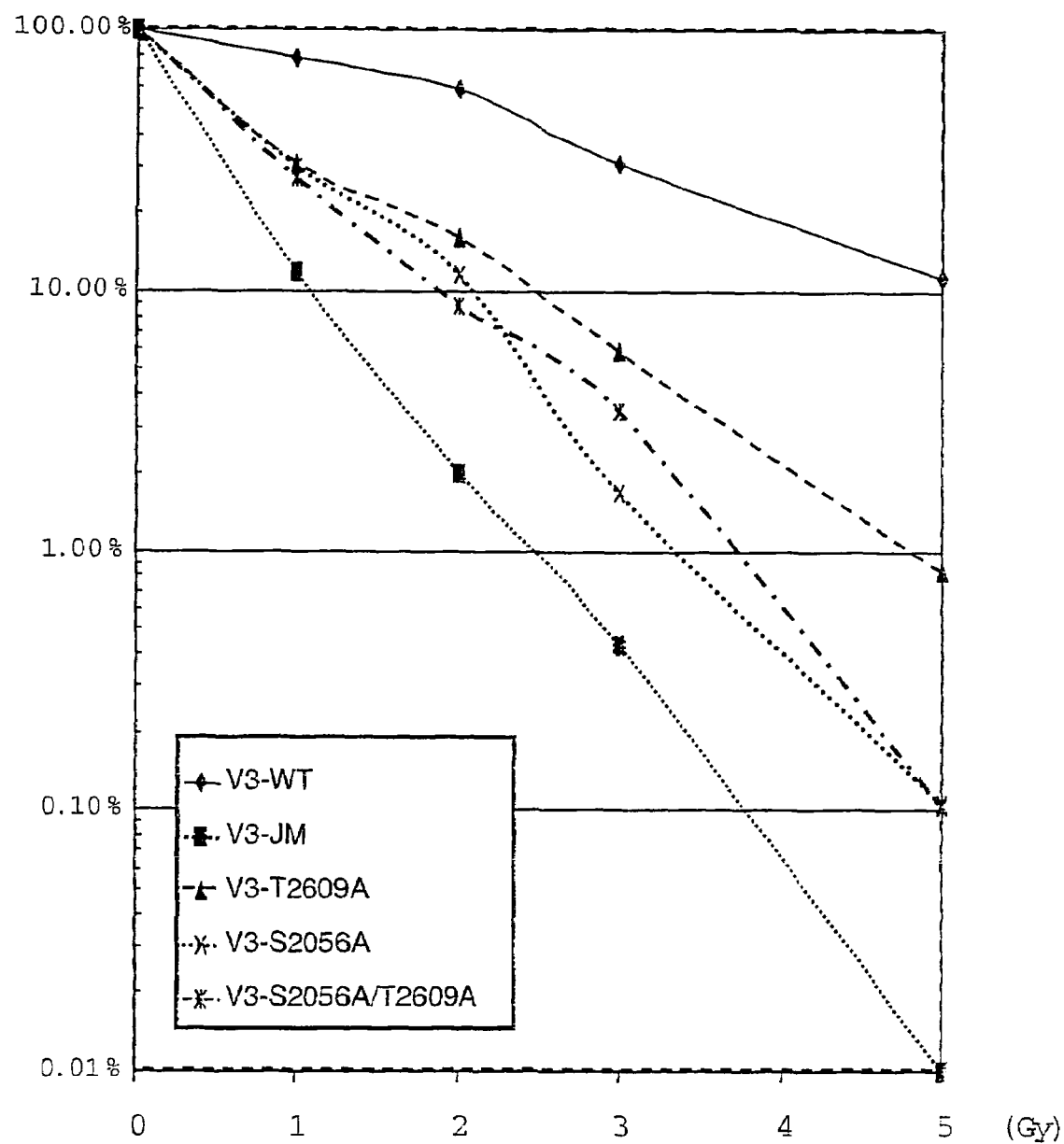
FIG. 3B is a graph showing that the T2609A, S2056A and the T2609A/S2056A double mutation increase cellular radiation sensitivity.

Complementation of human DNA-PKcs in V3 cells restored radioresistance resulting in survival that is comparable to wild-type CHO cells (FIG. 3B). In FIG. 3B, the V3 cells complemented with the S2056A mutation DNA-PKcs (V3-S2056A), T2609A mutation DNA-PKcs (V3-T2609A) and S2056A/T2609A double mutation DNA-PKcs (V3-S2056A/T2609A) showed a radiation sensitivity phenotype that was more severe than the wild type. Although expression of the S2056A and T2609A mutant proteins improved the survival of the V3 cell line, the survival rates were significantly lower than what was observed for V3-WT. The dose of IR required for 10% survival of the V3-JM, V3-S2056A, V3-T2609A, V3-S2056A/T2609A, and V3-WT cell lines was 1.2 Gy, 1.9 Gy, 2.4 Gy, 2.1 Gy, and 5 Gy, respectively (FIG. 3B). Thus, the $D_{10}$ value is approximately four-fold higher for V3-WT compared to the V3-JM non-complemented cells (that is 5 Gy/1.2 Gy), whereas resistance at the 10% survival level was increased by only two-fold in the V3-T2609A1 cells (5 Gy/2.4 Gy). However, the resistance at the 10% survival level is increased by about 2.5 times in the cell lines containing the S2056A mutation, thus showing the significance of phosphorylation of the S2056 site in radioresistance. At around 4 Gy, both the S2056A mutant and the double mutant drop below 1.0% survival rate, showing a greater radiosentivity is caused by mutating the S2056 site than the T2609 site alone. At a dosage of 5 Gy, the T2609A mutant survival rate was less than 1% while the wild type cells having functional DNA-PKcs showed a 10% or greater survival rate. Therefore, phosphorylation of T2609 and S2056 are shown to be important for cell viability in response to ionizing radiation (IR).

The presence of additional DNA-PKcs phosphorylation sites may explain why the V3-T2609A1 cells showed only a roughly two-fold increase in radiation sensitivity (at 10 Gy, FIG. 3B). In response to DNA damage, phosphorylation of multiple sites may be required for proper DNA-PK function, and thus explaining why mutation of T2609 produced only a two-fold increase in radiation sensitivity, but the mutation of S2056 produced a greater increase to radiation sensitivity.

In FIG. 3C, T2609A mutation compromises DSB repair as shown by the FAR (fraction of activity released) Assay which is a DSB rejoining assay. The FAR Assay is used to analyze the mobility of genomic DNA in the polyacrylamide gel electrophoresis (PAGE) and to measure the presence of DNA DSBs. The FAR assay uses pulsed field gel electrophoresis to indirectly measure the intactness of DNA in cells after gentle lysis in agarose plugs by quantifying the amount of DNA released from the wells immediately after IR exposure as a function of dose or after a period of incubation to allow repair after a given dose (Story et al., *Int J Radiat Biol* 65: 523-528, 1994).

The V3-JM, V3-WT, V3-T2609A1 cell lines and the parental CHO cell line (AA8) were irradiated at the indicated dose and analyzed for the presence of DSBs by the FAR assay. DNA DSB repair activity following exposure to ionizing radiation was measured by two different methods: (i) rejoining kinetics, plotted as a function of time course after irradiation; and (ii) measure of residual DNA DSB lesions following exposure and recovery to three doses (0, 20, and 40 Gy) of 137 Cs γ rays. Exposures consisted of a dose rate of about 4 Gy/min on ice. Immediately following irradiation, the cold medium was replaced with medium that had been warmed to 37° C. and the cells were placed in a 37° C. tissue culture incubator for 4 h to allow for DNA DSB repair. The cells were then trypsinized on ice, washed, suspended in agarose plugs, lysed, and electrophoresed. Residual DNA DSB lesions were determined by CHEF pulsed-field gel electrophoresis combined with a storage phosphorimaging system. Rejoined lesions were defined as the fraction of DNA that had regained sizes large enough to prevent migration during electrophoresis (DNA retained) and measured by comparing the intensity of fluorescence of the DNA fraction retained in the agarose well.

Referring now to FIG. 3C, there is a graph showing the results of the FAR assay utilized to evaluate the ability of each of the three cell lines to rejoin DSBs induced by IR. The graph plots the percentage of DNA retained in the well (which shows DSB rejoining capacity) versus total radiation dosage. The V3-WT and the parental AA8 CHO cell lines showed comparable DSB rejoining capacities (FIG. 3C, open (80% retained) and closed circles (85% retained), respectively) and. In contrast, the V3-JM and the V3-T2609A cells were significantly more defective in the rejoining of DNA DSBs at 4 hrs after irradiation (only 70% of DNA retained in well), consistent with previous observations (Kurimasa et al. *Mol Cell Biol* 19: 3877-3884, 1999) and with the hypothesis that DNA-PKcs plays an important role in repair of DSBs. Together, these results show that phosphorylation of DNA-PKcs at T2609 is important for rejoining of DSBs and for cell survival in response to DNA damage caused by IR.

EXAMPLE 6

Generation and Specificity of Phosphospecific Polyclonal Antibodies to pT2609 Site and pS2056 Site To study the in vivo phosphorylation status of DNA-PKcs at T2609 and S2056, phosphsphospecific antibodies were generated. The phosphospecific antibodies, pT2609Ab, recognizes phosphorylated T2609, and pS2056Ab recognizes phosphorylated S2056. pT2609 polyclonal antibodies were prepared by immunizing New Zealand white rabbits with a KLH-conjugated phosphopeptide. N'-TPMFVET[PO$_3$] QASQGT-C' (SEQ ID NO: 1). pS2056 polyclonal antibodies were prepared by immunizing New Zealand white rabbits with KLH-conjugated phosphopeptide, N'-QSYSYSS[PO$_3$] QDPRPAC-C' (SEQ ID NO: 2).

KLH-Conjugated Phosphopeptide. To create the KLH-conjugated phosphopeptide (SEQ ID NO: 1 and 2), the phosphopeptide was made by conventional oligonucleotide synthesis means by AgBio, Inc. (Fremont, Calif.). 10 mg of the phosphopeptide was dissolved in 0.05 mL DMSO first, then 1 mL PBS (PBS: 0.1 Phosphate buffer+0.15 M NaCl, pH 7.3) was added and mixed. Activated KLH (10 mg Soluble keyhole limpet hemacyanin) (Calbiochem #374817, EMD Biosciences, San Diego, Calif.) was mixed with the dissolved peptide and the mixture was incubated at 4° C. with gentle rotation for overnight or room temperature (RT) for 3 hours. At the end of the first incubation, 10 mg cysteine (L-cysteine HCl, Sigma, St. Louis. Mo.) in 2 mL PBS was added to the mixture, then vortexed briefly.

The phosphopeptides were conjugated to KLH by cross-linker Sulfo-SMCC (Pierce Biotechnology, Inc., Rock-ford, Ill.) which forms a disulfate bridge with the cysteine residues placed at the C' terminal of the synthesized peptides and cysteine residues on KLH. The mixture was then incubated with rotation at RT for 2 hours to block unreacted SMCC. Dialysis against 2 L PBS was done with at least 2 buffer changes. Dialysis may proceed overnight. In place of dialysis, a Sephadex® G-25 column (Amersham Biosciences, Piscataway, N.J.) may be used again to desalting.

The peptide/KLH conjugate solution was collected in dialysis bag or in fractions (in case of G-25 gel) and 18 mg NaCl to each mL of the solution was dissolved to give the solution additional 0.3 M NaCl. The solution was centrifuged if particulates or precipitates observed. The protein concentration of the clear conjugate solution was measured by using $A_{280nm}$ and a coefficient 1.4=1 mg/mL. The conjugate solution was then diluted to 1 mg/mL and aliquoted 1 mL of the peptide-KLH conjugate solution into tubes. Each tube contained 1 mg of the conjugate and was sufficient for one immunization dose for two rabbits. The tubes were stored at −20° C. until use.

The polyclonal antibodies were made by immunizing New Zealand white rabbits with the above KLH-conjugated phosphopeptide, (SEQ ID NO: 1 and 2) using standard methods well known in the art by AgBio, Inc (Fremont, Calif.). Crude rabbit serum was collected from the immunized rabbits. The KLH-conjugated phospho peptides were then mixed with adjuvant and were injected into a rabbit through intradermal injection to elicit immunogenic response. After repeated injection to boost the immunogenic response, samples of serum were collected and tested by ELISA assay (to determine the titer of the antibodies) until the titer reached to the peak. The antibodies were then harvested.

The phosphospecific antibodies were affinity purified through a phosphopeptide-conjugated Sepharose® CL-4B column. SEQ ID NO: 1 was made as an unphosphorylated peptide, N'-PMFVETQASQGTC-C' which corresponds to the T2609 site unphosphorylated. SEQ ID NO: 2 was made as an unphosphorylated peptide, N'-QSYSYSSQDPRPAC-C', to correspond to the S2056 site unphosphorylated.

The following protocol was used to affinity purify the pT2609 and pS2056 rabbit polyclonal antibodies. Two columns are needed. One column uses an unphosphorylated version of the phosphopeptides used to immunize the rabbits. A second column uses the phosphopeptides. Eluted IgGs are passed through the first unphosphorylated peptide column to deplete any IgGs that are not specific to pT-2609 or pS2056 and then the flow-through is then passed through the second phosphopeptide column to affinity purify the polyclonal antibodies specific for pT2609 and pS2056.

To prepare the columns, dissolve the appropriate peptide (1 mg/per ml) in coupling buffer: 50 mM Tris pH 8.5, 5 mM EDTA. Pack 5 ml SulfoLink Coupling Gel (Pierce Biotechnology, Rockford, Ill.) in 10 ml disposable polystyrene column (Pierce Biotechnology), equilibrate the column with 6 column volumes of coupling buffer. Place the bottom cap to the column, and add 5 ml peptide solution (5 mg) to the column. Place top cap, and mix the column at RT for 15 minutes with gentle rotation. Set for 30 minutes without mixing. Drain buffer, wash column with 3 column volumes of coupling buffer. Place the bottom cap to the column, and add 5 ml 50 mM cysteine to the column. Place top cap, and mix the column at RT for 15 minutes with gentle rotation. Set for 30 minutes without mixing. Drain buffer, wash column with 16 column volumes of 1 M NaCl.

For affinity purification, wash both non-phospho and phosphospecific peptide columns with 5 column volumes of PBS. Load 15 to 30 ml crude rabbit serum onto non-phosphopeptide column in RT. Collect flow-through. This step is to remove none specific antibodies. Load the flow-through onto phosphospecific peptide column with PBS. Wash with 10 column volumes of PBS with 0.5 M NaCl. Elute with 3 column volumes of 0.1 M glycine pH2.5,. collect 1 ml fraction and neutralize the pH with 50 µl 1M Tris pH 8.0, and check protein concentration by Bradford assay (Bio-Rad, Richmond, Calif.) and freeze in −20° C.

Figure 4A:
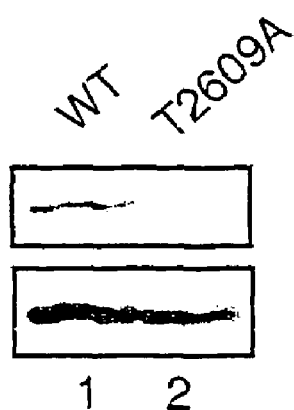
FIG. 4A is two Western blots showing that the pT2609pAb is specific for the phosphorylated T2609 site in wild type DNA-PKcs.

In FIG. 4A, GST fusion proteins, having fragments spanning amino acids 2500-2700 (SEQ ID NO: 10) fused to GST, were made according to Example 2. The fragments contained either the wild-type DNA-PKcs sequence or the T2609A point mutation. The GST fusion proteins were in vitro phosphorylated with purified DNA-PK as described in Example 2 and analyzed by Western blot according to Example 5. The wild-type DNA-PKcs sequence and the T2609A point mutation were probed with the pT2609pAb (top panel) and anti-GST (bottom panel) to show equal loading. The lack of any signal detected for T2609A by the pT2609pAb of the invention in the Western blot shows that T2609 in DNA-PKcs is phosphorylated and that the pT2609pAb is specific for the phosphorylated T2609 site.

Figure 4B:
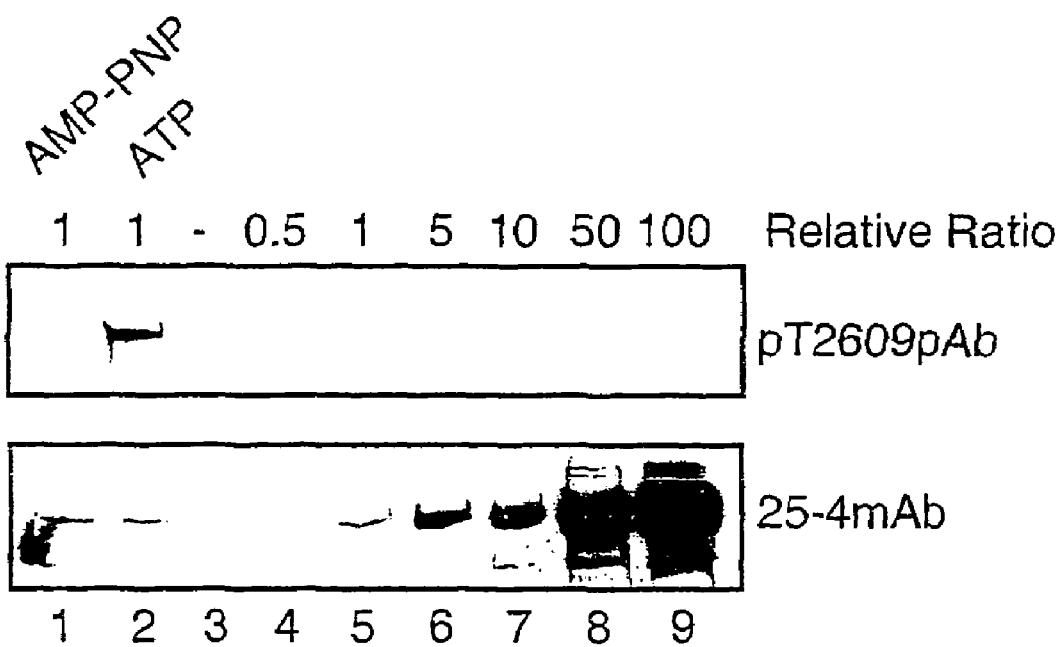
FIG. 4B is two Western blots showing that the pT2609 polyclonal antibody (pT2609pAb) does not recognize unphosphorylated DNA-PKcs at the molar ratios given as compared to 25-4 DNA-PKcs monoclonal antibody (25-4 mAb).

Referring now to FIG. 4B, the Western blot shows that pT2609pAb is specific to phosphorylated T2609 and does not recognize unphosphorylated DNA-PKcs. In FIG. 4B, affinity-purified pT2609 polyclonal antibody was used in immunoblotting with mock or autophosphorylated DNA-PKcs, lanes 1 and 2, respectively, and in the presence of excess unphosphorylated DNA-PKcs at the indicated molar excess ratios. Immunoblotting with unphosphorylated DNA-PKcs at 100 fold molar excess (relative to the phosphorylated DNA-PKcs) did not produce a detectable signal. Western blotting with pT2609pAb (top panel) and 25-4 DNA-PKcs monoclonal antibody (bottom panel) with mock or autophosphorylated DNA-PKcs (lanes 1 and 2, respectively) and with purified, unphosphorylated DNA-PKcs (lanes 3 to 9) at the indicated molar ratios relative to the amount of protein in lanes 1 and 2.

Figure 4C:
FIG. 4C is two Western blots showing that the pS2056 polyclonal antibody (pS2056pAb) does not recognize unphosphorylated S2056 in DNA-PKcs as compared to 25-4 DNA-PKcs monoclonal antibody (25-4 mAb).

Referring now to FIG. 4C, a similar experiment shows that affinity purified pS2056Ab is specific to phosphorylated S2056. V3 (DNA-PKcs deficient CHO cells) complemented with either wild type human DNA-PKcs cDNA (V3-F18) or kinase dead mutant (V3-KA4) were subjected to mock or 10 Gy of ionizing radiation. DNA-PKcs protein was immunoprecipitated from nuclear extracts by 25-4 DNA-PKcs monoclonal antibody, and western blotted with the generated pS2056 rabbit polyclonal antibody (bottom panel). The blot was stripped and reprobed with the 25-4 DNA-PKcs monoclonal antibody (top panel). S2056 phosphorylation was diminished in V3-KA4 (kinase dead mutant) as compared to that of V3-F18 (wild type DNA-PKcs) indicating that DNA-PKcs autophosphorylation is responsible for IR-induced S2056 phosphorylation.

EXAMPLE 7

Localization of pT2609 Antibody to Site of DNA Double-Strand Breaks

In response to DNA damage, many DNA repair proteins form nuclear foci, presumably, the site of the DNA DSBs (Rogakou, *J Cell Biol* 1999 Sep. 6; 146(3):905-16; Maser et al., *Mol Cell Biol*. 1997 October; 17(10):6087-96). To determine the status of DNA-PKcs in response to DNA damage, DNA-PKcs was examined by immunofluorescence microscopy. Immunostaining with a monoclonal antibody to DNA-PKcs produced strong signal throughout the nucleus, in both unirradiated and irradiated cells (not shown).

Fluorescent immunostaining showed that pT2609pAb produce foci only in irradiated but not unirradiated primary human skin fibroblasts (HSF). Immunofluorescence was performed as previously described in (Burma et al. 2001, *J Biol Chem* 276: 42462-42467). In contrast, immunostaining with 25-4 (a commercial monoclonal antibody to DNA-PKcs from Neomarkers, Lab Vision Corp, Fremont, Calif.) produced strong signal throughout the nucleus, in both unirradiated and irradiated HSFs, because DNA-PKcs is a very abundant nuclear protein.

Because DNA-PKcs is a very abundant nuclear protein, it is not possible to distinguish any foci in response to DNA damage with the monoclonal antibody. However, with the pT2609 polygonal antibody, foci can be clearly detected in response to IR treatment. The number and size of foci varied with the dose of IR and reaches a maximum with 10 Gy (data not shown). In addition, the kinetics of the pT2609pAb foci formation is similar to what was observed with the time-course western results in FIG. 5B.

To further confirm the localization of T2609 phosphorylation at DSB sites, we examined the colocalization of rabbit pT2609 polyclonal antibody foci with the p53 binding protein (53BP1) which has been previously shown to bind to the site of DNA DSBs (Rappold et al., *J Cell Biol.,* April 30;153(3): 613-20 2001). Co-immunostaining with a 53BP1 monoclonal antibody (Rappold et al., *J Cell Biol., April* 30;153(3):613-20 2001) and the pT2609Ab in unirradiated HSF cells did not produce any discernable foci above the background signal of the nucleus. 53BP1 monoclonal antibody were provide by Dr. Junjie Chen (Mayo Clinic, Rochester, Minn.). However, cells that were irradiated resulted in very discrete 53BP1 and pT2609pAb foci. Moreover, the 53BP1 and pT-2609pAb foci co-localized with each other. Thus by virtue of co-localization with 53BP1 foci in response to DNA damage, it was demonstrated that the pT2609pAb binds and becomes activated at the site of DNA DSB in vivo.

EXAMPLE 8

T2609 is Phosphorylated in Response to Irradiation in vivo.

Figure 5:
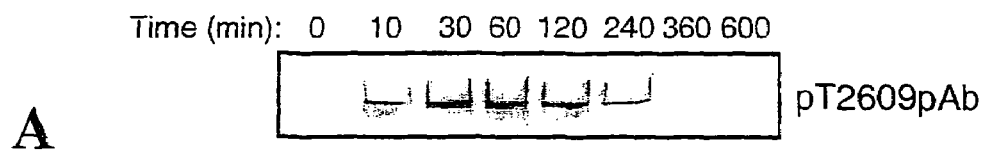
FIG. 5A is a Western blot of Hela cell nuclear extracts, probed with pT2609 antibody (upper panel) and 25-4 monoclonal antibody to DNA-PKcs (bottom panel), after either mock-treatment or irradiation with 10 Gy and recovery for various times.
FIG. 5B is a Western blot of Hela cell nuclear extracts, probed with pT2609pAb (upper panel) and 25-4 monoclonal antibody to DNA-PKcs (bottom panel), after irradiation at the indicated dose and recovery for 30 minutes.
FIG. 5C is a Western blot showing that pT2609 polyclonal antibody can be used to immunprecipitate phosphorylated DNA-PKcs from unirradiated HeLa nuclear extract (lane 1) but not unphosphorylated DNA-PKcs from extracts made from HeLa cell, irradiated with 25 Gy and harvested after 30 min recovery period. The 25-4 monoclonal antibody does not discriminate between phosphorylated or unphosphorylated DNA-PKcs.
FIG. 5D shows by Western blot that phosphorylation of T2609 in response to DNA damage can be inhibited with wortmannin treatment (left panel) and is inducible in A-T cells (right panel).
Figure 5:
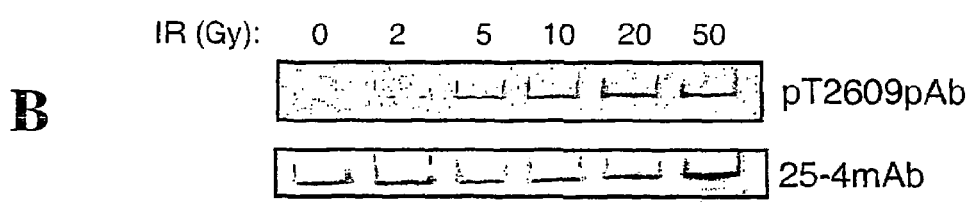
Figure 5:
Figure 5:
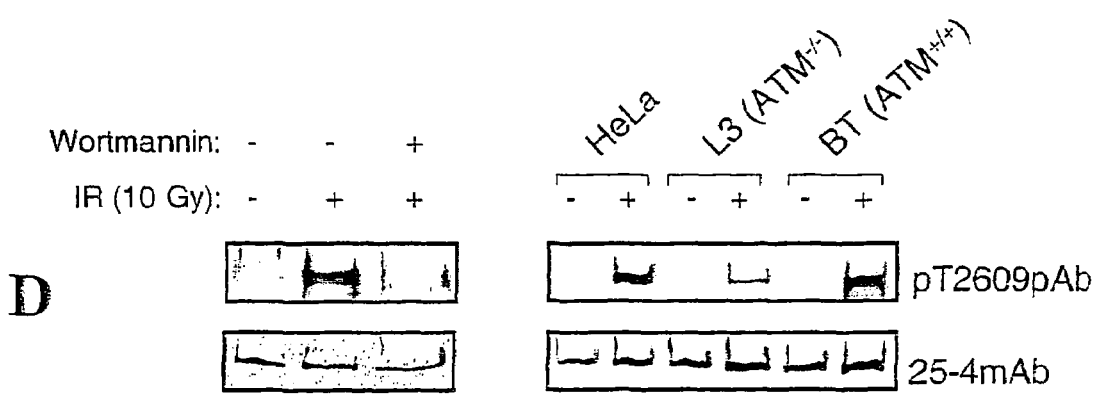

Referring now to FIG. 5A, 50 µg of HeLa nuclear extracts made from unirriadiated (lane 3) or cells irradiated with 25 Gy and harvested after a 30 min recovery period, were analyzed by western blotting with pT2609pAb (upper panel) or 25-4 monoclonal antibody (bottom panel). As shown in FIG. 5A, phosphorylation of T2609 is DNA damage inducible and was detected as early as 10 minutes and reached a maximum at approximately 30 minutes after treatment. T2609 is phosphorylated up to 4 hours after IR treatment detectable, after which the phosphorylation of T2609 is not detectable (FIG. 5A). Purified DNA-PKcs was mock (lane 1, control) or autophosphorylated (lane 2) and analyzed by western blotting using the pT2609 polyclonal antibody of the invention. HeLa cells were either mock treated or irradiated with 10 Gy and allowed to recover for the indicated times. Nuclear extracts were western blotted with pT2609pAb (top panel) and then blots were stripped and reprobed with the 25-4 DNA-PKcs monoclonal antibody (Neomarkers, Lab elision Corp, Fremont, Calif.) (bottom panel). Since phosphorylation of T-2609 can be detected as early as 10 minutes after IR, this suggests that phosphorylation of DNA-PKcs is an early event in response to DNA damage and is consistent with the hypothesis that DNA-PK is required for the early and rapid phase of the "biphasic" model of DSB repair. This biphasic model was previously described in DiBiase et al., *Cancer Res* 2000 Mar. 1;60(5):1245-53.

Phosphorylation of T2609 is also dose dependent, and can be induced with 2 Gy of IR and reaches a maximum or saturation with 10 Gy of IR. As shown in FIG. 5B, HeLa cells were irradiated with the indicated dose of IR and allowed to recover for 30 min. Nuclear extracts were first analyzed by western blot with pT2609pAb (top panel) and then with 25-4 monoclonal to show equal loading (bottom panel). Since phosphorylation of T2609 can be observed with a dose as low as 2 Gy, these results suggest that phosphorylation of DNA-PKcs is very sensitive to the presence of DSBs in the genome. The inventors have also observed the same phosphorylation of T2609 in response to IR in a lymphoblastoid cell line (Jurkat), a glioma cell line (M059K) and in primary human fibroblasts (data not shown), and thus this event appears to be a general phenomenon that is not cell-type specific.

Phosphorylation at T2609 in response to DNA damage was further confirmed by immunoprecipitation with the pT2609pAb. As shown in FIG. 5C, pT2609 polyclonal antibody was used to immunoprecipitate DNA-PKcs from 500 µg of unirradiated HeLa nuclear extract (lane 1) or extracts made from HeLa cells irradiated with 25 Gy and harvested after 30 min recovery period. DNA-PKcs was immunoprecipitated with the pT2609pAb only in the nuclear extracts prepared from irradiated cells but not from that of untreated cells, thus showing that the pT2609pAb is specific for phosphorylated DNA-PKcs.

In FIG. 5D, phosphorylation of T2609 in response to DNA damage can be inhibited with wortmannin treatment and is inducible in A-T cells indicating that DNA-PKcs autophosphorylation is responsible for T2609 phosphorylation in vivo. The activity of PI-3 kinase family members, including DNA damage responsible DNA-PK and ATM, are sensitive to low dose of wortmannin (Sarkaria et al., *Cancer Res.* 1998 Oct. 1;58(19):4375-82). Since phosphorylation of T2609 is through an autophosphorylation mechanism, then one would expect phosphorylation to be sensitive to the effects of wortmannin. Treatment of HeLa cells with 20 μm wortmannin, resulted in a decrease in the detectable levels of phosphorylated T2609 (FIG. 5D).

To determine whether the ATM (ataxia-telangiesctasia-mutated) kinase may phosphorylate T2609 in response to IR, ATM deficient lymphoblastoid cell line (L3) and ATM positive cell line (BT) were treated with ionizing radiation and probed with pT2609pAb. In response to IR, phosphorylation of T2609 was observed in both the ATM wild-type (BT) and mutant (L3) cell lines, thus phosphorylation of DNA-PKcs at T2609 is ATM-independent.

EXAMPLE 9

Phosphorylation of S2056 in vivo

Figure 6:
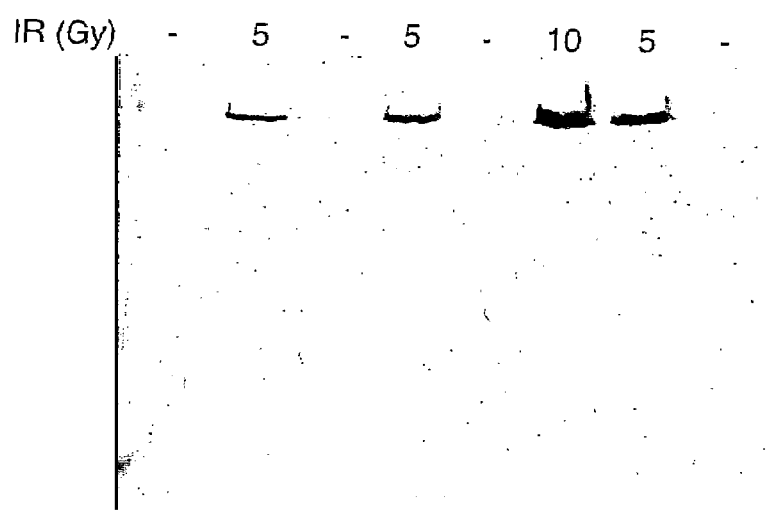
FIG. 6A is a Western blot showing that phosphorylation of S2056 is IR-inducible.
FIG. 6B is a time course Western blot of IR-inducible phosphorylation of Ser 2056.
Figure 6:
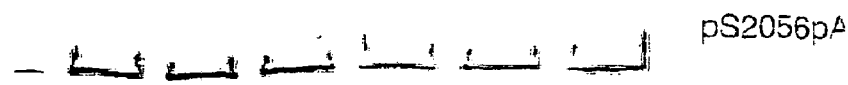

The observed S2056 phosphorylation in vivo data is similar to that of T2609. The experiments described in the previous Example were performed using p2056 polyclonal antibody (pS2056pAb) to observe the phosphorylation of S2056 in vivo. Referring now to FIG. 6A, phosphorylation of S2056 induced by irradiation in vivo was observed in HeLa cells (lane 2), wild type fibroblasts (lane 4), as well as ATM (ataxia-telangiesctasia-mutated) deficient fibroblasts (lanes 6 and 7). S2056 phosphorylation in response to IR in ATM deficient fibroblasts also indicates that DNA-PKcs autophosphorylation is likely responsible for S2056 phosphorylation in vivo. The gel in FIG. 6A shows that the pS2056pAb detects phosphorylated DNA-PKcs only in irradiated cells (lanes 2, 4, 6 and 7) but not unirradiated cells (lanes 1, 3, 5 and 8). In addition, fluorescent immunostaining with pS2056 antibody show that pS2056pAb detects only phosphorylated DNA-PKcs and is localized at DSB sites (nuclear foci) only in irradiated but not unirradiated cells (data not shown).

Referring now to FIG. 6B, a main difference between T2609 and S2056 phosphorylation is that prolonged phosphorylation of S2056 can be detected upon DNA damage. S2056 phosphorylation can be detected six to eight hours after IR whereas T2609 phosphorylation is diminished after about 4 hours indicating the phosphorylation at T2609 and S2056 may have overlapping and distinct functions.

EXAMPLE 10

Generating pT2609 and pS2056 Monoclonal Antibodies

Specific mouse monoclonal antibodies against pT2609 and pS2056 were prepared using immunogens disclosed herein. Protocols for immunization and construction of hybridomes may be found in U.S. Pat. No. 4,455,296 to Hansen et al and U.S. Pat. No. 4,364,933 to Kong et al and are hereby incorporated by reference. The screening process, is as described in Example 6. The cell lines and monoclonal antibodies recognizing only the phosphopeptides but not non-phosphopeptides are selected. Therefore, there is no need of affinity purification of Example 6 for the phospho specific mouse monoclonal antibodies. Monoclonal antibodies to phosphorylated T2609 (pT2609mAb) and phosphorylated S2056 (pS2056mAb) were generated according to the protocol herein described.

Female BALB/c mice were subcutaneously injected with 100 μg/mouse into one spot with the phosphopeptide once a month for 4 months. The phosphopeptide was added to incomplete Freund's adjuvant. Testbleeds from mice's tail were drawn once a month after sterilizing mice skin with 70% alcohol. After 4 months of immunization, mice were given a final booster injection 4 days before doing fusion. The phosphoprotein was injected without adjuvant. The polyclonal mouse serum was collected from the hearts. The mice were sacrificed and the spleens and NS-1 myeloma cells were harvested.

The fusion of the harvested mouse NS-1 cells and spleen cells (B lymphocyte cells) was carried out according to the following method. Prepare hypoxanthine-aminopterin-thymidine (HAT, Sigma) medium (300 ml 15% RPMI medium+ HTA) two days before. Defrost NS-1 cells (ATCC, Manassus, Va.) and cultured in 15% RPMI medium (Gibco BRL, Gaithersburg, Md.) (with 15% Fetal Bovine Serum obtained from Hyclone (Logan, Utah)). Prewarm 2 ml 50% PEG, 5 and 15 ml RPMI, and 15% RPMI-HAT medium at 37° C.

Rinse the spleen in 5 mL RPMI in 60 mm petri dishes five times. Collect the speen cells and put into 15 ml centrifuge tubes (4° C.). Pass the spleen cells through 25-gauge needles three times and 21-gauge needles three times. Spin at 4° C., 1800 rpm, 5 minutes. Collect NS-1 cells (about 200 ml culture) and put into 50 ml centrifuge tubes.

Spin at 4° C., 1400 rpm, 5 minutes. Resuspend spleen cells with 5 ml RPMI medium and stand for 2 minutes. Transfer the supernatant of spleen cells into a new 50 ml tube and repeat spin at 4° C., 1400 rpm, 5 minutes and resuspend spleen cells with 5 ml RPMI medium and stand for 2 minutes. Re-suspend the NS-1 cells in 15 ml RPMI and transfer into one 50 ml tub. Spin NS-1 cells, resuspend pellets and spin, and then resuspend the pellets with 20 ml RPMI medium. Spin spleen cells, 4° C., 1800 rpm, 5 min, resuspend the pellets with 4 ml RPMI medium. Count cell numbers in 2 μL spleen cells in 88 μl ammonium chloride (incubate 5 min, lysis RBC) and 10 μl tryphan blue (before counting). Count number of cells in 5 μl NS-1 cells, 40 μl PBS and 5 μl tryphan blue.

Keep some spleen ($5 \times 10^6$) and NS-1 ($1 \times 10^6$) cells as control. Transfer optimum amount of NS-1 cells into spleen cell tube. The optimum amount is 1:5=NS-1 cells:Spleen cells. Spin at 4° C., 1800 rpm, 5 min and completely remove the supernatant. Drop by drop over 1 min period, add 1 ml prewarmed 50% PEG with continually shaking the tube, shaking 30 sec, stand for 1 min (37° C.). Drop by drop over 5 min period, add 5 ml RPMI medium to the fusion mixture while gently agitating (37° C.). Immediately add 15 ml RPMI medium over a 1 min period. Incubate the fusion mixture in 37° C. water bath for 5 min. Spin down the cell pellets at 25° C., 1800 rpm, 5 min. Re-suspend the cell pellets with 15% RPMI-HAT medium ($1 \times 10^6$ spleen cells/ml). Use normal mouse splenocytes as feeder cells (seeding before cell fusion). Seed the cell suspension in 96 well plate (200 μl/well), culture two weeks. Screen positive clones by dot blot assay.

The present examples, methods, procedures, treatments, specific compounds and sequences are meant to exemplify and illustrate the invention and should in no way be seen as limiting the scope of the invention. Any patents or publications mentioned in this specification are indicative of levels of those skilled in the art to which the patent pertains and are hereby incorporated by reference to the same extent as if each was specifically and individually incorporated by reference.

What is claimed is:

1. A purified antibody which binds to an epitope consisting of SEQ ID NO: 1 which includes a phosphorylated threonine at position T2609 of human DNA-PKcs, as described in SEQ ID NO:3, wherein said antibody does not bind to the epitope when T2609 is not phosphorylated.

2. The antibody of claim 1, wherein said antibody is a monoclonal antibody.

3. The antibody of claim 1, wherein said monoclonal antibody is a human monoclonal antibody.

* * * * *

UNITED STATES PATENT AND TRADEMARK OFFICE
CERTIFICATE OF CORRECTION

PATENT NO.        : 7,491,804 B2
APPLICATION NO.   : 10/511561
DATED             : February 17, 2009
INVENTOR(S)       : Chen et al.

Page 1 of 1

It is certified that error appears in the above-identified patent and that said Letters Patent is hereby corrected as shown below:

Col. 1 lines 4-5, add the following text before the first paragraph entitled CROSS-REFERENCE TO RELATED APPLICATIONS:

-- STATEMENT OF GOVERNMENT SUPPORT

This invention was made during work partially supported by the National Institutes of Health Grant No. CA50519 and U.S. Department of Energy under Contract No. DE-AC03-76SF00098. The government has certain rights in this invention. --

Signed and Sealed this

Sixth Day of October, 2009

David J. Kappos
*Director of the United States Patent and Trademark Office*